(12) United States Patent
Sakurai et al.

(10) Patent No.: US 10,201,158 B2
(45) Date of Patent: Feb. 12, 2019

(54) PLANT DISEASE CONTROL COMPOSITION AND METHOD FOR CONTROLLING PLANT DISEASE BY APPLICATION OF SAME

(71) Applicant: MITSUI CHEMICALS AGRO, INC., Chou-ku, Tokyo (JP)

(72) Inventors: Seiya Sakurai, Oamishirasato (JP); Toshiaki Ohara, Moriyama (JP); Munetsugu Morimoto, Yokohama (JP); Nobuhiro Kondo, Chiba (JP); Hideaki Ikishima, Chiba (JP)

(73) Assignee: MITSUI CHEMICALS AGRO, INC., Chuo-Ku, Tokyo (JP)

( * ) Notice: Subject to any disclaimer, the term of this patent is extended or adjusted under 35 U.S.C. 154(b) by 0 days.

(21) Appl. No.: 15/126,407

(22) PCT Filed: Mar. 19, 2015

(86) PCT No.: PCT/JP2015/059278
§ 371 (c)(1),
(2) Date: Sep. 15, 2016

(87) PCT Pub. No.: WO2015/141867
PCT Pub. Date: Sep. 24, 2015

(65) Prior Publication Data
US 2017/0094971 A1    Apr. 6, 2017

(30) Foreign Application Priority Data

Mar. 20, 2014   (JP) .................................. 2014-057849

(51) Int. Cl.
| A01N 43/50 | (2006.01) |
| A01N 43/54 | (2006.01) |
| A01N 43/56 | (2006.01) |
| A01N 43/58 | (2006.01) |
| A01N 43/42 | (2006.01) |
| A01N 43/653 | (2006.01) |
| A01N 37/20 | (2006.01) |
| A01N 43/16 | (2006.01) |
| A01N 43/32 | (2006.01) |
| A01N 43/40 | (2006.01) |
| A01N 43/60 | (2006.01) |
| A01N 43/78 | (2006.01) |

(Continued)

(52) U.S. Cl.
CPC ............. *A01N 43/42* (2013.01); *A01N 37/20* (2013.01); *A01N 43/16* (2013.01); *A01N 43/32* (2013.01); *A01N 43/40* (2013.01); *A01N 43/50* (2013.01); *A01N 43/56* (2013.01); *A01N 43/58* (2013.01); *A01N 43/60* (2013.01); *A01N 43/653* (2013.01); *A01N 43/78* (2013.01); *A01N 43/80* (2013.01); *A01N 43/82* (2013.01)

(58) Field of Classification Search
None
See application file for complete search history.

(56) References Cited

U.S. PATENT DOCUMENTS

| 2008/0275242 A1 | 11/2008 | Ito et al. |
| 2009/0325998 A1 | 12/2009 | Ito et al. |

(Continued)

FOREIGN PATENT DOCUMENTS

| EP | 2517562 A1 | 10/2012 |
| JP | 2007-1944 A | 1/2007 |

(Continued)

OTHER PUBLICATIONS

Walter, New Fungicides and New Modes of Action, Modern Fungicides and Antifungal Compounds VI, © Deutsche Phytomedizinische Gesellschaft, Braunschweig, Germany, 2011, Chapter 7, pp. 66-73). (Year: 2011).*

(Continued)

*Primary Examiner* — Layla D Berry
(74) *Attorney, Agent, or Firm* — Buchanan, Ingersoll & Rooney PC

(57) ABSTRACT

Provided is a plant disease control composition that has a plurality of disease spectra against various plant pathogens and demonstrates superior control effects (synergistic control effects) that cannot be predicted from each component alone. The plant disease control composition comprises as active ingredients thereof at least one quinoline compounds represented by the following general formula:

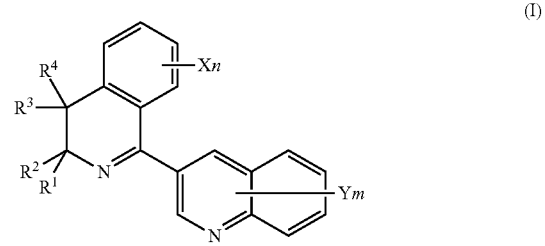

(I)

wherein, $R^1$ and $R^2$ represent, for example, optionally substituted alkyl groups or optionally substituted aryl groups, $R^3$ and $R^4$ represent, for example, hydrogen atoms, fluorine atom or methyl group, X represents, for example, a halogen atom or optionally substituted alkyl group, and Y represents a fluorine atom or methyl group, n is 0 to 2 and m is 0 or 1, or a salt thereof (group a), and one or more fungicidal compounds selected from group b.

3 Claims, No Drawings

(51) Int. Cl.
| | |
|---|---|
| *A01N 43/80* | (2006.01) |
| *A01N 43/82* | (2006.01) |
| *A01N 35/04* | (2006.01) |
| *A01N 37/36* | (2006.01) |
| *A01N 37/46* | (2006.01) |
| *A01N 37/50* | (2006.01) |
| *A01N 43/10* | (2006.01) |
| *A01N 43/28* | (2006.01) |
| *A01N 43/30* | (2006.01) |
| *A01N 43/84* | (2006.01) |
| *A01N 43/88* | (2006.01) |
| *A01N 43/90* | (2006.01) |
| *A01N 45/02* | (2006.01) |
| *A01N 47/04* | (2006.01) |
| *A01N 47/12* | (2006.01) |
| *A01N 47/14* | (2006.01) |
| *A01N 47/16* | (2006.01) |
| *A01N 47/20* | (2006.01) |
| *A01N 47/24* | (2006.01) |
| *A01N 47/26* | (2006.01) |
| *A01N 47/32* | (2006.01) |
| *A01N 47/38* | (2006.01) |
| *A01N 59/02* | (2006.01) |
| *A01N 59/26* | (2006.01) |

(56) References Cited

U.S. PATENT DOCUMENTS

| | | | |
|---|---|---|---|
| 2010/0255116 A1 | 10/2010 | Mitani et al. | |
| 2012/0282349 A1* | 11/2012 | Tamagawa | A01N 43/42 424/633 |
| 2016/0157487 A1 | 6/2016 | Tamagawa et al. | |
| 2016/0262393 A1 | 9/2016 | Cristau et al. | |

FOREIGN PATENT DOCUMENTS

| | | |
|---|---|---|
| JP | 2007-217353 A | 8/2007 |
| JP | 2010-6746 A | 1/2010 |
| JP | 2011-12017 A | 1/2011 |
| JP | 2014-15470 A | 1/2014 |
| RU | 2443110 C2 | 2/2012 |
| RU | 2483541 C2 | 6/2013 |
| WO | WO 2005/070917 A1 | 8/2005 |
| WO | WO 2007/011022 A1 | 1/2007 |
| WO | WO 2011/077514 A1 | 6/2011 |
| WO | WO 2014/079789 A1 | 5/2014 |
| WO | 2015/055707 A1 | 4/2015 |
| WO | WO 2015/124542 A1 | 8/2015 |

OTHER PUBLICATIONS

International Search Report (PCT/ISA/210) dated Jun. 30, 2015, by the Japanese Patent Office as the International Searching Authority for International Application No. PCT/JP2015/059278.
Written Opinion (PCT/ISA/237) dated Jun. 30, 2015, by the Japanese Patent Office as the International Searching Authority for International Application No. PCT/JP2015/059278.
Extended Search Report issued by the European Patent Office in corresponding European Patent Application No. 15764226.5 dated Jul. 25, 2017 (8 pages).
Office Action and Search Report issued by the Russian Patent Office in corresponding Russian Patent Application No. 2016141053 dated Jun. 25, 2018 (11 pages including partial English translation).
Office Action issued by the Columbian Patent Office in correspondence Columbian Patent Application No. NC2016/0002513 dated Oct. 17, 2018 (18 pages including partial English translation).
Avenot et al: "Sensitivities of Baseline Isolates and Boscalid-Resistant Mutants of Alternaria alternata from Pistachio to Fluopyram, Penthiopyrad, and Fluxapyroxad," The American Phytopathological Society, Plant Disease, Feb. 2014, pp. 197-205 (9 pages).
Notification of Reasons for Refusal issued by the Japanese Patent Office in corresponding Japanese Patent Application No. 2016-558150 dated Nov. 6, 2018 (8 pages including partial English translation).

* cited by examiner

PLANT DISEASE CONTROL COMPOSITION AND METHOD FOR CONTROLLING PLANT DISEASE BY APPLICATION OF SAME

TECHNICAL FIELD

The present invention relates to a plant disease control composition, which is characterized by comprising as active ingredients thereof at least one quinoline compound represented by general formula (I) indicated below in the present description or a salt thereof (group a), and one or more fungicidal compound selected from the group consisting of compounds (b-1) to (b-106) (group b), and to a method for controlling plant disease by applying that composition.

BACKGROUND ART

Numerous chemical agents have conventionally been used to control plant diseases. However, the frequent use and over-administration of chemical agents having a similar structure and similar mode of action to control the same types of plant diseases has resulted in the significant problem of plant pathogens becoming resistant to these chemical agents.

On the other hand, there is currently a growing demand among consumers for agricultural products that are grown using reduced levels of agricultural chemicals as well as a social demand for a reduction in the burden that agricultural chemicals place on the environment.

In addition, in the case of treating agricultural crops by mixing two or more types of chemical agents by tank mixing at farm fields where chemical agents are actually used, the combining of incompatible chemical agents may cause a mutual reduction in the effects of the chemical agents or result in a considerable risk of causing phytotoxicity.

In consideration of such circumstances, there is a desire for a plant disease control composition that is highly effective against organisms that are resistant to existing chemical agents and exhibits higher efficacy using a smaller amount of active ingredient. Moreover, there is also a desire for a highly compatible plant disease control composition composed of components (compounds) having different basic structures and different modes of action and method for controlling plant disease in order to prevent plant pathogens from acquiring resistance.

A quinoline compound represented by general formula (I) is known to demonstrate control effects as a fungicide against rice blast (*Pyricularia oryzae*) and against gray mold (*Botrytis cinerea*) in tomatoes, cucumbers and green beans by treating plants by seed disinfection or foliage spraying and the like (Patent Documents 1 to 4), while the mixing of a quinoline compound represented by general formula (I) with a certain type of fungicide is disclosed in Patent Document 5.

PRIOR ART DOCUMENTS

Patent Documents

Patent Document 1: International Publication No. WO 2005/070917
Patent Document 2: Japanese Unexamined Patent Publication No. 2007-1944
Patent Document 3: International Publication No. WO 2007/011022
Patent Document 4: Japanese Unexamined Patent Publication No. 2007-217353
Patent Document 5: Japanese Unexamined Patent Publication No. 2010-6746

DISCLOSURE OF THE INVENTION

Problems to be Solved by the Invention

As a result of examining combinations of quinoline compounds represented by general formula (I) and other fungicidal components, the inventors of the present invention found that, by combining a quinoline compound represented by general formula (I) with a specific fungicidal compound, superior control effects (synergistic effects) are obtained against various plant pathogens that could not have been predicted from the individual components alone, stable preventive effects are demonstrated against organisms resistant to existing chemical agents, and the occurrence of chemical damage is not observed, thereby leading to completion of the present invention.

An object of the present invention is to provide a novel plant disease control composition, and method for controlling plant disease by applying that composition, that exhibits a plurality of disease spectra against various types of plant pathogens, demonstrates high plant disease control effects against organisms resistant to existing chemical agents, demonstrates a high level of activity even if the amount of active ingredient administered in a pathogen-rich environment is reduced, and is observed to be free of the occurrence of phytotoxicity.

Means for Solving the Problems

The present invention is a plant disease control composition comprising as active ingredients thereof:
(a) at least one quinoline compound represented by general formula (I) or a salt thereof (group a):

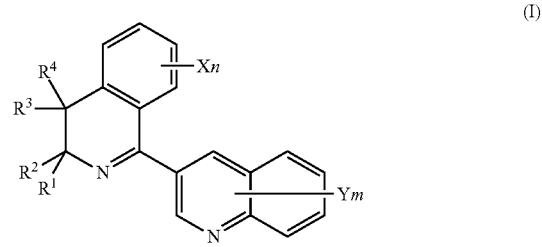

wherein,
$R^1$ and $R^2$ may be the same or different and represent a methyl group, ethyl group, propyl group, trifluoromethyl group, trifluoroethyl group, phenyl group, fluorophenyl group or chlorophenyl group,
$R^3$ and $R^4$ may be the same or different and represent a hydrogen atom, fluorine atom or methyl group,
X represents a fluorine atom, chlorine atom, bromine atom, methyl group, ethynyl group, furyl group, thienyl group, cyano group, methoxyethanimidoyl group, ethoxyethanimidoyl group or phenoxyethanimidoyl group and n is 0, 1 or 2, and
Y represents a fluorine atom or methyl group and m is 0 or 1; and one or more fungicidal compounds selected from: pyrazole carboxamides consisting of (b-1) Fluxapyroxad,
(b-2) Benzovindiflupyr,
(b-3) a compound of formula (II)

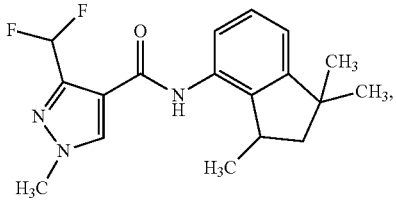

(II)

(b-4) Bixafen,
(b-5) Penflufen,
(b-6) Sedaxane,
(b-7) Isopyrazam,
(b-8) a compound of formula (III)

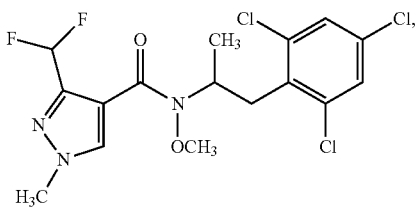

(III)

and
(b-9) a compound of formula (IV)

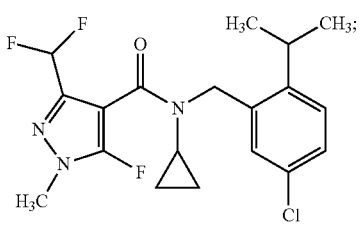

(IV)

methoxyacrylates consisting of
(b-10) Enoxastrobin,
(b-11) Pyraoxystrobin,
(b-12) Coumoxystrobin,
(b-13) Coumethoxystrobin,
(b-14) Flufenoxystrobin,
(b-15) Pyriminostrobin, and
(b-16) Picoxystrobin;
methoxycarbamates consisting of
(b-17) Pyrametostrobin,
(b-18) Triclopyricarb, and
(b-19) Pyraclostrobin;
azole compounds consisting of
(b-20) Imazalil,
(b-21) Prochloraz,
(b-22) Tetraconazole,
(b-23) Prothioconazole,
(b-24) Epoxiconazole,
(b-25) Ipconazole,
(b-26) Metconazole,
(b-27) Propiconazole,
(b-28) Cyproconazole,
(b-29) Difenoconazole,
(b-30) Fluquinconazole,
(b-31) Flusilazole,
(b-32) Penconazole,
(b-33) Triadimenol,
(b-34) Flutriafol,
(b-35) Myclobutanil,
(b-36) compounds of general formula (V)

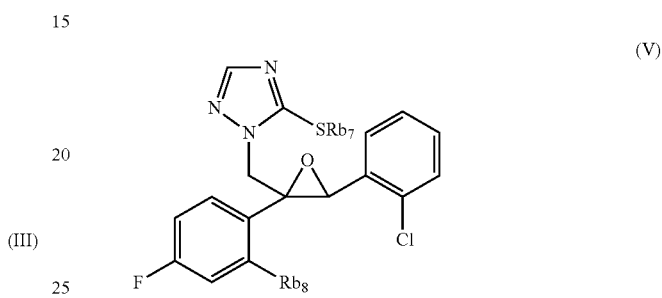

(V)

wherein $Rb_7$ represents a hydrogen atom, alkyl group, allyl group, benzyl group, amino group, cyano group or a valency that forms a double bond between a sulfur atom and a triazole ring to generate a ring represented by:

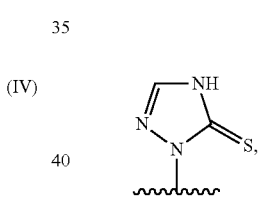

and
$Rb_8$ represents a hydrogen atom or fluorine atom,
(b-37) compounds of general formula (VI)

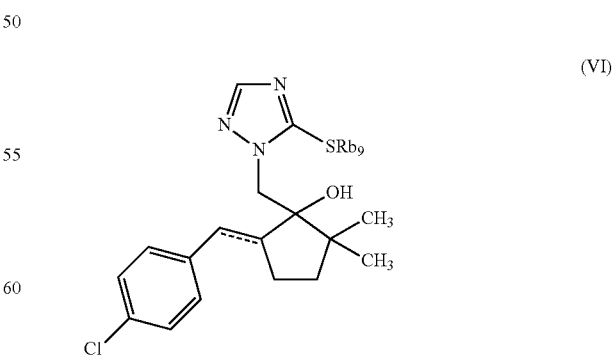

(VI)

wherein the broken line indicates the presence or absence of a bond, and $Rb_9$ represents a hydrogen atom, alkyl group, allyl group, benzyl group or cyano group, and (b-38) compounds of general formula (VII)

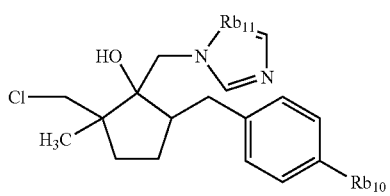

wherein $Rb_{10}$ represents a halogen atom and $Rb_{11}$ represents a nitrogen atom or methine group;
amide compounds consisting of
(b-39) Zoxamide,
(b-40) Fluopicolide,
(b-41) Carboxin,
(b-42) Thifluzamide,
(b-43) Fluopyram,
(b-44) Mandipropamid,
(b-45) Tiadinil,
(b-46) Isotianil,
(b-47) Isofetamid,
(b-48) Valifenalate,
(b-49) Pyraziflumid,

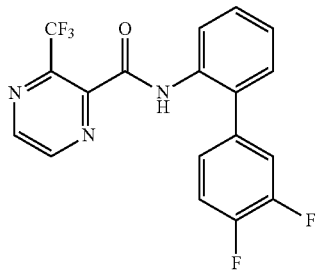

and
(b-50) Iprovalicarb;
strobilurin compounds consisting of
(b-51) Fluoxastrobin,
(b-52) Dimoxystrobin,
(b-53) Orysastrobin,
(b-54) Metominostrobin,
(b-55) Trifloxystrobin,
(b-56) Mandestrobin, and
(b-57) Fenaminostrobin;
benzimidazole compounds consisting of
(b-58) Benomyl,
(b-59) Carbendazim, and
(b-60) Thiabendazole;
pyrimidine compounds consisting of
(b-61) Cyprodinil, and
(b-62) Pyrimethanil;
quinolone compounds consisting of
(b-63) Quinoxyfen, and
(b-64) Tebufloquin;
morpholine compounds consisting of
(b-65) Fenpropimorph, and
(b-66) Tridemorph;
organosulfur compounds consisting of
(b-67) Metiram,
(b-68) Thiuram,
(b-69) Propineb, (b-70) Folpet,
(b-71) Isoprothiolane,
(b-72) Acibenzolar-S-methyl,
(b-73) Probenazole, and
(b-74) Chinomethionat;
anilide compounds consisting of
(b-75) Benalaxyl-M,
(b-76) Pencycuron, and
(b-77) Flutianil;
aminopyridine compounds consisting of
(b-78) Picarbutrazox, and
(b-79) compounds of general formula (VIII)

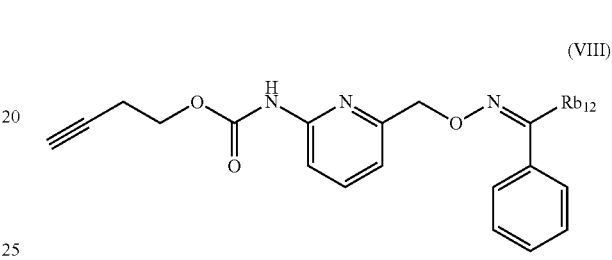

wherein $Rb_{12}$ represents

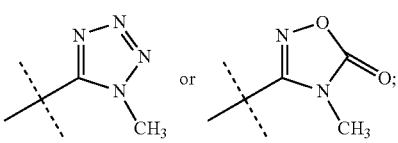

dithiine compounds consisting of
(b-80)

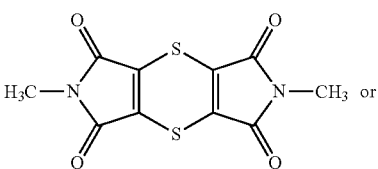

and
(b-81) Dithianon;
phenylketone compounds consisting of
(b-82) Metrafenone, and
(b-83) Pyriofenone;

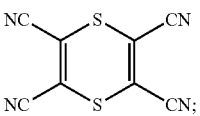

other fungicidal compounds (i) consisting of
(b-84) Oxathiapiprolin,
(b-85) compounds of general formula (XI)

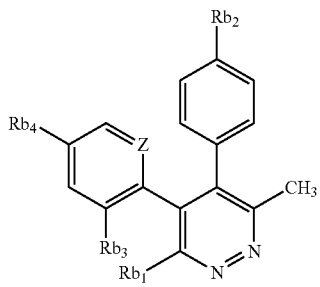

wherein $Rb_1$ represents a chlorine atom, bromine atom, cyano group, methyl group or methoxy group, $Rb_2$ represents a fluorine atom or hydrogen atom, $Rb_3$ represents a halogen atom, $Rb_4$ represents a halogen atom, methoxy group or hydrogen atom and Z represents N or C—F, (b-86) compounds of general formula (XII)

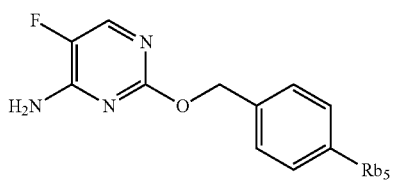

wherein $Rb_5$ represents a methyl group or fluorine atom, (b-87) compounds of general formula (XIII)

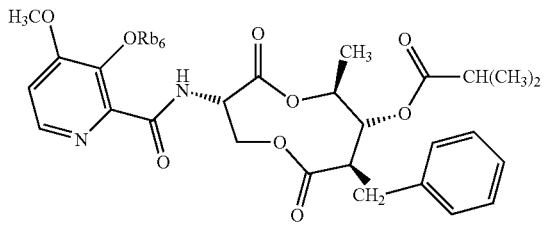

wherein $Rb_6$ represents —$CH_2OC(O)CH(CH_3)_2$, —$C(O)CH_3$, —$CH_2OC(O)CH_3$, —$C(O)OCH_2CH(CH_3)_2$ or

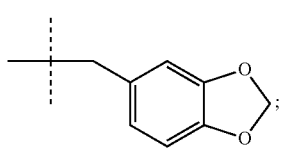

(b-88) a compound of formula (XIV)

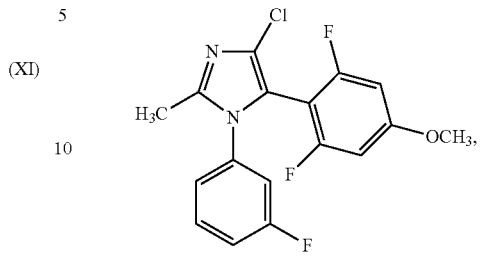

(b-89) compounds of general formula (XV)

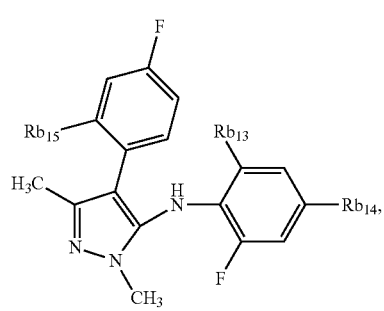

wherein $Rb_{13}$ represents a chlorine atom or fluorine atom, $Rb_{14}$ represents a chlorine atom or hydrogen atom and $Rb_{15}$ represents a chlorine atom or bromine atom, (b-90) compounds of general formula (XVI)

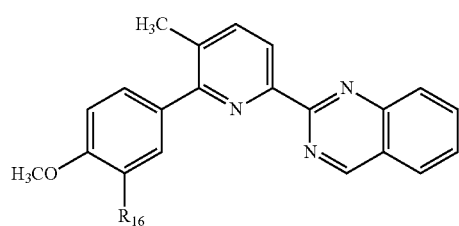

wherein $Rb_{16}$ represents a fluorine atom or methyl group;
other fungicidal compounds (ii) consisting of
(b-91) a compound of formula (XVII)

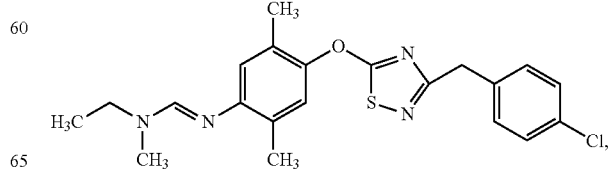

(b-92) a compound of formula (XVIII)

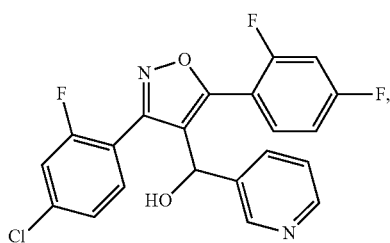

(XVIII)

(b-93) D-tagatose,
(b-94) compounds of general formula (XIX)

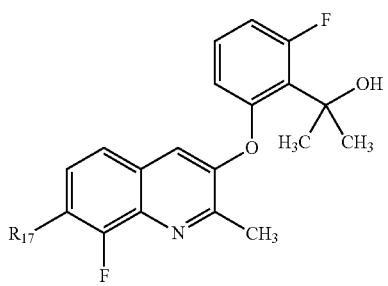

(XIX)

wherein $Rb_{17}$ represents a hydrogen atom or fluorine atom;

other fungicidal compounds (iii) consisting of
(b-95) Ametoctradin,
(b-96) Sulfur;
(b-97) Amisulbrom,
(b-98) Pyribencarb,
(b-99) Fenpyrazamine,
(b-100) Proquinazid,
(b-101) Spiroxamine,
(b-102) Fenpropidin,
(b-103) Pyrisoxazole,
(b-104) Pyroquilon,
(b-105) Phosphorous acid, and
(b-106) Hydroxyisoxazole (Hymexazol).

Furthermore, in the quinoline compounds represented by general formula (I), Ym represents a hydrogen atom when m is 0 and Xn represents a hydrogen atom when n is 0.

Effects of the Invention

The plant disease control composition of the present invention has a plurality of disease spectra against various plant pathogens, including fungicide-resistant organisms (such as *Pyricularia oryzae* that causes rice blast or *Botrytis cinerea* that causes gray mold in tomatoes, cucumbers and green beans), and demonstrates superior control effects (synergistic control effects) that could not have been predicted from the individual components alone. In addition, the plant disease control composition of the present invention exhibits a high level of plant disease control effects even against organisms resistant to existing chemical agents and is also observed to be free of the occurrence of phytotoxicity.

BEST MODE FOR CARRYING OUT THE INVENTION

Each of the terms used for the quinoline compounds represented by general formula (I) in the scope of claim for patent and description of the present application are in accordance with definitions commonly used in the field of chemistry as well as the definitions described in International Publication No. WO 2005/070917, Japanese Unexamined Patent Publication No. 2007-1944, International Publication No. WO 2007/011022 and Japanese Unexamined Patent Publication No. 2007-217353.

The quinoline compound represented by general formula (I) in the present invention can be in the form of a salt in the manner of a salt of an inorganic acid such as a hydrochloride, sulfate or nitrate, in the form of a phosphate, in the form of a sulfonate such as a methanesulfonate, ethanesulfonate, benzenesulfonate or p-toluenesulfonate, or in the form of a salt of an organic carboxylic acid such as an acetate, benzoate, oxalate, fumarate or salicylate (and preferably in the form of a hydrochloride, sulfate, nitrate, methanesulfonate, oxalate, fumarate or salicylate).

The quinoline compound represented by general formula (I) of the present invention and salts thereof can also be in the form of a solvate, and these solvates are also included in the present invention. The solvate is preferably a hydrate.

Some quinoline compounds represented by general formula (I) in the present invention are compounds that have an asymmetric carbon, and in such cases, the invention of the present application also includes compounds having one type of optically active form as well as mixtures containing a plurality of optically active forms at an arbitrary ratio.

The quinoline compound represented by general formula (I) in the present invention is preferably:
(a-1) 3-(5-fluoro-3,3-dimethyl-3,4-dihydroisoquinolin-1-yl)quinoline,
(a-2) 3-(5-chloro-3,3-dimethyl-3,4-dihydroisoquinolin-1-yl)quinoline,
(a-3) 3-(5-bromo-3,3-dimethyl-3,4-dihydroisoquinolin-1-yl)quinoline,
(a-4) 3-(5-ethynyl-3,3-dimethyl-3,4-dihydroisoquinolin-1-yl)quinoline,
(a-5) 3-(5,6-difluoro-3,3-dimethyl-3,4-dihydroisoquinolin-1-yl)quinoline
(a-6) 3-(3-ethyl-5-fluoro-3-propyl-3,4-dihydroisoquinolin-1-yl)quinoline
(a-7) 3-(5-fluoro-3-methyl-3-propyl-3,4-dihydroisoquinolin-1-yl)quinoline
(a-8) 3-(3-methyl-3-trifluoromethyl-3,4-dihydroisoquinolin-1-yl)quinoline
(a-9) 3-[3-methyl-3-(2,2,2-trifluoroethyl)-3,4-dihydroisoquinolin-1-yl]quinoline
(a-10) 3-[3-methyl-3-phenyl-3,4-dihydroisoquinolin-1-yl]quinoline
(a-11) 3-[3-methyl-3-(4-fluorophenyl)-3,4-dihydroisoquinolin-1-yl]quinoline
(a-12) 3-[3-methyl-3-(4-chlorophenyl)-3,4-dihydroisoquinolin-1-yl]quinoline
(a-13) 3-(3,3,4,4-tetramethyl-3,4-dihydroisoquinolin-1-yl)quinoline
(a-14) 3-(5-fluoro-3,3,4,4-tetramethyl-3,4-dihydroisoquinolin-1-yl)quinoline
(a-15) 3-(5-fluoro-3,3,4,4-tetramethyl-3,4-dihydroisoquinolin-1-yl)-6-fluoroquinoline (a-16) 3-(5-fluoro-3,3,4,4-tetramethyl-3,4-dihydroisoquinolin-1-yl)-8-fluoroquinoline
(a-17) 3-(5-fluoro-3,3,4,4-tetramethyl-3,4-dihydroisoquinolin-1-yl)-8-methyl quinoline
(a-18) 3-(4,4-difluoro-3,3-dimethyl-3,4-dihydroisoquinolin-1-yl)quinoline
(a-19) 3-(4,5-difluoro-3,3-dimethyl-3,4-dihydroisoquinolin-1-yl)quinoline,
(a-20) 3-(4,4,5-trifluoro-3,3-dimethyl-3,4-dihydroisoquinolin-1-yl)quinoline, or
a salt thereof.

In more preferable embodiment of the present invention, the quinolone compound represented by general formula (I) is selected from the group consisting of:
(a-14) 3-(5-fluoro-3,3,4,4-tetramethyl-3,4-dihydroisoquinolin-1-yl)quinoline
(a-18) 3-(4,4-difluoro-3,3-dimethyl-3,4-dihydroisoquinolin-1-yl)quinolone,
(a-20) 3-(4,4,5-trifluoro-3,3-dimethyl-3,4-dihydroisoquinolin-1-yl)quinoline, and a salt thereof.

Quinoline compounds represented by general formula (I) in the present invention (group a compounds) are known compounds, and are produced according to, for example, the method described in International Publication No. WO 2005/070917, or methods complying therewith.

The fungicidal compound contained with at least one quinoline compound represented by general formula (I) or a salt thereof in the present invention (group a) is preferably selected from:

pyrazole carboxamides consisting of
(b-1) Fluxapyroxad,
(b-2) Benzovindiflupyr,
(b-3) a compound of formula (II)

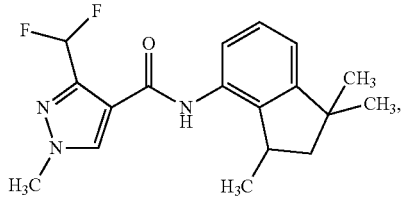

(b-4) Bixafen,
(b-5) Penflufen,
(b-6) Sedaxane,
(b-7) Isopyrazam,
(b-8) a compound of formula (III)

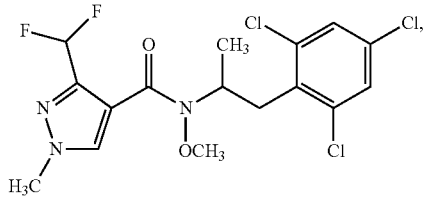

and
(b-9) a compound of formula (IV)

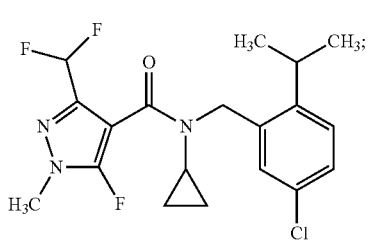

methoxyacrylates consisting of
(b-16) Picoxystrobin;
methoxycarbamates consisting of
(b-19) Pyraclostrobin;
azole compounds consisting of
(b-20) Imazalil,
(b-21) Prochloraz,
(b-22) Tetraconazole,
(b-23) Prothioconazole,
(b-24) Epoxiconazole,
(b-25) Ipconazole,
(b-26) Metconazole,
(b-27) Propiconazole,
(b-28) Cyproconazole,
(b-29) Difenoconazole,
(b-30) Fluquinconazole,
(b-31) Flusilazole,
(b-32) Penconazole,
(b-33) Triadimenol,
(b-34) Flutriafol,
(b-35) Myclobutanil,
(b-36) compounds of general formula (V)

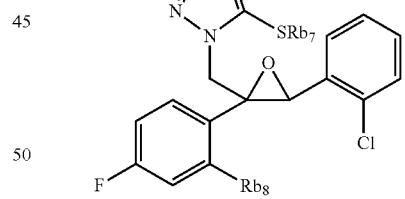

wherein $Rb_7$ represents a hydrogen atom, alkyl group, allyl group, benzyl group, amino croup, cyano group or a valency that forms a double bond between a sulfur atom and a triazole ring to generate a ring represented by:

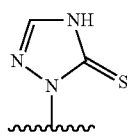 [SMILES: *n1nc[nH]c1=S]

and

Rb$_8$ represents a hydrogen atom or fluorine atom, and (b-38) compounds of general formula (VII)

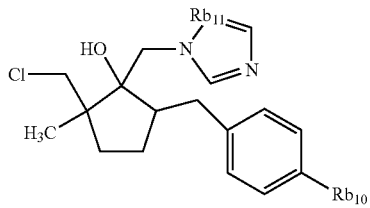
(VII)

wherein Rb$_{10}$ represents a halogen atom and Rb$_{11}$ represents a nitrogen atom or methine group;

amide compounds consisting of
(b-39) Zoxamide,
(b-40) Fluopicolide,
(b-41) Carboxin,
(b-42) Thifluzamide,
(b-43) Fluopyram,
(b-44) Mandipropamid,
(b-45) Tiadinil,
(b-46) Isotianil,
(b-47) Isofetamid,
(b-49) Pyraziflumid,

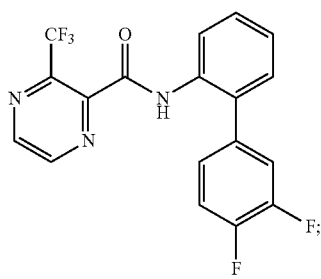 [SMILES: O=C(Nc1ccccc1-c1ccc(F)c(F)c1)c1nccnc1C(F)(F)F]

and
(b-50) Iprovalicarb;
strobilurin compounds consisting of
(b-51) Fluoxastrobin,
(b-52) Dimoxystrobin,
(b-53) Orysastrobin,
(b-54) Metominostrobin, and
(b-55) Trifloxystrobin;
benzimidazole compounds consisting of
(b-58) Benomyl,
(b-59) Carbendazim, and
(b-60) Thiabendazole;
pyrimidine compounds consisting of
(b-61) Cyprodinil, and
(b-62) Pyrimethanil;
quinolone compounds consisting of
(b-63) Quinoxyfen, and
(b-64) Tebufloquin;
morpholine compounds consisting of
(b-65) Fenpropimorph, and
(b-66) Tridemorph;

organosulfur compounds consisting of
(b-67) Metiram,
(b-68) Thiuram,
(b-69) Propineb,
(b-70) Folpet,
(b-71) Isoprothiolane,
(b-72) Acibenzolar-S-methyl,
(b-73) Probenazole, and
(b-74) Chinomethionat;
anilide compounds consisting of
(b-75) Benalaxyl-M,
(b-76) Pencycuron, and
(b-77) Flutianil;
an aminopyridine compound consisting of
(b-78) Picarbutrazox;
a dithiine compound consisting of
(b-81) Dithianon;
phenylketone compounds consisting of
(b-82) Metrafenone, and
(b-83) Pyriofenone;
other fungicidal compounds (i) consisting of
(b-84) Oxathiapiprolin
(b-85) compounds of general formula (XI)

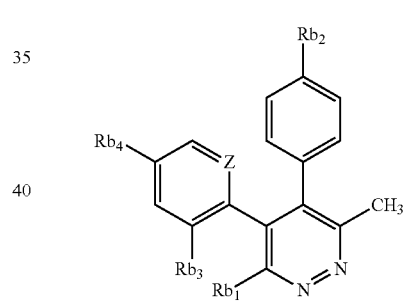
(XI)

wherein Rb$_1$ represents a chlorine atom, bromine atom, cyano group, methyl group or methoxy group, Rb$_2$ represents a fluorine atom or hydrogen atom, Rb$_3$ represents a halogen atom, Rb$_4$ represents a halogen atom, methoxy group or hydrogen atom and Z represents N or C—F, (b-88) a compound of formula (XIV)

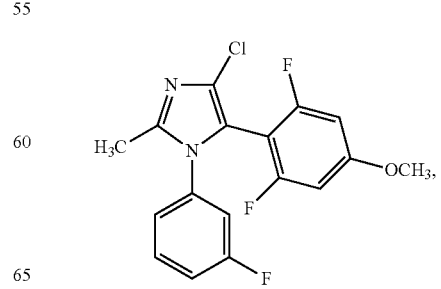
(XIV)

(b-89) compounds of general formula (XV)

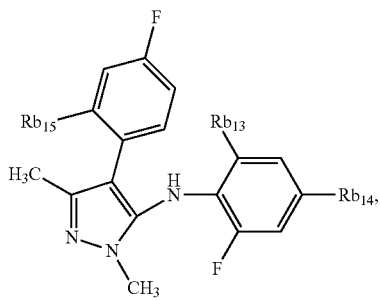

(XV)

wherein Rb$_{13}$ represents a chlorine atom or fluorine atom, Rb$_{14}$ represents a chlorine atom or hydrogen atom and Rb$_{15}$ represents a chlorine atom or bromine atom,
other fungicidal compounds (ii) consisting of:
(b-91) a compound of formula (XVII)

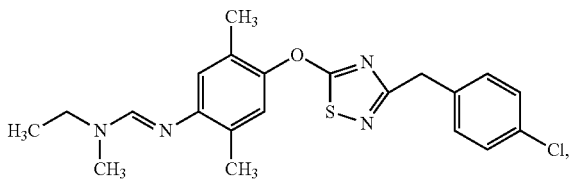

(XVII)

(b-92) a compound of formula (XVIII)

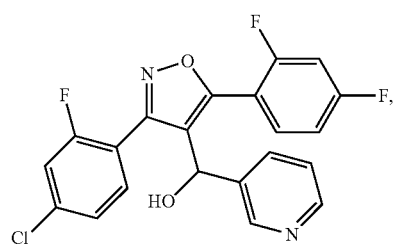

(XVIII)

(b-93) D-tagatose, and
(b-94) compounds of general formula (XIX)

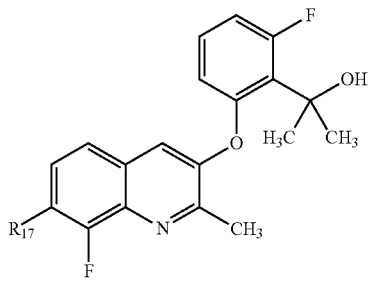

(XIX)

wherein Rb$_{17}$ represents a hydrogen atom or fluorine atom;
other fungicidal compounds (iii) consisting of:
(b-95) Ametoctradin,
(b-96) Sulfur;
(b-97) Amisulbrom,
(b-98) Pyribencarb,
(b-99) Fenpyrazamine,
(b-100) Proquinazid,
(b-101) Spiroxamine,
(b-102) Fenpropidin,
(b-103) Pyrisoxazole,
(b-104) Pyroquilon,
(b-105) Phosphorous acid, and
(b-106) Hydroxyisoxazole (Hymexazol),
and more preferably selected from:
pyrazole carboxamides consisting of
(b-1) Fluxapyroxad,
(b-2) Benzovindiflupyr,
(b-3) a compound of formula (II)

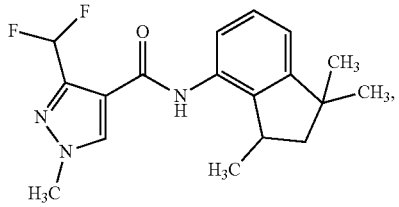

(II)

(b-8) a compound of formula (III)

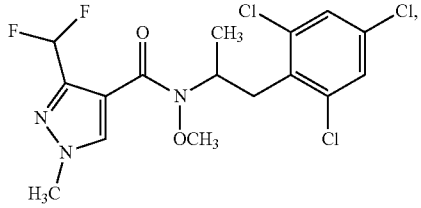

(III)

and
(b-9) a compound of formula (IV)

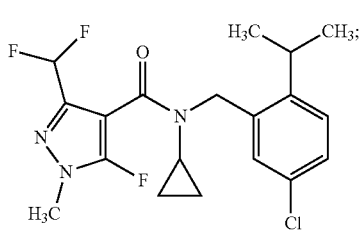

(IV)

azole compounds consisting of
(b-36) compounds of general formula (V)

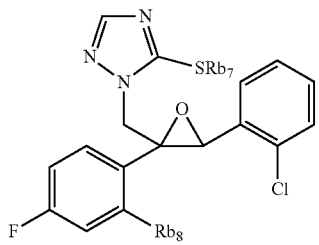

(V)

wherein Rb₇ represents a hydrogen atom, alkyl group, allyl group, benzyl group, amino group, cyano group or a valency that forms a double bond between a sulfur atom and a triazole ring to generate a ring represented by:

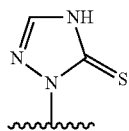

and

Rb₈ represents a hydrogen atom or fluorine atom, and (b-38) compounds of general formula (VII)

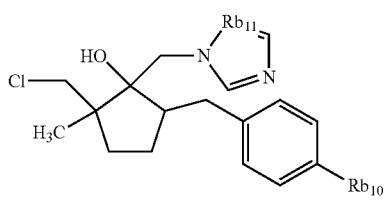

(VII)

wherein Rb₁₀ represents a halogen atom and Rb₁₁ represents a nitrogen atom or methine group;

amide compounds consisting of
(b-47) Isofetamid, and
(b-49) Pyraziflumid,

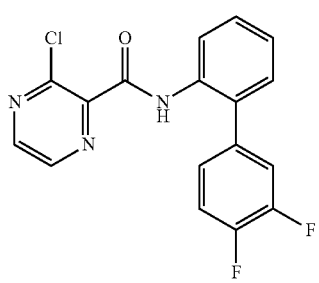 [SMILES: O=C(Nc1ccccc1-c1ccc(F)c(F)c1)c1nccnc1Cl]

and
an aminopyridine compound consisting of
(b-78) Picarbutrazox;
other fungicidal compounds (i) consisting of
(b-84) Oxathiapiprolin
(b-85) compounds of general formula (XI)

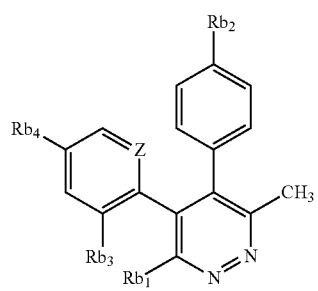

(XI)

wherein Rb₁ represents a chlorine atom, bromine atom, cyano group, methyl group or methoxy group, Rb₂ represents a fluorine atom or hydrogen atom, Rb₃ represents a halogen atom, Rb₄ represents a halogen atom, methoxy group or hydrogen atom and Z represents N or C—F, (b-88) a compound of formula (XIV)

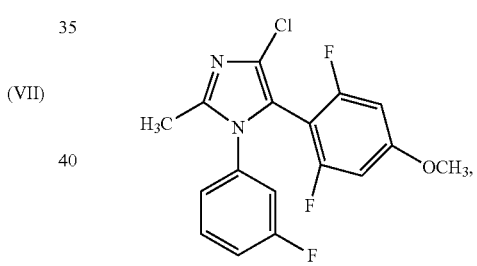

(XIV)

and
(b-89) compounds of general formula (XV)

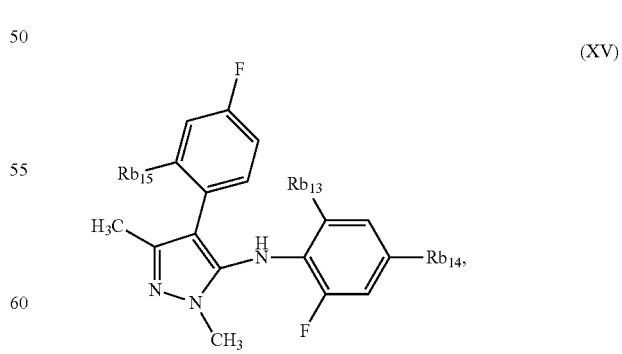

(XV)

wherein Rb₁₃ represents a chlorine atom or fluorine atom, Rb₁₄ represents a chlorine atom or hydrogen atom and Rb₁₅ represents a chlorine atom or bromine atom;

other fungicidal compounds (ii) consisting of
(b-91) a compound of formula (XVII)

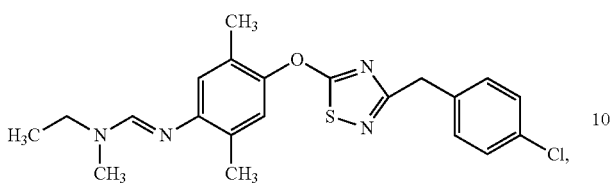

(b-92) a compound of formula (XVIII)

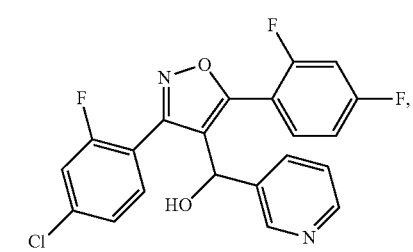

(b-93) D-tagatose,
(b-94) compounds of general formula (XIX)

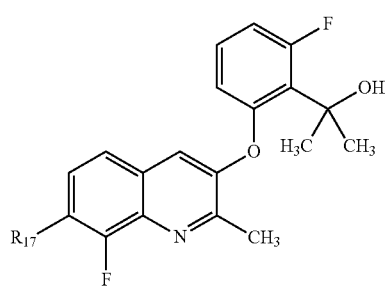

wherein $Rb_{17}$ represents a hydrogen atom or fluorine atom,
and still more preferably selected from:
pyrazole carboxamides consisting of
(b-1) Fluxapyroxad,
(b-2) Benzovindiflupyr, and
(b-3) a compound of formula (II)

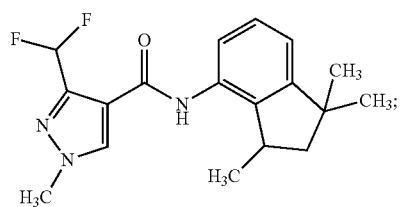

methoxyacrylates consisting of
(b-10) Enoxastrobin,
(b-11) Pyraoxystrobin,
(b-12) Coumoxystrobin,
(b-13) Coumethoxystrobin,
(b-14) Flufenoxystrobin, and
(b-15) Pyriminostrobin;
methoxycarbamates consisting of
(b-17) Pyrametostrobin, and
(b-18) Triclopyricarb;
(b-84) Oxathiapiprolin;
(b-56) Mandestrobin;
(b-47) Isofetamid;
(b-78) Picarbutrazox;
(b-57) Fenaminostrobin;
(b-48) Valifenalate;
(b-49) Pyraziflumid,

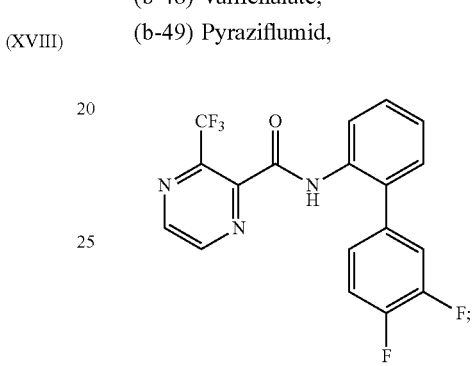

(b-85) compounds of general formula (XI)-1

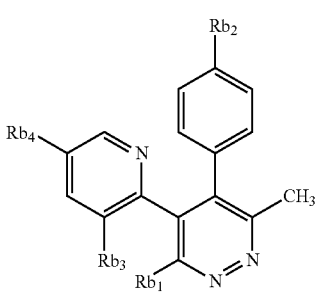

wherein $Rb_1$ represents a chlorine atom, bromine atom, cyano group, methyl group or methoxy group, $Rb_2$ represents a fluorine atom or hydrogen atom, $Rb_3$ represents a halogen atom, $Rb_4$ represents a halogen atom, methoxy group or hydrogen atom;
(b-86) compounds of general formula (XII)

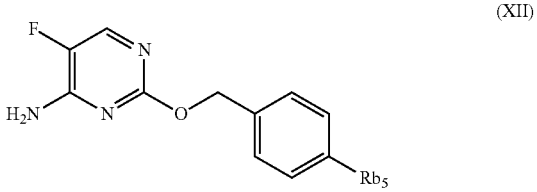

wherein $Rb_5$ represents a methyl group or fluorine atom;
(b-87) compounds of general formula (XIII)

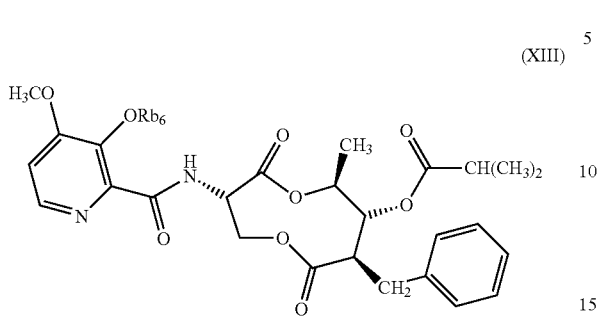

wherein $Rb_6$ represents —$CH_2OC(O)CH(CH_3)_2$, —$C(O)CH_3$, —$CH_2OC(O)CH_3$, —$C(O)OCH_2CH(CH_3)_2$ or

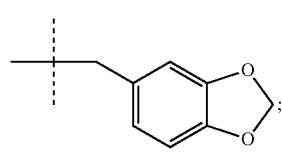

(b-88) a compound of formula (XIV)

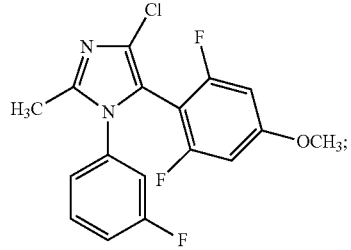

(b-89) a compound of formula (XV)-1

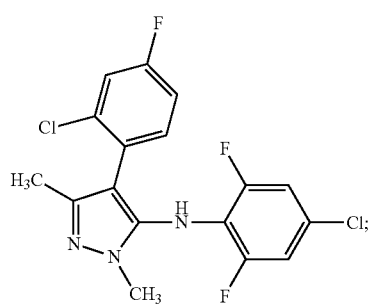

(b-80)

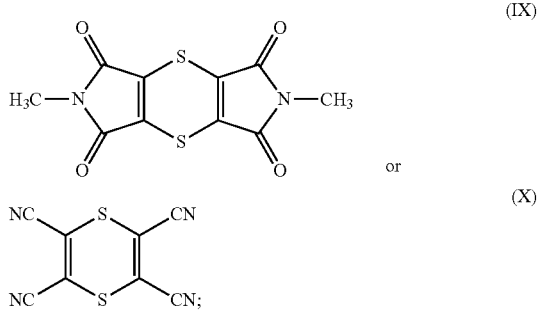

and
(b-90) a compound of formula (XVI)-1

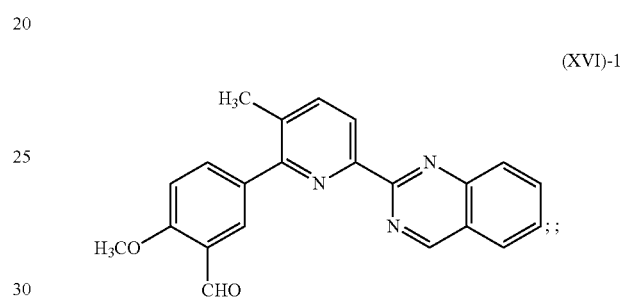

(b-36) compounds of general formula (V)

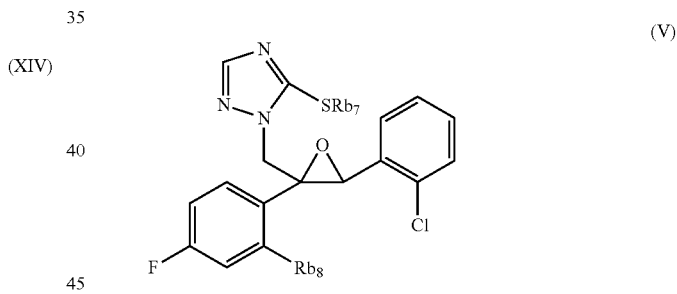

wherein $Rb_7$ represents a hydrogen atom, alkyl group, amino group or cyano group, and $Rb_8$ represents a hydrogen atom or fluorine atom;
(b-37') compounds of general formula (VI')

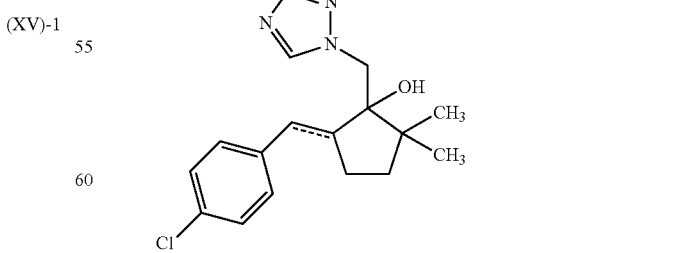

wherein the broken line indicates the presence or absence of a bond, and $Rb_9$ represents a hydrogen atom, alkyl group, amino group or cyano group;

(b-38) compounds of general formula (VII)

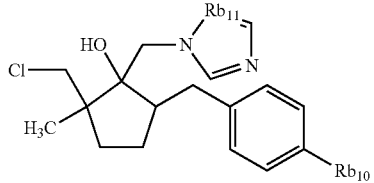

wherein $Rb_{10}$ represents a halogen atom and $Rb_{11}$ represents a nitrogen atom or methine group; and (b-79) compounds of general formula (VIII)

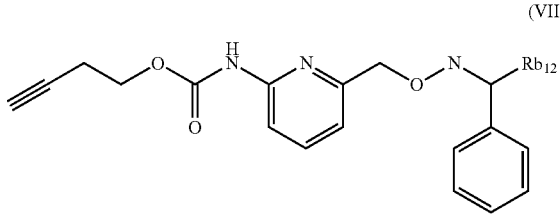

wherein $Rb_{12}$ represents

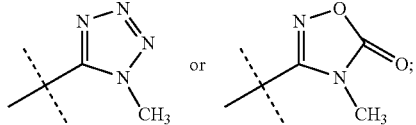

and further more preferably selected from:
pyrazole carboxamides consisting of
(b-1) Fluxapyroxad,
(b-2) Benzovindiflupyr, and
(b-3) a compound of formula (II)

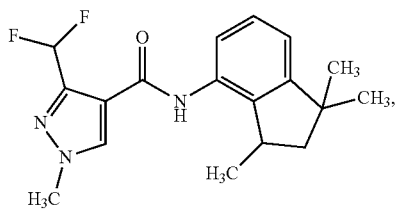

(b-47) Isofetamid;
(b-78) Picarbutrazox;
(b-49) Pyraziflumid,

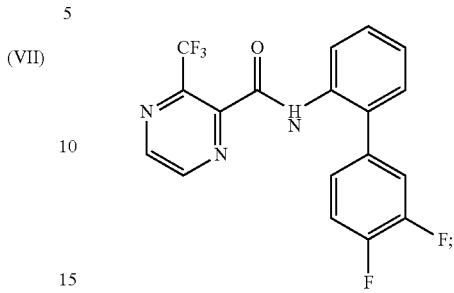

(b-85) compounds of general formula (XI)-1

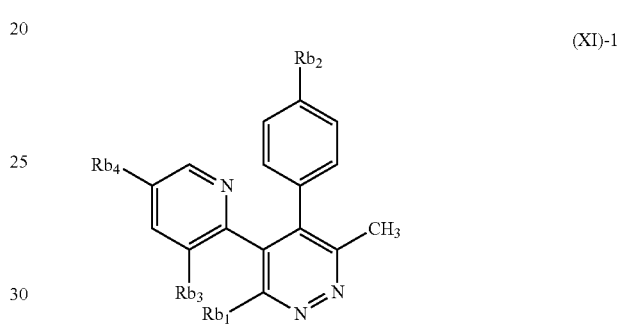

wherein $Rb_1$ represents a chlorine atom, bromine atom, cyano group, methyl group or methoxy group, $Rb_2$ represents a fluorine atom or hydrogen atom, $Rb_3$ represents a halogen atom, and $Rb_4$ represents a halogen atom, methoxy group or hydrogen atom;

(b-88) a compound of formula (XIV)

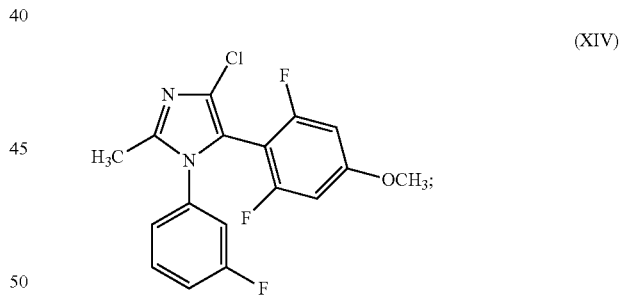

(b-89) a compound of formula (XV)-1

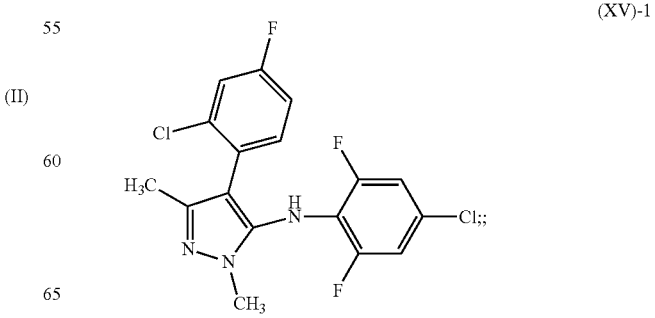

(b-36) compounds of general formula (V)

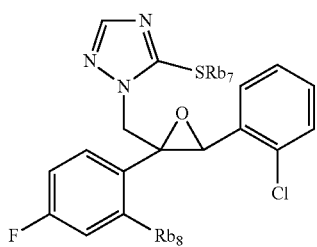

wherein Rb$_7$ represents a hydrogen atom, alkyl group, amino group or cyano group, and Rb$_8$ represents a hydrogen atom or fluorine atom;

(b-37') compounds of general formula (VI')

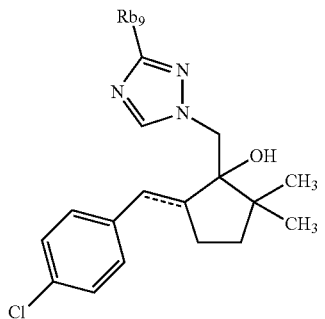

wherein the broken line indicates the presence or absence of a bond, and Rb$_9$ represents a hydrogen atom, alkyl group, amino group or cyano group;

(b-38) compounds of general formula (VII)

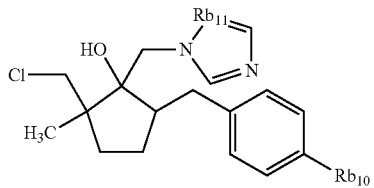

wherein Rb$_{10}$ represents a halogen atom and Rb$_{11}$ represents a nitrogen atom or methine group; and (b-79) compounds of general formula (VIII)

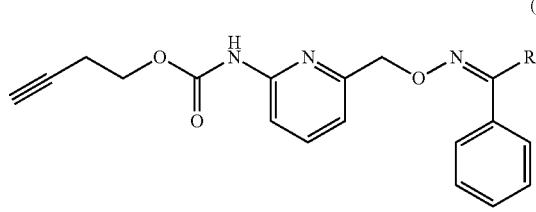

wherein Rb$_{12}$ represents

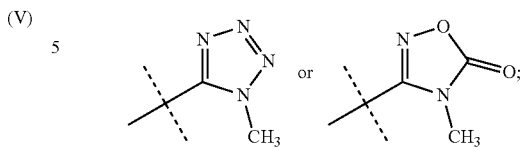

and most preferably selected from:
pyrazole carboxamides consisting of
(b-1) Fluxapyroxad,
(b-2) Benzovindiflupyr, and
(b-3) a compound of formula (II)

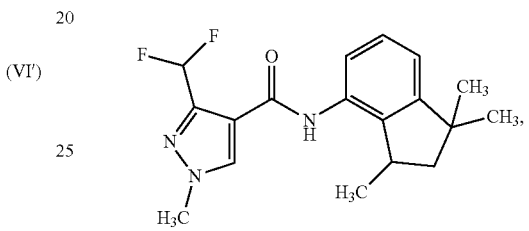

(b-47) Isofetamid;
(b-78) Picarbutrazox;
(b-49) Pyraziflumid,

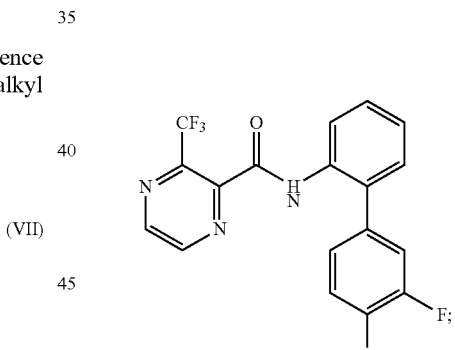

(b-88) a compound of formula (XIV)

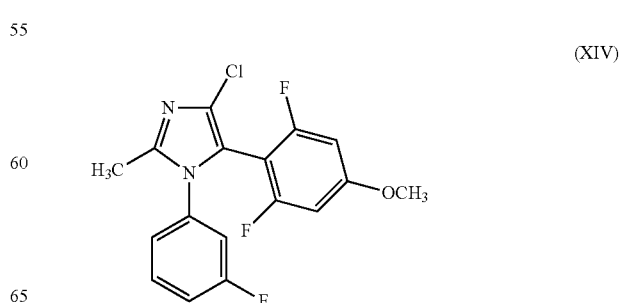

and (b-38) compounds of general formula (VII)

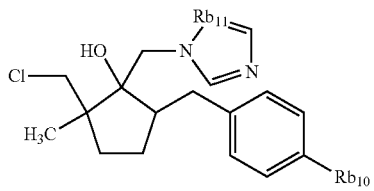

(VII)

wherein $Rb_{10}$ represents a halogen atom and $Rb_{11}$ represents a nitrogen atom or methine group.

In any one of the preferable embodiments described above, the compound (b-36) represented by general formula (V):

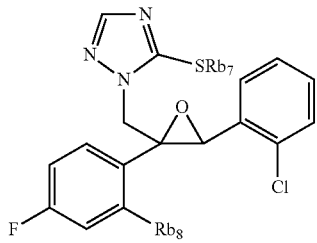

(V)

is preferably a compound wherein $Rb_7$ represents a valency that forms a double bond between a sulfur atom and a triazole ring to generate a moiety represented by:

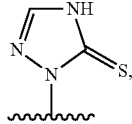

and $Rb_8$ represents a fluorine atom, that is, a compound represented by formula:

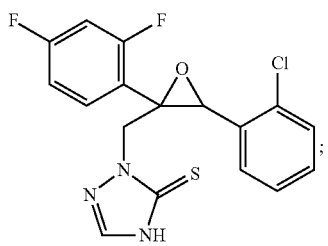

(V)-1

Further, in any one of the preferable embodiments described above, the compound (b-38) represented by general formula (VII):

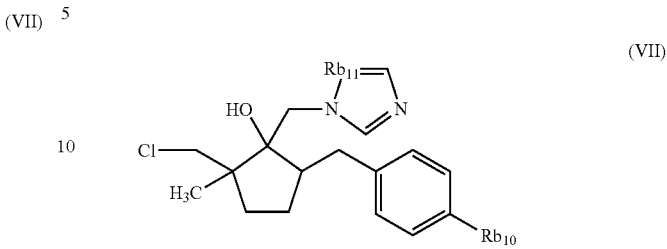

(VII)

is preferably a compound wherein $Rb_{10}$ is a chlorine atom, and $Rb_{11}$ is a nitrogen atom.

Further, in any one of the preferable embodiments described above, the compound (b-86) represented by general formula (XII):

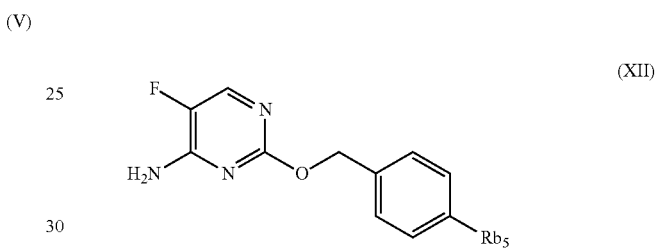

(XII)

is preferably a compound wherein $Rb_5$ is a methyl group.

Further, in any one of the preferable embodiments described above, the compound (b-85) represented by general formula (XI):

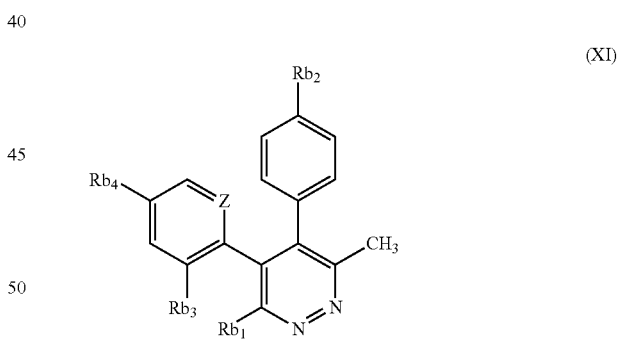

(XI)

is preferably a compound represented by:

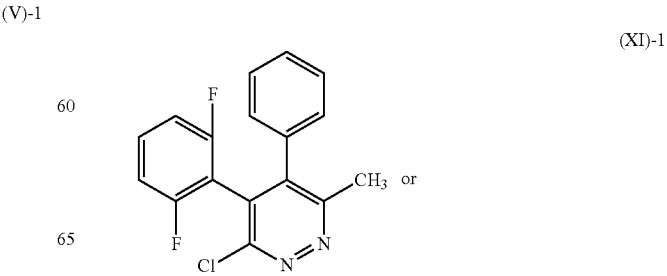

(XI)-1

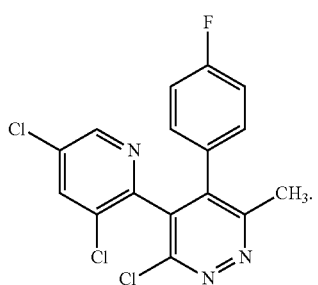

(XI)-2

Further, in any one of the preferable embodiments described above, the compound (b-87) represented by general formula (XIII)

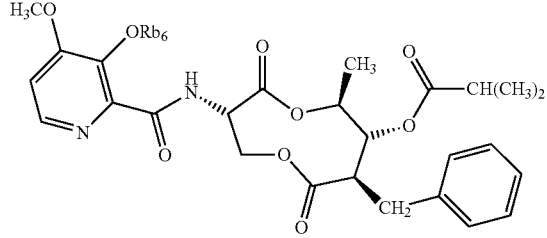

(XIII)

is preferably a compound wherein $Rb_6$ is —$CH_2OC(O)CH(CH_3)_2$.

Further, in any one of the preferable embodiments described above, the compound (b-89) represented by general formula (XV)

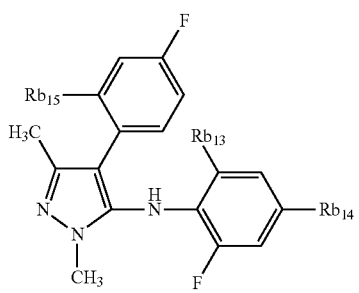

(XV)

is preferably a compound represented by:

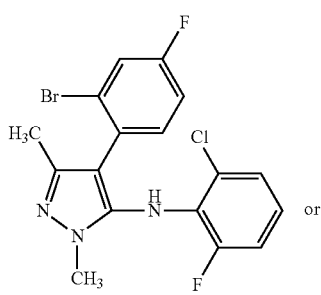

(XV)-1 or

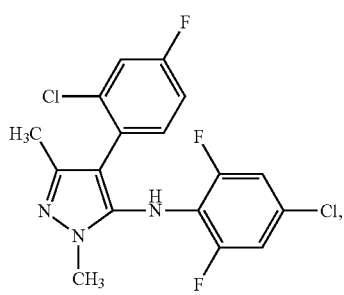

(XV)-2 and more preferably a compound represented by:

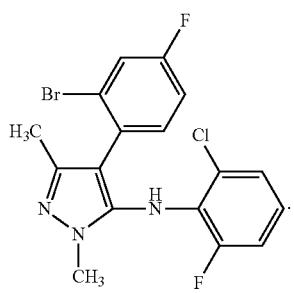

(XV)-1

Further, in any one of the preferable embodiments described above, the compound (b-90) represented by general formula (XVI):

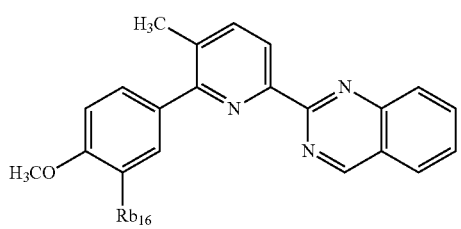

(XVI)

is preferably a compound wherein $Rb_{16}$ is a fluorine atom.

Further, in any one of the preferable embodiments described above, the compound (b-94) represented by general formula (XIX)

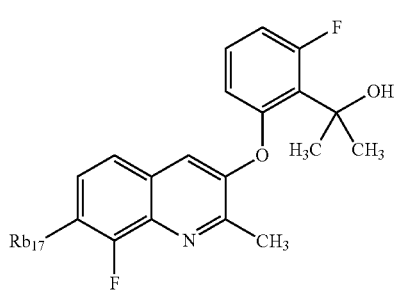

(XIX)

is preferably a compound wherein $Rb_{17}$ represents a fluorine atom.

In one embodiment of the present invention, the fungicidal compounds used in combination with at least one quinoline compound represented by general formula (I) or a salt thereof is preferably selected from the group consisting of:

(b-4) Bixafen,
(b-19) Pyraclostrobin,
(b-23) Prothioconazole,
(b-26) Metconazole,
(b-29) Difenoconazole,
(b-33) Triadimenol,
(b-43) Fluopyram,
(b-46) Isotianil,
(b-52) Dimoxystrobin,
(b-54) Metominostrobin,
(b-55) Trifloxystrobin,
(b-62) Pyrimethanil,
(b-69) Propineb,
(b-81) Dithianon,
(b-101) Spiroxamine and
(b-105) Phosphorous acid.

The compounds of group b are known compounds that are produced according to, for example, the methods described in International Publication No. WO 2008/145740, International Publication No. WO 2011/015416, International Publication No. WO 2011/085170, International Publication No. WO 1995/027693, International Publication No. WO 2006/016708, International Publication No. WO 2003/016303, International Publication No. WO 2006/125370, International Publication No. WO 2005/044813, International Publication No. WO 2007/000098, International Publication No. WO 2008/145052, International Publication No. WO 2002/006304, International Publication No. WO 2007/072999, International Publication No. WO 1986/002641, International Publication No. WO 2007/066601, International Publication No. WO 2009/094442, International Publication No. WO 2001/014339, International Publication No. WO 2011/056463, International Publication No. WO 2012/031061, International Publication No. WO 2010/043319, International Publication No. WO 2010/136475, International Publication No. WO 2010/146006, International Publication No. WO 2012/019981, International Publication No. WO 2010/149414, International Publication No. WO 2011/070771, International Publication No. WO 2012/172061, International Publication No. WO 2010/094728, International Publication No. WO 2013/037717, International Publication No. WO 2002/012172, European Patent Publication No. 936213, U.S. Pat. No. 7,666,884, or methods complying therewith.

The plant disease control composition of the present invention allows the obtaining of synergistic controlling effects in comparison with the case of using each of the active ingredients alone. The synergistic controlling effects and a degree thereof can be confirmed by using various test methods such as the method of Colby (see Colby SR, "Calculating Synergistic and Antagonistic Responses of Herbicide Combinations", Weed, 15, 1967, 20-22). This is currently a most efficacious method to determine a combination effect of two agents, and as described below in detail, during a comparison of a theoretical value calculated by Colby's formula with an actual measured effect (actual value), it is judged to be synergistic when the actual value is greater than the theoretical value, whereas to be antagonistic when the theoretical value is greater than the actual value. In the case the difference between an actual value and a theoretical value is larger, the synergistic effect is presumed to be higher. Thus, as a preferable embodiment of the present invention, there is provided a plant disease control composition comprising a combination of effective ingredients that exhibit a difference between an actual value and a theoretical value, of 5% or more, more preferably 10% or more, and still more preferably 20% or more.

Although the plant disease control composition in the present invention may be used as is, it is normally used by mixing with a carrier, and is used by formulating into a wettable powder (WP), suspension concentrate (SC), granule (GR), dustable powder (DP), soluble concentrate (SC), water dispersible granule (WG), or emulsion concentrate (EC) and the like at a suitable time according to commonly known methods by adding a formulation additive such as a dispersing agent, wetting agent, binder, thickener, preservative, colorant or stabilizer and the like as necessary. Other types of formulations known in the art are also applicable in the present invention. As used herein, the name of preparation (formulation) types and codes are essentially based on OECD Guidance Documents for Pesticide Registration (http://www.oecd.org/env/ehs/pesticides-biocides/oecdguidancedocumentsforpesticideregistration.htm). The content of the active ingredient in the form of the quinoline compound (I: group a compound) in these preparations is normally a weight ratio within the range of 0.005% to 99%, preferably within the range of 0.1% to 90% and even more preferably within the range of 0.3% to 80%. In addition, the content of the active ingredient in the form of the fungicidal compound of group b in these preparations is normally a weight ratio within the range of 0.005% to 99%, preferably within the range of 0.1% to 90% and even more preferably within the range of 0.3% to 80%. The total of the quinoline compound (I: group a compound) and the fungicidal compound of group b is normally a weight ratio within the range of 0.01% to 99%, preferably within the range of 0.1% to 90% and even more preferably within the range of 0.3% to 80%. The mixing ratio between the quinoline compound (I: group a compound) and the fungicidal compound of group b is normally a weight ratio of the fungicidal compound of group b to the quinoline compound 1 of 0.01 to 1000 and preferably a weight ratio of the fungicidal compound of group b to the quinoline compound 1 of 0.01 to 500, more preferably 1 of 0.01 to 100, still more preferably 1 of 0.01 to 50 and most preferably 1 of 0.01 to 25. Within this range, it would be easy to find a most preferable mixing ratio of actually combined individual compounds. It would also be possible to speculate a preferable mixing ratio of similar combinations in terms of a mode of action or chemical structure of the fungicidal compound of group b, based on the measured combinations having synergistic effects.

In the plant disease control composition of the present invention, although varying according to the preparation form, the combined content of active ingredients in the form of the quinoline compound (I: group a compound) and the fungicidal compound of group b is normally 0.01% to 30% by weight in the case of a dustable powder, 0.1% to 80% by weight in the case of a wettable powder, 0.5% to 20% by weight in the case of a granule, 2% to 50% by weight in the case of an emulsion concentrate, 1% to 50% by weight in the case of a suspension concentrate, and 1% to 80% by weight in the case of a water dispersible granule. It is preferably 0.05 to 10% by weight in the dustable powder, 5 to 60% by weight in the wettable powder, 5 to 20% by weight in the emulsion concentrate, 5 to 50% by weight in the suspension concentrate, and 5 to 50% by weight in the water dispersible granule. The content of additives is 0% to 80% by weight, and the content of the carrier is the amount obtained by subtracting the total content of active ingredient compounds and additives from 100% by weight.

The carrier used in the aforementioned composition refers to a synthetic or natural, inorganic or organic substance that is incorporated to aid in the delivery of active ingredients to a site to be treated or to facilitate storage, transport or handling of active ingredient compounds, can be used in the form of a solid or liquid provided it is used in ordinary agri-horticultural preparations, and there are no specific limitations thereon. Examples of solid carriers include inorganic substances such as bentonite, montmorillonite, kaolinite, diatomaceous earth, kaolin, talc, clay, vermiculite, gypsum, calcium carbonate, amorphous silica or ammonium sulfate, plant-based organic substances such as soybean powder, wood meal, sawdust, wheat flour, lactose, sucrose or glucose, and urea. Examples of liquid carriers include aromatic hydrocarbons and naphthenes such as toluene, xylene or cumene, paraffin-based hydrocarbons such as n-paraffin, iso-paraffin, liquid paraffin, kerosene, mineral oil or polybutene, ketones such as acetone or methyl ethyl ketone, ethers such as dioxane or diethylene glycol dimethyl ether, alcohols such as ethanol, propanol or ethylene glycol, carbonates such as ethylene carbonate, propylene carbonate or butylene carbonate, aprotic solvents such as dimethylformamide or dimethylsulfoxide, and water.

Moreover, additives can be respectively used either alone or in combination corresponding to the purpose and in consideration of such factors as preparation form and treatment method in order to enhance the efficacy of compounds contained in the composition of the present invention. Examples of additives in the form of surfactants normally used for the purpose of emulsifying, dispersing, spreading or wetting agricultural chemical preparations include nonionic surfactants such as sorbitan fatty acid esters, polyoxyethylene sorbitan fatty acid esters, sucrose fatty acid esters, polyoxyethylene fatty acid esters, polyoxyethylene resin acid esters, polyoxyethylene fatty acid diesters, polyoxyethylene castor oil, polyoxyethylene alkyl ethers, polyoxyethylene alkyl phenyl ethers, polyoxyethylene dialkyl phenyl ethers, formalin condensates of polyoxyethylene alkyl phenyl ethers, polyoxyethylene-polyoxypropylene block copolymers, alkyl polyoxyethylene-polyoxypropylene block polymer ethers, alkyl phenyl polyoxyethylene-polyoxypropylene block polymer ethers, polyoxyethylene alkyl amines, polyoxyethylene fatty acid amides, polyoxyethylene bisphenyl ethers, polyoxyalkylene benzyl phenyl ethers, polyoxyalkylene styryl phenyl ethers, polyoxyalkylene adducts of higher alcohols, polyoxyethylene ethers, ester-based silicone and fluorine-based surfactants; anionic surfactants such as alkyl sulfates, polyoxyethylene alkyl ether sulfates, polyoxyethylene alkyl phenyl ether sulfates, polyoxyethylene benzyl phenyl ether sulfates, polyoxyethylene styryl phenyl ether sulfates, polyoxyethylene-polyoxypropylene block polymer sulfates, paraffin sulfonates, alkane sulfonates, AOS, dialkyl sulfosuccinates, alkyl benzene sulfonates, naphthalene sulfonates, dialkyl naphthalene sulfonates, formalin condensates of naphthalene sulfonates, alkyl diphenyl ether disulfonates, lignin sulfonates, polyoxyethylene alkyl phenyl ether sulfonates, polyoxyethylene alkyl ether sulfosuccinate half esters, fatty acid salts, N-methyl-fatty acid sarcosinates, resin acid salts, polyoxyethylene alkyl ether phosphates, polyoxyethylene phenyl ether phosphates, polyoxyethylene dialkyl phenyl ether phosphates, polyoxyethylene benzylated phenyl ether phosphates, polyoxyethylene benzylated phenyl ether phosphates, polyoxyethylene styrylated phenyl ether phosphates, polyoxyethylene styrylated phenyl ether phosphates, polyoxyethylene-polyoxypropylene block polymer phosphates, phosphatidylcholine, phosphatidylethanolimine, alkyl phosphates or sodium tripolyphosphate; polyanionic polymer surfactants derived from acrylic acid and acrylonitrile or acrylamidomethylpropane sulfonic acid; cationic surfactants such as alkyl trimethyl ammonium chlorides, methyl polyoxyethylene alkyl ammonium chlorides, alkyl-N-methyl pyridinium bromides, monomethylated ammonium chlorides, dialkyl methylated ammonium chlorides, alkyl pentamethyl propylene amine dichlorides, alkyl dimethyl benzalkonium chlorides or benzethonium chloride; and, amphoteric surfactants such as dialkyl diaminoethyl betaines or alkyl dimethyl benzyl betaines. Examples of binders used as additives include sodium alginate, polyvinyl alcohol, gum arabic, CMC sodium and bentonite, examples of disintegrating agents include CMC sodium and croscarmellose sodium, and examples of stabilizers include hindered phenol-based anti-oxidants and benzotriazole-based or hindered amine-based ultraviolet absorbers. Examples of pH adjusters include phosphoric acid, acetic acid and sodium hydroxide, and examples of antibacterial and antifungal agents include industrial disinfectants and antibacterial and antifungal agents such as 1,2-benzisothiazolin-3-one. Examples of thickeners include xanthan gum, guar gum, CMC sodium, gum arabic, polyvinyl alcohol and montmorillonite. Examples of antifoaming agents include silicone-based compounds, and examples of antifreezing agents include propylene glycol and ethylene glycol. However, the additives are not limited to those listed above.

Although examples of methods used to apply the composition of the present invention include treatment by spraying the foliage of plant individuals, seedling box treatment, soil surface spraying, soil surface spraying followed by soil incorporation, soil injection, soil injection followed by soil incorporation, soil irrigation, soil irrigation followed by soil incorporation, plant seed spraying, plant seed smearing, plant seed immersion and plant seed powder coating, any type of application method routinely used by persons with ordinary skill in the art demonstrates adequate efficacy.

In addition, the method for controlling plant disease in the present invention includes applying a plant disease control composition containing a compound of group a and a fungicidal compound of group b as active ingredients, simultaneously applying a plant disease control composition containing a compound of group a as an active ingredient and a plant disease control composition containing a fungicidal compound of group b as an active ingredient, or applying one of either a plant disease control composition containing a compound of group a as an active ingredient or a plant disease control composition containing a fungicidal compound of group b as an active ingredient followed by spraying the other composition, and the amount of time (time period) from applying one of either the plant disease control composition containing a compound of group a as an active ingredient or a plant disease control composition containing a fungicidal compound of group b as an active ingredient until spraying of the other composition is, for example, 1 minute to 2 weeks after applying either one of the compositions, preferably 5 minutes to 1 week after applying either one of the compositions, and more preferably 10 minutes to 3 days after applying either one of the compositions.

Moreover, the plant disease control composition of the present invention can be prepared as a composition comprising high concentrations of the quinoline compound represented by general formula (I) and a fungicidal compound of group b. This highly concentrated composition can be used as a spray by diluting with water. In addition, the plant disease control composition of the present invention can also be prepared as a mixture by mixing a composition containing a high concentration of the quinoline compound represented by general formula (I) and a composition containing a high concentration of a fungicidal compound of group b at the time of use. This highly concentrated composition can be used as a spray by diluting with water (tank-mixing).

Although the applied amount and applied concentration of the plant disease control composition containing a quinoline compound of group a and a fungicidal compound of group b as active ingredients thereof vary according to such factors as the target crop, target disease, degree of disease proliferation, compound drug form, application method and various environmental conditions, in the case of spraying, the applied amount is normally 10 g to 10,000 g per hectare and preferably 25 g to 5,000 g per hectare in terms of the amount of active ingredients. In addition, in the case of spraying after diluting a wettable powder, suspension concentrate or emulsion concentrate with water, the dilution factor thereof is normally 5 to 50,000, preferably 10 to 20,000 and more preferably 15 to 10,000. In addition, in the case of seed disinfection, the amount of the fungicide mixture used is normally 0.001 g to 50 g and preferably 0.01 g to 10 g per 1 kg of seeds. In the case of spraying the composition of the present invention onto the foliage of plant individuals, spraying onto the surface of soil, injecting into soil or irrigating soil drench, treatment may be carried out after diluting the chemical ingredient used to a suitable concentration in a suitable carrier. In the case of contacting the composition of the present invention with plant seeds, the plant seeds may be immersed in the chemical ingredient as is. In addition, plant seeds may be immersed, powder-coated, sprayed or smeared after diluting the chemical ingredient used to a suitable concentration in a suitable carrier. Although the amount of preparation used in the case of powder-coating, spraying or smearing is normally about 0.05% to 50% and preferably 0.1% to 30% of the dry weight of the plant seeds, the amount used is not limited thereto and can be varied according to the form of the preparation and the type of plant seeds targeted for treatment. Examples of suitable carriers include, but are not limited to, liquid carriers including water or organic solvents such as ethanol; and solid carriers in the manner of inorganic substances such as bentonite, montmorillonite, kaolinite, diatomaceous earth, kaolin, talc, clay, vermiculite, gypsum, calcium carbonate, amorphous silica or ammonium sulfate, plant-based organic substances such as soybean powder, wood meal, sawdust, wheat flour, lactose, sucrose or glucose, and urea.

Plant individuals as referred to in the present description refer to those that thrive without moving by carrying out photosynthesis, and specific examples thereof include, but are not limited to, rice, wheat, barley, corn, grapes, apples, pears, peaches, cherries, persimmons, citrus fruits, soybeans, green beans, strawberries, potatoes, cabbages, lettuces, tomatoes, cucumbers, eggplants, watermelons, beets, spinaches, peas, squashes, sugar canes, tobacco, green peppers, sweet potatoes, yams, konjac, rape, cotton, sunflowers, tulips, chrysanthemums and grasses.

Plant seeds as referred to in the present description refer to those used for agricultural propagation by storing nutrients for allowing the germination of seedlings, and specific examples thereof include, but are not limited to, corn, soybean, cotton, rice, sugar beet, wheat, barley, sunflower, tomato, cucumber, eggplant, spinach, pea, squash, sugar cane, tobacco, green pepper and rape seeds, yam, potato, sweet potato and konjac seed tubers, edible lily and tulip bulbs, shallot seed bulbs, and seeds of plants created by genetic or other artificial manipulation, including soybeans, corn, rape seeds or cotton that do not inherently exist in nature and have been imparted with herbicide resistance, rice or tobacco suitable for cold climates, and seeds of transformants of corn, cotton or potatoes that have been imparted with the ability to produce insecticides.

The composition of the present invention can naturally be used by mixing with other agricultural chemicals, soil conditioners or fertilizers such as insecticides, miticides, nematicides, fungicides, herbicides or plant growth regulators, and can be prepared by mixing therewith. Examples of insecticides, miticides and nematicides include, but are not limited to, pyrethroid-based compounds such as acrinathrin, allethrin [(1R)-isomer], bifenthrin, bioallethrin, bioallethrin S-cyclopentenyl isomer, bioresmethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, methothrin, metofluthrin, permethrin, phenothrin [(1R)-trans-isomer], prallethrin, resmethrin, RU15525 (kadethrin), silafluofen, tefluthrin, tetramethrin, tetramethrin [(1R)-isomer], tralomethrin, transfluthrin, ZXI8901, biopermethrin, furamethrin, profluthrin, flubrocythrinate or dimefluthrin, organic phosphorous-based compounds such as acephate, azamethiphos, azinphos-methyl, azinphos-ethyl, cadusafos, chlorethoxyfos, chlorfenvinphos, chlormephos, chlorpyrifos, chlorpyrifos-methyl, coumaphos, CYAP (cyanophos), demeton-S-methyl, diazinon, ECP (dichlofenthion), DDVP (dichlorvos), dicrotophos, dimethoate, dimethylvinphos, disulfoton (ethylthiometon), EPN (O-ethyl-O-4-nitrophenyl phosphonothioate), ethion, ethoprophos, famphur, fenamiphos, MEP (fenitrothion), MPP (fenthion), fosthiazate, heptenophos, isofenphos-methyl, isocarbophos (isopropyl O-(methoxyaminothio-phosphoryl)salicylate), isoxathion, malathion, mecarbam, methamidophos, DMTP (methidathion), mevinphos, monocrotophos, BRP (naled), omethoate, oxydemeton-methyl, parathion, parathion-methyl, PAP (phenthoate), phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, thiometon, triazophos, DEP (trichlorfon), vamidothion, Bayer 22/190 (chlorothion), bromfenvinfos, bromophos, bromophos-methyl, butathiofos, carbophenothion, chlorphoxim, sulprofos, diamidafos, CVMP (tetrachlorvinphos), propaphos, mesulfenfos, dioxabenzofos (salithion), etrimfos, oxydeprofos, formothion, fensulfothion, isazofos or imicyafos (AKD3088), oxime carbamate-based compounds such as alanycarb, butocarboxim, butoxycarboxim, thiodicarb or thiofanox, carbamate-based compounds such as aldicarb, bendiocarb, benfuracarb, NAC (carbaryl), carbofuran, carbosulfan, ethiofencarb, BPMC (fenobucarb), formetanate, furathiocarb, MIPC (isoprocarb), methiocarb, methomyl, oxamyl, pirimicarb, PHC (propoxur), trimethacarb, XMC, allyxycarb, aldoxycarb, bufencarb, butacarb, carbanolate, MTMC (metolcarb), MPMC (xylylcarb) or fenothiocarb, neonicotinoid-based compounds such as acetamiprid, clothianidin, dinotefuran, imidacloprid, nitenpyram, thiacloprid or thiamethoxam, diacylhydrazine-based compounds such as chromafenozide, halofenozide, methoxyfenozide or tebufenozide, benzoylurea-based compounds such as bistrifluron, chlorfluazuron, diflubenzuron, flucycloxuron, flufenoxuron, hexaflumuron, lufenuron, novaluron, noviflumuron, teflubenzuron or triflumuron, juvenile hormone-based compounds such as fenoxycarb, hydroprene, kinoprene, methoprene or pyriproxyfen, cyclodiene organochlorine-based compounds such as chlordane, endosulfan, lindane (gamma-HCH) or dienochlor, 2-dimethylaminopropane-1,3-dithiol-based compounds such as cartap hydrochloride or thiocyclam, amidine-based compounds such as amitraz, phenylpyrazole-based compounds such as ethiprole or fipronil, organic tin-based compounds such as azocyclotin, cyhexatin or fenbutatin oxide, METI-based compounds such as fenazaquin, fenpyroximate, pyridaben, pyrimidifen, tebufenpyrad or tolfenpyrad, benzylate-based compounds such as bromopropylate, allyl pyrrole-based compounds such as chlorfenapyr, nitrophenol-based compounds such as DNOC, anthranilic diamide-based compounds such as chlorantraniliprole or cyantraniliprole, oxadiazine-based compounds such as indoxacarb, semicarbazone-based compounds such as metaflumizone, tetronic acid-based compounds such as spirodiclofen or spiromesifen, carbamoyl triazole-based compounds such as triazamate, tetrazine-based compounds such as diflovidazin, as well as abamectin, acequinocyl, azadirachtin, bensultap, benzoximate, bifenazate, buprofezin, CGA 50 439, chinomethionate, clofentezine, cryolite, cyromazine, dazomet, DCIP, DDT, diafenthiuron, D-D (1,3-dichloropropane), dicofol, dicyclanil, dinobuton, dinocap, ENT 8184, etoxazole, flonicamid, fluacrypyrim, flubendiamide, GY-81 (peroxocarbonate), hexythiazox, hydramethylnon, hydrogen cyanide, methyl iodide, karanjin, MB-599 (verbutin), silver chloride, metam, methoxychlor, methyl isothiocyanate, milbemectin, pentachlorophenol, phosphine, piperonyl butoxide, polynactins, BPPS (propargite), pymetrozine, pyrethrin, pyridalyl, rotenone, S421 (bis(2,3,3,3-tetrachloropropyl) ether), sabadilla, spinosad, sulcofuronic acid (sulcofuronsodium), sulfluramid, tetradifon, thiosultap, tribufos, aldrin, amidithion, amidothioate, aminocarb, amiton, aramite, athidathion, azothoate, barium polysulfide, Bayer 22408, Bayer 32394, triflumezopyrim, benclothiaz, 5-(1,3-benzodioxol-5-yl)-3-hexylcyclohex-2-enone, 1,1-bis(4-chlorophenyl)-2-ethoxyethanol, butonate, butopyronoxyl, 2-(2-butoxyethoxy)ethyl thiocyanato, camphechlor, chlorbenside, chlordecone, chlordimeform, chlorfenethol, chlorfenson, isoprothiolane, fluazuron, lepimectin, spinetoram, emamectin benzoate, metaldehyde, phenisobromolate, bialaphos, levamisole hydrochloride, pyrifluquinazon (NNI0101), cyflumetofen, amidoflumet, IKA-2005, cyenopyrafen (NC512), spirotetramat (BYI08330), sulfoxaflor, pyrafluprole (V3039), pyriprole (V3086), tetraniliprole, cyclaniliprole, momfluorothrin, heptafluthrin, pyflubumide, flometoquin, fluensulfone, meperfluthrin, tetramethylfluthrin, kappa-bifenthrin, kappa-tefluthrin, dicloromezotiaz, flufiprole, tioxazafen, flupyradifurone, afidopyropen, fluhexafon and tralopyril.

The composition and control method of the present invention are effective against, for example, the types of plant diseases indicated below. The following indicates those specific diseases and pathogens thereof targeted for control by the present invention.

Examples thereof include, but are not limited to, blast (*Pyricularia oryzae*), sheath blight (*Thanatephorus cucumeris, Rhizoctonia solani*), brown spot (*Cochliobolus miyabeanus*), "Bakanae" disease (*Gibberella fujikuroi*), seedling blight (*Pythium* spp., *Fusarium* spp., *Trichoderma* spp., *Rhizopus* spp., *Rhizoctonia solani* etc.), false smut (*Claviceps virens*) and kernel smut (*Tilletia barclayana*) of rice; powdery mildew (*Erysiphe graminis* f. sp. *hordei*; f. sp. *tritici*), rust (*Puccinia striiformis; Puccinia graminis, Puccinia recondita, Puccinia hordei*), mottle leaf (*Pyrenophora graminea*), net blotch (*Pyrenophora teres*), fusarium blight (*Fusarium graminearum, Fusarium culmoruin, Fusarium avenaceum, Microdochium nivale*), snow mould (*Typhula incarnata, Typhula ishikariensis, Micronectriella nivalis*), loose kernel smut (*Ustilago nuda, Ustilago tritici, Ustilago nigra, Ustilago avenae*), stinking smut (*Tilletia caries, Tilletia pancicii*), eye spot (*Pseudocercosporella herpotrichoides*), foot rot (*Rhizoctonia cerealis*), scald (*Rhynchosporium secalis*), leaf blight (*Septoria tritici*), glume blotch (*Leptosphaeria nodorum*), seedling blight (*Fusarium* spp., *Pythium* spp., *Rhizoctonia* spp., *Septoria nodorum, Pyrenophora* spp.), damping off (*Gaeumannomyces graminis*), anthracnose (*Colletotrichum graminicola*), ergot (*Claviceps purpurea*) and spot blotch (*Cochliobolus sativus*) of family of wheat and barley; fusarium blight (*Fusarium graminearum* etc.), seedling blight (*Fusarium avenaceum, Penicillium* spp., *Pythium* spp., *Rhizoctonia* spp.), rust (*Puccinia sorghi*), brown spot (*Cochliobolus heterostrophus*), smut (*Ustilago maydis*), anthracnose (*Colletotrichum graininicola*) and Northern leaf spot (*Cochliobolus carbonum*) of corn; downy mildew (*Plasmopara viticola*), rust (*Phakopsora ampelopsidis*), powdery mildew (*Uncinula necator*), anthracnose (*Elsinoe ampelina*), ripe rot (*Glomerella cingulata*), black rot (*Guignardia bidwellii*), dead arm (*Phomopsis viticola*), fly speck (*Zygophiala jamaicensis*), gray mold (*Botrytis cinerea*), bud blight (*Diaporthe medusaea*), violet root rot (*Helicobasidium mompa*) and white root rot (*Rosellinia necatrix*) of grape vine; powdery mildew (*Podosphaera leucotricha*), scab (*Venturia inaequalis*), alternaria blotch (*Alternaria alternata* Apple pathotype), rust (*Gymnosporangium yamadae*), blossom blight (*Monillia mali*), valsa canker (*Valsa ceratosperma*), ring rot (*Botryosphaeria berengeriana*), anthracnose (*Colletotrichum acutatum*), fly speck (*Zygophiala jamaicensis*), sooty blotch (*Gloeodes pomigena*), fruit spot (*Mycosphaerella pomi*), violet root rot (*Helicobasidium mompa*), white root rot (*Rosellinia necatrix*), diaporthe canker (*Phomopsis mali, Diaporthe tanakae*) and blotch (*Diplocarpon mali*) of apple; pear black spot (*Alternaria alternata* Japanese pear pathotype), scab (*Venturia nashicola*), rust (*Gymnosporangium haraeanum*), Physalospora canker (*Physalospora piricola*) and canker (*Diaporthe medusaea, Diaporthe eres*) of Japanese pear, phytophthora rot (*Phytophthora cactorum*) of European pear; scab (*Cladosporium carpophilum*), phomopsis rot (*Phomopsis* sp.), phytophthora fruit rot (*Phytophthora* sp.) and anthracnose (*Gloeosporium laeticolor*) of peach; anthracnose (*Glomerella cingulata*), young-fruit rot (*Monilinia kusanoi*) and brown rot (*Monilinia fructicola*) of cherry; anthracnose (*Gloeosporium kaki*), angular leaf spot (*Cercospora kaki; Mycosphaerella nawae*), powdery mildew (*Phyllactinia kakikora*) of persimmon; melanose (*Diaporthe citri*), common green mold (*Penicillium digitatum*), blue mold (*Penicillium italicum*) and scab (*Elsinoe fawcettii*) of citrus;

gray mold (*Botrytis cinerea*) of tomato, cucumber, pulse, strawberry, potato, cabbage, eggplant, lettuce, etc.; stem rot (*Sclerotinia sclerotiorum*) of tomato, cucumber, bean, strawberry, potato, rape, cabbage, eggplant, lettuce, etc.; seedling blight (*Rhizoctonia* spp., *Pythium* spp., *Fusarium* spp., *Phytophthora* spp., *Sclerotinia sclerotiorum* etc.) of various kinds of vegetables such as tomato, cucumber, bean, Japanese radish, water melon, eggplant, rape, green pepper, spinach, sugar beet, etc.; downy mildew (*Pseudoperonospora cubensis*), powdery mildew (*Sphaerotheca fuliginea*), anthracnose (*Colletotrichum lagenarium*), gummy stem blight (*Mycosphaerella melonis*), fusarium wilt (*Fusarium oxysporum*) and phytophthora rot (*Phytophthora parasitica, Phytophthora melonis, Phytophthora nicotianae, Phy-* tophthora drechsleri, Phytophthora capsici etc.) of oriental melon; early blight (*Alternaria solani*), leaf mold (*Cladosporium fulvum*), late blight (*Phytophthora infestans*), fusarium wilt (*Fusarium oxysporum*), root rot (*Pythium myriotylum, Pythium dissotocum*) and anthracnose (*Colletotrichum phomoides*) of tomato; powdery mildew (*Sphaerotheca fuliginea* etc.), leaf mold (*Mycovellosiella nattrassii*), late blight (*Phytophthora infestans*) and brown rot (*Phytophthora capsici*) of eggplant; alternaria leaf spot (*Alternaria brassicae*) of rapeseed, alternaria leaf spot (*Alternaria brassicae* etc.), white spot (*Cercosporella brassicae*), blackleg (*Leptosphaeria inaculans*), club root (*Plasmodiophora brassicae*) and downy mildew (*Peronospora brassicae*) of *Brassica* vegetables; foot rot (*Rhizoctonia solani*), yellows (*Fusarium oxysporum*) of cabbage; bottom rot (*Rhizoctonia solani*) and yellows (*Verticillium dahliae*) of Chinese cabbage; rust (*Puccinia allii*), alternaria leaf spot (*Alternaria pomi*), southern blight (*Sclerotium rolfsii*) and white tip disease (*Phytophthora pomi*) of welsh onion; purple stain (*Cercospora kikuchii*), sphaceloma scab (*Elsinoe glycines*), black spot (*Diaporthe phaseolorum*), rhizoctonia root rot (*Rhizoctonia solani*), stem rot (*Phytophthora megasperma*), downy mildew (*Peronospora manshurica*), rust (*Phakopsora pachyrhizi*) and anthracnose (*Colletotrichum truncatum*) of soybean; anthracnose (*Colletotrichum lindemuthianum*) of kidney bean; leaf spot (*Mycosphaerella personatum*) and brown leaf spot (*Cercospora arachidicola*) of peanuts; powdery mildew (*Erysiphe pisi*) and downy mildew (*Peronospora pisi*) of pea; downy mildew (*Peronospora viciae*) and phytophthora rot (*Phytophthora nicotianae*) of broad bean; early blight (*Alternaria solani*), black scurf (*Rhizoctonia solani*), late blight (*Phytophthora infestans*), silver scurf (*Spondylocladium atrovirens*), dry spot (*Fusarium oxysporum, Fusarium solani*) and powdery scab (*Spongospora subterranea*) of potato; cercospora leaf spot (*Cercospora beticola*), downy mildew (*Peronospora schachtii*), aphanomyces root rot (*Aphanomyces cochlioides*) and leaf spot (*Phoma betae*) of sugar beet; leaf blight (*Alternaria dauci*) of carrots; powdery mildew (*Sphaerotheca humuli*), phytophthora rot (*Phytophthora nicotianae*), anthracnose (*Gloinerella cingulata*) and soft-rotted fruits (*Pythium ultimum* Trow var. *ultimum*) of strawberry; net blister blight (*Exobasidium reticulatum*), white scab (*Elsinoe leucospila*), anthracnose (*Colletotrichum theaesinensis*) and gray blight (*Pestalotiopsis longiseta*) of green tea; brown spot (*Alternaria alternata* (Tobacco pathotype)), powdery mildew (*Erysiphe cichoracearum*), anthracnose (*Colletotrichum tabacum*) and black shank (*Phytophthora parasitica*) of tobacco; damping off (*Fusarium oxysporum*) of cotton; sclerotinia rot (*Sclerotinia sclerotiorum*) of sunflower; black spot (*Diplocarpon rosae*), powdery mildew (*Sphaerotheca pannosa*), phytophthora rot (*Phytophthora megasperma*) and downy mildew (*Peronospora sparsa*) of rose; leaf blight (*Septoria chrysanthemi-indici*), rust (*Puccinia horiana*) and phytophthora rot (*Phytophthora cactorum*) of chrysanthemum; or brown patch (*Rhizoctonia solani*), dollar spot (*Sclerotinia homoeocarpa*), Curvularia leaf blight (*Curvularia geniculata*), rust (*Puccinia zoysiae*), Helminthosporium leaf blight (*Cochliobolus* sp.), scald (*Rhynchosporium secalis*), damping off (*Gaeumannomyces graminis*), anthracnose (*Colletotrichum graminicola*), typhula brown snow blight (*Typhula incarnata*), typhula black snow blight (*Typhula ishikariensis*), sclerotinia snow blight (*Sclerotinia borealis*), fairy rings (*Marasmius oreades* etc.), pythium blight (*Pythium aphanidermatum* etc.) and blast (*Pyricularia oryzae*) of turf grass.

More preferable targets for controlling plant diseases by the present invention are blast (*Pyricularia oryzae*), brown spot (*Cochliobolus miyabeanus*), "Bakanae" disease (*Gibberella fujikuroi*), seedling blight (*Pythium* spp., *Fusarium* spp., *Trichoderma* spp., *Rhizopus* spp., *Rhizoctonia solani* etc.) and false smut (*Claviceps virens*) of rice; powdery mildew (*Erysiphe graminis* f. sp. *hordei*; f. sp. *tritici*), mottle leaf (*Pyrenophora graininea*), net blotch (*Pyrenophora teres*), fusarium blight (*Fusarium graminearum, Fusarium culmorum, Fusarium avenaceum, Microdochium nivale*), snow mould (*Typhula incarnata, Typhula ishikariensis, Micronectriella nivalis*), eye spot (*Pseudocercosporella herpotrichoides*), foot rot (*Rhizoctonia cerealis*), scald (*Rhynchosporium secalis*), leaf blight (*Septoria tritici*), seedling blight (*Fusarium* spp., *Pythium* spp., *Rhizoctonia* spp., *Septoria nodorum, Pyrenophora* spp.), damping off (*Gaeumannomyces graminis*), anthracnose (*Colletotrichum graininicola*), ergot (*Claviceps purpurea*) and spot blotch (*Cochliobolus sativus*) of family of wheat and barley; fusarium blight (*Fusarium graininearum* etc.), seedling blight (*Fusarium avenaceum, Penicillium* spp., *Pythium* spp., *Rhizoctonia* spp.), brown spot (*Cochliobolus heterostrophus*) and Northern leaf spot (*Cochliobolus carbonum*) of corn; powdery mildew (*Uncinula necator*), anthracnose (*Elsinoe ampelina*), ripe rot (*Glomerella cingulata*), black rot (*Guignardia* bidwellii), dead arm (*Phomopsis* viticola), fly speck (*Zygophiala jamaicensis*), gray mold (*Botrytis cinerea*), bud blight (*Diaporthe* medusaea), violet root rot (*Helicobasidium mompa*) and white root rot (*Rosellinia necatrix*) of grape vine; powdery mildew (*Podosphaera leucotricha*), scab (*Venturia inaequalis*), alternaria blotch (*Alternaria alternata* Apple pathotype), blossom blight (*Monillia mali*), valsa canker (*Valsa ceratosperma*), ring rot (*Botryosphaeria* berengeriana), anthracnose (*Colletotrichum acutatum*), fly speck (*Zygophiala jamaicensis*), sooty blotch (*Gloeodes pomigena*), fruit spot (*Mycosphaerella pomi*), violet root rot (*Helicobasidium mompa*), white root rot (*Rosellinia necatrix*), diaporthe canker (*Phomopsis mali, Diaporthe tanakae*) and blotch (*Diplocarpon mali*) of apple; pear black spot (*Alternaria alternata* Japanese pear pathotype), scab (*Venturia nashicola*), Physalospora canker (*Physalospora piricola*) and canker (*Diaporthe medusaea, Diaporthe eres*) of Japanese pear, scab (*Cladosporium carpophilum*), phomopsis rot (*Phomopsis* sp.) and anthracnose (*Gloeosporium laeticolor*) of peach; anthracnose (*Glomerella cingulata*), young-fruit rot (*Monilinia kusanoi*) and brown rot (*Monilinia fructicola*) of cherry; anthracnose (*Gloeosporium kaki*), angular leaf spot (*Cercospora kaki; Mycosphaerella nawae*) and powdery mildew (*Phyllactinia kakikora*) of persimmon; melanose (*Diaporthe citri*), common green mold (*Penicillium digitatum*), blue mold (*Penicillium italicum*) and scab (*Elsinoe fawcettii*) of citrus;

gray mold (*Botrytis cinerea*) of tomato, cucumber, pulse, strawberry, potato, cabbage, eggplant, lettuce, etc.; stem rot (*Sclerotinia sclerotiorum*) of tomato, cucumber, bean, strawberry, potato, rape, cabbage, eggplant, lettuce, etc.; seedling blight (*Rhizoctonia* spp., *Pythium* spp., *Fusarium* spp., *Phytophthora* spp., *Sclerotinia sclerotiorum* etc.) of various kinds of vegetables such as tomato, cucumber, bean, Japanese radish, water melon, eggplant, rape, green pepper, spinach, sugar beet, etc.; powdery mildew (*Sphaerotheca fuliginea*), anthracnose (*Colletotrichum lagenarium*), gummy stem blight (*Mycosphaerella melonis*) and *fusarium* wilt (*Fusarium oxysporum*) of oriental melon; early blight (*Alternaria solani*), leaf mold (*Cladosporium fulvum*), fusarium wilt (*Fusarium oxysporum*) and anthracnose (*Colletotrichum phomoides*) of tomato; powdery mildew (*Sphaerotheca fuliginea etc.), of eggplant; alternaria leaf spot (*Alternaria brassicae*) of rapeseed, alternaria leaf spot (*Alternaria brassicae* etc.), white spot (*Cercosporella brassicae*), blackleg (*Leptosphaeria maculans*) of *Brassica* vegetables; yellows (*Fusarium oxysporum*) of cabbage; yellows (*Verticillium dahliae*) of Chinese cabbage; *alternaria* leaf spot (*Alternaria pomi*) of welsh onion; purple stain (*Cercospora kikuchii*), sphaceloma scab (*Elsinoe glycines*), black spot (*Diaporthe phaseolorum*) and anthracnose (*Colletotrichum truncatum*) of soybean; anthracnose (*Colletotrichum lindemuthianum*) of kidney bean; leaf spot (*Mycosphaerella personatum*) and brown leaf spot (*Cercospora arachidicola*) of peanuts; powdery mildew (*Erysiphe pisi*) of pea; early blight (*Alternaria solani*) and silver scurf (*Spondylocladium atrovirens*), of potato; *cercospora* leaf spot (*Cercospora beticola*) and leaf spot (*Phoma betae*) of sugar beet; leaf blight (*Alternaria dauci*) of carrots;

powdery mildew (*Sphaerotheca humuli*) and anthracnose (*Glomerella cingulata*) of strawberry; white scab (*Elsinoe leucospila*), anthracnose (*Colletotrichum theaesinensis*) and gray blight (*Pestalotiopsis longiseta*) of green tea; brown spot (*Alternaria alternata* (Tobacco pathotype)), powdery mildew (*Erysiphe cichoracearum*) and anthracnose (*Colletotrichum tabacum*) of tobacco; damping off (*Fusarium oxysporum*) of cotton; sclerotinia rot (*Sclerotinia sclerotiorum*) of sunflower; black spot (*Diplocarpon rosae*) and powdery mildew (*Sphaerotheca pannosa*) of rose; leaf blight (*Septoria chrysanthemi-indici*) of chrysanthemum; or dollar spot (*Sclerotinia homoeocarpa*), *Curvularia* leaf blight (*Curvularia geniculata*), *Helminthosporium* leaf blight (*Cochliobolus* sp.), scald (*Rhynchosporium secalis*), damping off (*Gaeumannomyces graminis*), anthracnose (*Colletotrichum graminicola*), typhula brown snow blight (*Typhula incarnata*), typhula black snow blight (*Typhula ishikariensis*), sclerotinia snow blight (*Sclerotinia borealis*), fairy rings (*Marasmius oreades* etc.) and blast (*Pyricularia oryzae*) of turf grass.

EXAMPLES

The following provides a more detailed explanation of the present invention by listing preparation examples and test examples thereof. However, the present invention is not limited to only these preparation examples and test examples. Furthermore, the number of parts of all incorporated amounts of each component described in the following preparation examples refers to parts by weight.

Compound A (a-14), B (a-18) and C (a-20) among the compounds (I: group a) used in the following preparation examples and test examples respectively refer to Compound Nos. 1-866, 1-929 and 1-930 of International Publication No. WO 2005/070917, and are respectively described therein in Examples 114, 177 and 178. The chemical structures thereof are shown in Table 1.

TABLE 1

| Compound | $R^1$ | $R^2$ | $R^3$ | $R^4$ | Xn | Ym |
|---|---|---|---|---|---|---|
| A(a-14) | Me | Me | Me | Me | 5-F | H |
| B(a-18) | Me | Me | F | F | H | H |
| C(a-20) | Me | Me | F | F | 5-F | H |

In addition, the fungicidal compound of formula (VII)-1 of compound (b-38) used in the following preparation examples and test examples is a compound represented by the following formula.

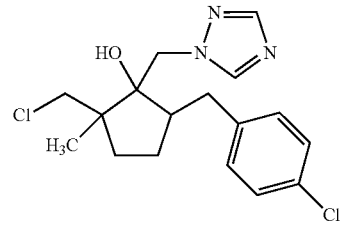

(VII)-1

Preparation Example 1 Wettable Powder (WP) (a1)

Component I (group a) in the form of any of Compounds A, B and C (10, 1 or 0.01 parts), Component II (group b) in the form of any of the compounds described below (added amount indicated), Neogen powder (0.5 parts), Carplex (0.5 parts), Gohsenol (0.2 parts), Radiolite (0.8 parts) and H fine powder (used as the balance to bring to a total of 100 parts) were crushed and mixed to obtain wettable powder (a1).

The compounds (added amounts) used for Component II (group b) consisted of (b-1) (2 parts), (b-2) (2 parts), (b-3) (2 parts), (b-4) (2 to 10 parts), (b-5) (2 to 50 parts), (b-6) (0.4 to 50 parts), (b-7) (0.4 to 50 parts), (b-8) (0.4 to 2 parts), (b-9) (0.4 to 2 parts), (b-16) (2 parts), (b-19) (2 parts), (b-20) (0.4 to 10 parts), (b-21) (0.4 to 10 parts), (b-22) (0.4 to 10 parts), (b-23) (2 to 10 parts), (b-24) (0.4 to 10 parts), (b-25) (0.4 to 10 parts), (b-26) (0.4 to 10 parts), (b-27) (0.4 to 10 parts), (b-28) (0.4 to 10 parts), (b-29) (0.4 to 10 parts), (b-30) (0.4 to 10 parts), (b-31) (0.4 to 10 parts), (b-32) (0.4 to 10 parts), (b-33) (25 to 50 parts), (b-34) (0.4 to 10 parts), (b-35) (0.4 to 10 parts), (b-36) (0.4 to 10 parts), (b-38) (2 parts), (b-39) (0.4 parts), (b-40) (2 parts), (b-41) (50 parts), (b-42) (50 parts), (b-43) (2 to 10 parts), (b-44) (0.08 parts), (b-45) (10 parts), (b-46) (2 to 10 parts), (b-47) (10 parts), (b-49) (2 parts), (b-50) (2 parts), (b-51) (2 to 50 parts), (b-52) (2 to 50 parts), (b-53) (2 to 50 parts), (b-54) (2 parts), (b-55) (2 to 10 parts), (b-58) (10 to 50 parts), (b-59) (2 parts), (b-60) (10 to 50 parts), (b-61) (10 to 50 parts), (b-62) (10 to 50 parts), (b-63) (0.016 to 50 parts), (b-64) (10 parts), (b-65) (0.4 to 50 parts), (b-66) (0.4 to 50 parts), (b-67) (50 parts), (b-68) (50 parts), (b-69) (50 parts), (b-70) (50 parts), (b-71) (10 to 50 parts), (b-72) (2 to 10 parts), (b-73) (10 parts), (b-74) (0.4 to 50 parts), (b-75) (2 parts), (b-76) (25 parts), (b-77) (0.016 to 50 parts), (b-78) (0.4 parts), (b-81) (2 to 50 parts), (b-82) (0.08 to 50 parts), (b-83) (0.08 to 10 parts), (b-84) (0.0016 to 50 parts), (b-85) (10 parts), (b-88) (2 parts), (b-89) (2 parts), (b-91) (0.08 to 2 parts), (b-92) (0.4 parts), (b-93) (50 parts), (b-94) (0.4 to 10 parts), (b-95) (2 parts), (b-96) (10 to 50 parts), (b-97) (0.08 parts), (b-98) (2 parts), (b-99) (10 to 50 parts), (b-100) (0.016 to 50 parts), (b-101) (0.4 to 50 parts), (b-102) (0.4 to 50 parts), (b-103) (10 to 50 parts), (b-104) (50 parts), (b-105) (25 to 50 parts), (b-106) (25 parts).

Preparation Example 2 Suspension Concentrate (SC) (b1)

Component I (group a) in the form of any of Compounds A, B and C (10 or 1 parts), Component II (group b) in the form of any of the compounds described below (added amount indicated), propylene glycol (7 parts), sodium lignin sulfonate (4 parts), sodium dioctylsulfosuccinate (2 parts) and water (used as the balance to bring to a total of 100 parts) were wet-crushed with a sand grinder to obtain suspension concentrate (b1).

The compounds (added amounts) used for Component II (group b) consisted of (b-1) (2 parts), (b-2) (2 parts), (b-3) (2 parts), (b-4) (2 to 10 parts), (b-5) (2 to 50 parts), (b-6) (0.4 to 50 parts), (b-7) (0.4 to 50 parts), (b-8) (0.4 to 2 parts), (b-9) (0.4 to 2 parts), (b-16) (2 parts), (b-19) (2 parts), (b-20) (0.4 to 10 parts), (b-21) (0.4 to 10 parts), (b-22) (0.4 to 10 parts), (b-23) (2 to 10 parts), (b-24) (0.4 to 10 parts), (b-25) (0.4 to 10 parts), (b-26) (0.4 to 10 parts), (b-27) (0.4 to 10 parts), (b-28) (0.4 to 10 parts), (b-29) (0.4 to 10 parts), (b-30) (0.4 to 10 parts), (b-31) (0.4 to 10 parts), (b-32) (0.4 to 10 parts), (b-33) (25 to 50 parts), (b-34) (0.4 to 10 parts), (b-35) (0.4 to 10 parts), (b-36) (0.4 to 10 parts), (b-38) (2 parts), (b-39) (0.4 parts), (b-40) (2 parts), (b-41) (50 parts), (b-42) (50 parts), (b-43) (2 to 10 parts), (b-44) (0.08 parts), (b-45) (10 parts), (b-46) (2 to 10 parts), (b-47) (10 parts), (b-49) (2 parts), (b-50) (2 parts), (b-51) (2 to 50 parts), (b-52) (2 to 50 parts), (b-53) (2 to 50 parts), (b-54) (2 parts), (b-55) (2 to 10 parts), (b-58) (10 to 50 parts), (b-59) (2 parts), (b-60) (10 to 50 parts), (b-61) (10 to 50 parts), (b-62) (10 to 50 parts), (b-63) (0.016 to 50 parts), (b-64) (10 parts), (b-65) (0.4 to 50 parts), (b-66) (0.4 to 50 parts), (b-67) (50 parts), (b-68) (50 parts), (b-69) (50 parts), (b-70) (50 parts), (b-71) (10 to 50 parts), (b-72) (2 to 10 parts), (b-73) (10 parts), (b-74) (0.4 to 50 parts), (b-75) (2 parts), (b-76) (25 parts), (b-77) (0.016 to 50 parts), (b-78) (0.4 parts), (b-81) (2 to 50 parts), (b-82) (0.08 to 50 parts), (b-83) (0.08 to 10 parts), (b-84) (0.0016 to 50 parts), (b-85) (10 parts), (b-88) (2 parts), (b-89) (2 parts), (b-91) (0.08 to 2 parts), (b-92) (0.4 parts), (b-94) (0.4 to 10 parts), (b-95) (2 parts), (b-96) (10 to 50 parts), (b-97) (0.08 parts), (b-98) (2 parts), (b-99) (10 to 50 parts), (b-100) (0.016 to 50 parts), (b-101) (0.4 to 50 parts), (b-102) (0.4 to 50 parts), (b-103) (10 to 50 parts), (b-104) (50 parts), (b-105) (25 to 50 parts), (b-106) (25 parts).

Preparation Example 3 Emulsion Concentrate (EC) (c1)

Component I (group a) in the form of any of Compounds A, B and C (10 or 1 parts), Component II (group b) in the form of any of the compounds described below (added amount indicated), cyclohexane (10 parts), Tween20 (surfactant, 20 parts) and xylene (used as the balance to bring to a total of 100 parts) were uniformly dissolved and mixed to obtain emulsion concentrate (c1).

The compounds (added amounts) used for Component II (group b) consisted of (b-1) (2 parts), (b-2) (2 parts), (b-3) (2 parts), (b-4) (2 to 10 parts), (b-5) (2 to 50 parts), (b-6) (0.4 to 50 parts), (b-7) (0.4 to 50 parts), (b-8) (0.4 to 2 parts), (b-9) (0.4 to 2 parts), (b-16) (2 parts), (b-19) (2 parts), (b-20) (0.4 to 10 parts), (b-21) (0.4 to 10 parts), (b-22) (0.4 to 10 parts), (b-23) (2 to 10 parts), (b-24) (0.4 to 10 parts), (b-25) (0.4 to 10 parts), (b-26) (0.4 to 10 parts), (b-27) (0.4 to 10 parts), (b-28) (0.4 to 10 parts), (b-29) (0.4 to 10 parts), (b-30) (0.4 to 10 parts), (b-31) (0.4 to 10 parts), (b-32) (0.4 to 10 parts), (b-33) (25 to 50 parts), (b-34) (0.4 to 10 parts), (b-35) (0.4 to 10 parts), (b-36) (0.4 to 10 parts), (b-38) (2 parts), (b-39) (0.4 parts), (b-40) (2 parts), (b-41) (50 parts), (b-42) (50 parts), (b-43) (2 to 10 parts), (b-44) (0.08 parts), (b-45) (10 parts), (b-46) (2 to 10 parts), (b-47) (10 parts), (b-49) (2 parts), (b-50) (2 parts), (b-51) (2 to 50 parts), (b-52) (2 to 50 parts), (b-53) (2 to 50 parts), (b-54) (2 parts), (b-55) (2 to 10 parts), (b-58) (10 to 50 parts), (b-59) (2 parts), (b-60) (10 to 50 parts), (b-61) (10 to 50 parts), (b-62) (10 to 50 parts), (b-63) (0.016 to 50 parts), (b-64) (10 parts), (b-65) (0.4 to 50 parts), (b-66) (0.4 to 50 parts), (b-67) (50 parts), (b-68) (50 parts), (b-69) (50 parts), (b-70) (50 parts), (b-71) (10 to 50 parts), (b-72) (2 to 10 parts), (b-73) (10 parts), (b-74) (0.4 to 50 parts), (b-75) (2 parts), (b-76) (25 parts), (b-77) (0.016 to 50 parts), (b-78) (0.4 parts), (b-81) (2 to 50 parts), (b-82) (0.08 to 50 parts), (b-83) (0.08 to 10 parts), (b-84) (0.0016 to 50 parts), (b-85) (10 parts), (b-88) (2 parts), (b-89) (2 parts), (b-91) (0.08 to 2 parts), (b-92) (0.4 parts), (b-94) (0.4 to 10 parts), (b-95) (2 parts), (b-96) (10 to 50 parts), (b-97) (0.08 parts), (b-98) (2 parts), (b-99) (10 to 50 parts), (b-100) (0.016 to 50 parts), (b-101) (0.4 to 50 parts), (b-102) (0.4 to 50 parts), (b-103) (10 to 50 parts), (b-104) (50 parts), (b-105) (25 to 50 parts), (b-106) (25 parts).

Comparative Preparation Example 1 Wettable Powder (WP) (a2)

Water-dispersible powder (a2) was obtained using the same method as Preparation Example 1 with the exception of containing only one of either Component I (group a) or Component II (group b).

Comparative Preparation Example 2 Suspension Concentrate (SC) (b2)

Suspension concentrate preparation (b2) was obtained using the same method as Preparation Example 2 with the exception of containing only one of either Component I (group a) or Component II (group b).

Comparative Preparation Example 3 Emulsion Concentrate (EC) (c2)

Emulsion (c2) was obtained using the same method as Preparation Example 3 with the exception of containing only one of either Component I (group a) or Component II (group b).

Comparative Preparation Example 4 Wettable Powder (WP) (a3)

Water-dispersible powder (a3) was obtained using the same method as Preparation Example 1 with the exception of containing Component II (group b) compounds described below in place of those used for Wettable powder (WP) (a1). The compounds (added amounts) used for Component II (group b) consisted of Diclocymet (0.4 to 50 parts), Carpropamid (0.4 to 50 parts), Tolclofos-methyl (10 to 50 parts), and Oxolinic acid (50 parts).

Test Example 1 Tomato Gray Mold Preventive Test

Tomato plants (variety: Ohgata Fukuju) planted in plastic pots having a diameter of 5 cm were grown indoors to the second to third leaf stage. Wettable powder prepared in compliance with Preparation Example 1 and Comparative Preparation Example 1 containing the compounds indicated in Table 2 were diluted with water to a prescribed concentration followed by spraying with a sprayer in 5 ml aliquots per 2 pots. After the chemical had dried, a conidia suspension of *Botrytis cinerea* which prepared from previously cultured in PDA medium was inoculated by spraying onto the plants. Following inoculation, the pots were placed in the humidified chamber of an artificial inoculation room (25° C.) and after 2 days, the pots were taken out and controlling effects were examined. During the examination, the percentage of affected area exhibiting lesions on a single tomato leaf was determined in accordance with the following incidence degree indicators. In addition, control values were calculated according to the equation indicated below from the average incidence degree of each treated group. The spray test results and theoretical values as determined according to Colby's formula are shown in Table 2.

| Incidence Degree Indicators | |
|---|---|
| Indicator | Incidence Degree |
| 0 | No lesions |
| 0.5 | Lesion area of about 1% to 2% |
| 1 | Lesion area of less than 5% |
| 2 | Lesion area of less than 25% |
| 3 | Lesion area of less than 50% |
| 4 | Lesion area of less than 75% |
| 5 | Lesion area of less than 95% |
| 6 | Lesion area of 95% or more or withered |

Furthermore, the average values of each treated group and an untreated group were used for incidence degree.

Control values were calculated from the equation indicated below.

Control value=(1−leaflet incidence rate of treated group/leaflet incidence rate of untreated group)×100

Furthermore, synergistic effects were evaluated using Colby's formula. Colby's formula is expressed as $X=P+Q-P\times Q/100$, where X represents the theoretical value of the control value, P represents the control value in the case of spraying a certain chemical agent alone, and Q represents the control value in the case of spraying the chemical agent used in combination alone. In the case the actual measured effect is greater than the effect X as calculated with the aforementioned Colby's formula, the action resulting from combining two types of active ingredients is indicated to be more than additive, that is, to be synergistic.

TABLE 2-1

| Effective ingredient in the preparation | Treatment concentration (ppm) | Control value | Theoretical value |
|---|---|---|---|
| A + Compound of formula (II) (b-3) | 10 + 2 | 93 | 64 |
| A + Picarbutrazox (b-78) | 10 + 0.4 | 86 | 64 |
| A + Compound of formula (XIV) (b-88) | 10 + 2 | 89 | 69 |
| A + Compound of formula (VII)-1 (b-3 8) | 10 + 2 | 82 | 67 |
| B + Compound of formula (II) (b-3) | 10 + 2 | 79 | 57 |
| B + Picarbutrazox (b-78) | 10 + 0.4 | 86 | 57 |
| B + Compound of formula (XIV) (b-88) | 10 + 2 | 79 | 63 |
| B + Compound of formula (VII)-1 (b-38) | 10 + 2 | 82 | 60 |
| C + Compound of formula (II) (b-3) | 10 + 2 | 79 | 57 |
| C + Picarbutrazox (b-78) | 10 + 0.4 | 75 | 57 |
| C + Compound of formula (XIV) (b-88) | 10 + 2 | 82 | 63 |
| C + Compound of formula (VII)-1 (b-38) | 10 + 2 | 82 | 60 |
| Compound of formula (II) (b-3) | 2 | 0 | |
| Picarbutrazox (b-78) | 0.4 | 0 | |
| Compound of formula (XIV) (b-88) | 2 | 14 | |
| Compound of formula (VII)-1 (b-38) | 2 | 7 | |
| A | 10 | 64 | |
| B | 10 | 57 | |
| C | 10 | 57 | |

TABLE 2-2

| Effective ingredient in the preparation | Treatment concentration (ppm) | Preventive value | Theoretical value |
|---|---|---|---|
| A + Fluoxastrobin (b-51) | 10 + 50 | 97 | 86 |
| A + Dimoxystrobin (b-52) | 10 + 50 | 97 | 81 |
| A + Orysastrobin (b-53) | 10 + 50 | 100 | 88 |

TABLE 2-2-continued

| Effective ingredient in the preparation | Treatment concentration (ppm) | Preventive value | Theoretical value |
|---|---|---|---|
| B + Fluoxastrobin (b-51) | 10 + 50 | 100 | 86 |
| B + Dimoxystrobin (b-52) | 10 + 50 | 97 | 81 |
| B + Orysastrobin (b-53) | 10 + 50 | 100 | 88 |
| C + Fluoxastrobin (b-51) | 10 + 50 | 97 | 84 |
| C + Dimoxystrobin (b-52) | 10 + 50 | 97 | 78 |
| C + Orysastrobin (b-53) | 10 + 50 | 100 | 86 |
| Fluoxastrobin (b-51) | 50 | 40 | |
| Dimoxystrobin (b-52) | 50 | 17 | |
| Orysastrobin (b-53) | 50 | 47 | |
| A | 10 | 77 | |
| B | 10 | 77 | |
| C | 10 | 73 | |

TABLE 2-3

| Effective ingredient in the preparation | Treatment concentration (ppm) | Preventive value | Theoretical value |
|---|---|---|---|
| A + Carboxin (b-41) | 10 + 50 | 97 | 75 |
| A + Thifluzamide (b-42) | 10 + 50 | 100 | 77 |
| A + Isopyrazam (b-7) | 10 + 50 | 100 | 82 |
| A + Sedaxane (b-6) | 10 + 50 | 97 | 85 |
| A + Penflufen (b-5) | 10 + 50 | 100 | 84 |
| A + Cyprodinil (b-61) | 10 + 50 | 97 | 85 |
| A + Fenpyrazamine (b-99) | 10 + 10 | 97 | 84 |
| B + Carboxin (b-41) | 10 + 50 | 97 | 75 |
| B + Thifluzamide (b-42) | 10 + 50 | 97 | 77 |
| B + Isopyrazam (b-7) | 10 + 50 | 97 | 82 |
| B + Sedaxane (b-6) | 10 + 50 | 100 | 85 |
| B + Penflufen (b-5) | 10 + 50 | 100 | 84 |
| B + Cyprodinil (b-61) | 10 + 50 | 100 | 85 |
| B + Fenpyrazamine (b-99) | 10 + 10 | 97 | 84 |
| C + Carboxin (b-41) | 10 + 50 | 100 | 67 |
| C + Thifluzamide (b-42) | 10 + 50 | 100 | 69 |
| C + Isopyrazam (b-7) | 10 + 50 | 97 | 76 |
| C + Sedaxane (b-6) | 10 + 50 | 100 | 80 |
| C + Penflufen (b-5) | 10 + 50 | 97 | 79 |
| C + Cyprodinil (b-61) | 10 + 50 | 97 | 80 |
| C + Fenpyrazamine (b-99) | 10 + 10 | 97 | 79 |
| Carboxin (b-41) | 50 | 17 | |
| Thifluzamide (b-42) | 50 | 23 | |
| Isopyrazam (b-7) | 50 | 40 | |
| Sedaxane (b-6) | 50 | 50 | |
| Penflufen (b-5) | 50 | 47 | |
| Cyprodinil (b-61) | 50 | 50 | |
| Fenpyrazamine (b-99) | 10 | 47 | |
| A | 10 | 70 | |
| B | 10 | 70 | |
| C | 10 | 60 | |

TABLE 2-4

| Effective ingredient in the preparation | Treatment concentration (ppm) | Preventive value | Theoretical value |
|---|---|---|---|
| A + Tetraconazole (b-22) | 10 + 10 | 97 | 84 |
| A + Epoxiconazole (b-24) | 10 + 10 | 100 | 82 |
| A + Ipconazole (b-25) | 10 + 10 | 100 | 84 |
| A + Metconazole (b-26) | 10 + 10 | 97 | 84 |
| A + Propiconazole (b-27) | 10 + 10 | 100 | 82 |
| A + Cyproconazole (b-28) | 10 + 10 | 100 | 82 |
| A + Difenoconazole (b-29) | 10 + 10 | 97 | 84 |
| A + Fluquinconazole (b-30) | 10 + 10 | 100 | 84 |
| A + Flusilazole (b-31) | 10 + 10 | 100 | 82 |
| A + Penconazole (b-32) | 10 + 10 | 97 | 78 |
| A + Flutriafol (b-34) | 10 + 10 | 97 | 82 |

TABLE 2-4-continued

| Effective ingredient in the preparation | Treatment concentration (ppm) | Preventive value | Theoretical value |
| --- | --- | --- | --- |
| A + Myclobutanil (b-35) | 10 + 10 | 100 | 82 |
| A + Imazalil (b-20) | 10 + 10 | 100 | 78 |
| A + Prochloraz (b-21) | 10 + 10 | 100 | 78 |
| B + Tetraconazole (b-22) | 10 + 10 | 100 | 84 |
| B + Epoxiconazole (b-24) | 10 + 10 | 100 | 82 |
| B + Ipconazole (b-25) | 10 + 10 | 97 | 84 |
| B + Metconazole (b-26) | 10 + 10 | 100 | 84 |
| B + Propiconazole (b-27) | 10 + 10 | 100 | 82 |
| B + Cyproconazole (b-28) | 10 + 10 | 100 | 78 |
| B + Difenoconazole (b-29) | 10 + 10 | 97 | 82 |
| B + Fluquinconazole (b-30) | 10 + 10 | 97 | 82 |
| B + Flusilazole (b-31) | 10 + 10 | 100 | 78 |
| B + Penconazole (b-32) | 10 + 10 | 100 | 78 |
| B + Flutriafol (b-34) | 10 + 10 | 100 | 82 |
| B + Myclobutanil (b-35) | 10 + 10 | 100 | 78 |
| B + Imazalil (b-20) | 10 + 10 | 97 | 78 |
| B + Prochloraz (b-21) | 10 + 10 | 100 | 78 |
| C + Tetraconazole (b-22) | 10 + 10 | 100 | 82 |
| C + Epoxiconazole (b-24) | 10 + 10 | 100 | 80 |
| C + Ipconazole (b-25) | 10 + 10 | 100 | 82 |
| C + Metconazole (b-26) | 10 + 10 | 100 | 82 |
| C + Propiconazole (b-27) | 10 + 10 | 97 | 80 |
| C + Cyproconazole (b-28) | 10 + 10 | 97 | 75 |
| C + Difenoconazole (b-29) | 10 + 10 | 97 | 80 |
| C + Fluquinconazole (b-30) | 10 + 10 | 100 | 80 |
| C + Flusilazole (b-31) | 10 + 10 | 97 | 75 |
| C + Penconazole (b-32) | 10 + 10 | 100 | 75 |
| C + Flutriafol (b-34) | 10 + 10 | 100 | 80 |
| C + Myclobutanil (b-35) | 10 + 10 | 100 | 75 |
| C + Imazalil (b-20) | 10 + 10 | 97 | 75 |
| C + Prochloraz (b-21) | 10 + 10 | 97 | 75 |
| Tetraconazole (b-22) | 10 | 40 | |
| Epoxiconazole (b-24) | 10 | 33 | |
| Ipconazole (b-25) | 10 | 40 | |
| Metconazole (b-26) | 10 | 40 | |
| Propiconazole (b-27) | 10 | 33 | |
| Cyproconazole (b-28) | 10 | 17 | |
| Difenoconazole (b-29) | 10 | 33 | |
| Fluquinconazole (b-30) | 10 | 33 | |
| Flusilazole (b-31) | 10 | 17 | |
| Penconazole (b-32) | 10 | 17 | |
| Flutriafol (b-34) | 10 | 33 | |
| Myclobutanil (b-35) | 10 | 17 | |
| Imazalil (b-20) | 10 | 17 | |
| Prochloraz (b-21) | 10 | 17 | |
| A | 10 | 73 | |
| B | 10 | 73 | |
| C | 10 | 70 | |

TABLE 2-5

| Effective ingredient in the preparation | Treatment concentration (ppm) | Preventive value | Theoretical value |
| --- | --- | --- | --- |
| A + Thiabendazole (b-60) | 10 + 50 | 100 | 87 |
| A + Benomyl (b-58) | 10 + 50 | 100 | 88 |
| A + Thiuram (b-68) | 10 + 50 | 100 | 90 |
| A + Metiram (b-67) | 10 + 50 | 100 | 90 |
| A + Folpet (b-70) | 10 + 50 | 100 | 92 |
| A + Pyrisoxazole (b-103) | 10 + 10 | 100 | 82 |
| B + Thiabendazole (b-60) | 10 + 50 | 100 | 87 |
| B + Benomyl (b-58) | 10 + 50 | 100 | 88 |
| B + Thiuram (b-68) | 10 + 50 | 100 | 90 |
| B + Metiram (b-67) | 10 + 50 | 100 | 90 |
| B + Folpet (b-70) | 10 + 50 | 100 | 92 |
| B + Pyrisoxazole (b-103) | 10 + 10 | 97 | 82 |
| C + Thiabendazole (b-60) | 10 + 50 | 100 | 87 |
| C + Benomyl (b-58) | 10 + 50 | 100 | 88 |
| C + Thiuram (b-68) | 10 + 50 | 100 | 90 |
| C + Metiram (b-67) | 10 + 50 | 100 | 90 |
| C + Folpet (b-70) | 10 + 50 | 100 | 92 |
| C + Pyrisoxazole (b-103) | 10 + 10 | 97 | 82 |
| Thiabendazole (b-60) | 50 | 57 | |
| Benomyl (b-58) | 50 | 60 | |
| Thiuram (b-68) | 50 | 67 | |
| Metiram (b-67) | 50 | 67 | |
| Folpet (b-70) | 50 | 73 | |
| Pyrisoxazole (b-103) | 10 | 40 | |
| A | 10 | 70 | |
| B | 10 | 70 | |
| C | 10 | 70 | |

TABLE 2-6

| Effective ingredient in the preparation | Treatment concentration (ppm) | Preventive value | Theoretical value |
| --- | --- | --- | --- |
| A + Fenpropimorph (b-65) | 10 + 50 | 97 | 78 |
| A + Tridemorph (b-66) | 10 + 50 | 100 | 78 |
| A + Metrafenone (b-82) | 10 + 50 | 100 | 73 |
| A + Quinoxyfen (b-63) | 10 + 50 | 100 | 78 |
| A + Flutianil (b-77) | 10 + 50 | 100 | 78 |
| A + Proquinazid (b-100) | 10 + 50 | 100 | 78 |
| A + Spiroxamine (b-101) | 10 + 50 | 100 | 78 |
| A + Fenpropidin (b-102) | 10 + 50 | 100 | 78 |
| A + Sulfur (b-96) | 10 + 50 | 100 | 73 |
| A + Chinomethionat (b-74) | 10 + 50 | 100 | 78 |
| B + Fenpropimorph (b-65) | 10 + 50 | 100 | 83 |
| B + Tridemorph (b-66) | 10 + 50 | 100 | 83 |
| B + Metrafenone (b-82) | 10 + 50 | 97 | 80 |
| B + Quinoxyfen (b-63) | 10 + 50 | 100 | 83 |
| B + Flutianil (b-77) | 10 + 50 | 100 | 83 |
| B + Proquinazid (b-100) | 10 + 50 | 100 | 83 |
| B + Spiroxamine (b-101) | 10 + 50 | 100 | 83 |
| B + Fenpropidin (b-102) | 10 + 50 | 100 | 83 |
| B + Sulfur (b-96) | 10 + 50 | 97 | 80 |
| B + Chinomethionat (b-74) | 10 + 50 | 100 | 83 |
| C + Fenpropimorph (b-65) | 10 + 50 | 100 | 81 |
| C + Tridemorph (b-66) | 10 + 50 | 100 | 81 |
| C + Metrafenone (b-82) | 10 + 50 | 100 | 77 |
| C + Quinoxyfen (b-63) | 10 + 50 | 100 | 81 |
| C + Flutianil (b-77) | 10 + 50 | 100 | 81 |
| C + Proquinazid (b-100) | 10 + 50 | 97 | 81 |
| C + Spiroxamine (b-101) | 10 + 50 | 100 | 81 |
| C + Fenpropidin (b-102) | 10 + 50 | 97 | 81 |
| C + Sulfur (b-96) | 10 + 50 | 100 | 77 |
| C + Chinomethionat (b-74) | 10 + 50 | 100 | 81 |
| Fenpropimorph (b-65) | 50 | 17 | |
| Tridemorph (b-66) | 50 | 17 | |
| Metrafenone (b-82) | 50 | 0 | |
| Quinoxyfen (b-63) | 50 | 17 | |
| Flutianil (b-77) | 50 | 17 | |
| Proquinazid (b-100) | 50 | 17 | |
| Spiroxamine (b-101) | 50 | 17 | |
| Fenpropidin (b-102) | 50 | 17 | |
| Sulfur (b-96) | 50 | 0 | |
| Chinomethionat (b-74) | 50 | 17 | |
| A | 10 | 73 | |
| B | 10 | 80 | |
| C | 10 | 77 | |

TABLE 2-7

| Effective ingredient in the preparation | Treatment concentration (ppm) | Preventive value | Theoretical value |
|---|---|---|---|
| A + Trifloxystrobin (b-55) | 10 + 10 | 100 | 78 |
| A + Bixafen (b-4) | 10 + 2 | 100 | 78 |
| A + Fluopyram (b-43) | 10 + 2 | 97 | 80 |
| A + Prothioconazole (b-23) | 10 + 2 | 97 | 78 |
| A + Triadimenol (b-33) | 10 + 50 | 97 | 72 |
| A + Pyrimethanil (b-62) | 10 + 10 | 97 | 78 |
| A + Dithianon (b-81) | 10 + 50 | 100 | 78 |
| B + Trifloxystrobin (b-55) | 10 + 10 | 97 | 78 |
| B + Bixafen (b-4) | 10 + 2 | 100 | 78 |
| B + Fluopyram (b-43) | 10 + 2 | 97 | 80 |
| B + Prothioconazole (b-23) | 10 + 2 | 100 | 78 |
| B + Triadimenol (b-33) | 10 + 50 | 100 | 72 |
| B + Pyrimethanil (b-62) | 10 + 10 | 100 | 78 |
| B + Dithianon (b-81) | 10 + 50 | 97 | 78 |
| C + Trifloxystrobin (b-55) | 10 + 10 | 100 | 78 |
| C + Bixafen (b-4) | 10 + 2 | 97 | 78 |
| C + Fluopyram (b-43) | 10 + 2 | 100 | 80 |
| C + Prothioconazole (b-23) | 10 + 2 | 97 | 78 |
| C + Triadimenol (b-33) | 10 + 50 | 100 | 72 |
| C + Pyrimethanil (b-62) | 10 + 10 | 100 | 78 |
| C + Dithianon (b-81) | 10 + 50 | 97 | 78 |
| Trifloxystrobin (b-55) | 10 | 33 | |
| Bixafen (b-4) | 2 | 33 | |
| Fluopyram (b-43) | 2 | 40 | |
| Prothioconazole (b-23) | 2 | 33 | |
| Triadimenol (b-33) | 50 | 17 | |
| Pyrimethanil (b-62) | 10 | 33 | |
| Dithianon (b-81) | 50 | 33 | |
| A | 10 | 67 | |
| B | 10 | 67 | |
| C | 10 | 67 | |

TABLE 2-8

| Effective ingredient in the preparation | Treatment concentration (ppm) | Preventive value | Theoretical value |
|---|---|---|---|
| A + Pyriofenone (b-83) | 10 + 10 | 97 | 78 |
| A + Compound of formula (XV)-1 (b-89) | 10 + 2 | 100 | 80 |
| A + Oxathiapiprolin (b-84) | 10 + 50 | 97 | 78 |
| A + Compound of formula (XIX) (b-94) | 10 + 0.4 | 100 | 80 |
| A + Compound of formula (XVII) (b-91) | 10 + 2 | 100 | 80 |
| A + Compound of formula (III) (b-8) | 10 + 2 | 100 | 80 |
| A + Compound of formula (IV) (b-9) | 10 + 2 | 100 | 80 |
| A + Fluxapyroxad (b-1) | 10 + 2 | 100 | 78 |
| A + Benzovindiflupyr (b-2) | 10 + 2 | 97 | 80 |
| A + Carbendazim (b-59) | 10 + 2 | 100 | 80 |
| A + Pyribencarb (b-98) | 10 + 2 | 97 | 80 |
| A + Pyraziflumid (b-49) | 10 + 2 | 97 | 80 |
| B + Pyriofenone (b-83) | 10 + 10 | 93 | 78 |
| B + Compound of formula (XV)-1 (b-89) | 10 + 2 | 100 | 80 |
| B + Oxathiapiprolin (b-84) | 10 + 50 | 100 | 78 |
| B + Compound of formula (XIX) (b-94) | 10 + 0.4 | 97 | 80 |
| B + Compound of formula (XVII) (b-91) | 10 + 2 | 100 | 80 |
| B + Compound of formula (III) (b-8) | 10 + 2 | 100 | 80 |
| B + Compound of formula (IV) (b-9) | 10 + 2 | 97 | 80 |
| B + Fluxapyroxad (b-1) | 10 + 2 | 97 | 78 |
| B + Benzovindiflupyr (b-2) | 10 + 2 | 97 | 80 |
| B + Carbendazim (b-59) | 10 + 2 | 100 | 80 |
| B + Pyribencarb (b-98) | 10 + 2 | 100 | 80 |
| B + Pyraziflumid (b-49) | 10 + 2 | 97 | 80 |
| C + Pyriofenone (b-83) | 10 + 10 | 100 | 80 |
| C + Compound of formula (XV)-1 (b-89) | 10 + 2 | 100 | 82 |
| C + Oxathiapiprolin (b-84) | 10 + 50 | 97 | 80 |
| C + Compound of formula (XIX) (b-94) | 10 + 0.4 | 100 | 82 |
| C + Compound of formula (XVII) (b-91) | 10 + 2 | 100 | 82 |
| C + Compound of formula (III) (b-8) | 10 + 2 | 100 | 82 |
| C + Compound of formula (IV) (b-9) | 10 + 2 | 100 | 82 |
| C + Fluxapyroxad (b-1) | 10 + 2 | 100 | 80 |
| C + Benzovindiflupyr (b-2) | 10 + 2 | 100 | 82 |
| C + Carbendazim (b-59) | 10 + 2 | 100 | 82 |
| C + Pyribencarb (b-98) | 10 + 2 | 97 | 82 |
| C + Pyraziflumid (b-49) | 10 + 2 | 97 | 82 |
| Pyriofenone (b-83) | 10 | 33 | |
| Compound of formula (XV)-1 (b-89) | 2 | 40 | |
| Oxathiapiprolin (b-84) | 50 | 33 | |
| Compound of formula (XIX) (b-94) | 0.4 | 40 | |
| Compound of formula (XVII) (b-91) | 2 | 40 | |
| Compound of formula (III) (b-8) | 2 | 40 | |
| Compound of formula (IV) (b-9) | 2 | 40 | |
| Fluxapyroxad (b-1) | 2 | 33 | |
| Benzovindiflupyr (b-2) | 2 | 40 | |
| Carbendazim (b-59) | 2 | 40 | |
| Pyribencarb (b-98) | 2 | 40 | |
| Pyraziflumid (b-49) | 2 | 40 | |
| A | 10 | 40 | |
| B | 10 | 40 | |
| C | 10 | 40 | |

TABLE 2-9

| Effective ingredient in the preparation | Treatment concentration (ppm) | Preventive value | Theoretical value |
|---|---|---|---|
| A + Phosphorous acid (b-105) | 10 + 250 | 93 | 82 |
| A + Propineb (b-69) | 10 + 50 | 93 | 82 |
| A + Compound of (V) (b-36) | 10 + 10 | 100 | 84 |
| A + Compound of (XIV) (b-88) | 10 + 0.4 | 97 | 87 |
| A + Compound of (XI)-1 (b-85) | 10 + 10 | 97 | 87 |
| A + Compound of (XI)-2 (b-85) | 10 + 10 | 97 | 87 |
| A + Compound of (XVIII) (b-92) | 10 + 0.4 | 97 | 87 |
| A + D-tagatose (b-93) | 10 + 5000 | 93 | 82 |
| B + Phosphorous acid (b-105) | 10 + 250 | 97 | 82 |
| B + Propineb (b-69) | 10 + 50 | 97 | 82 |
| B + Compound of (V) (b-36) | 10 + 10 | 100 | 84 |
| B + Compound of (XIV) (b-88) | 10 + 0.4 | 97 | 87 |
| B + Compound of (XI)-1 (b-85) | 10 + 10 | 97 | 87 |
| B + Compound of (XI)-2 (b-85) | 10 + 10 | 97 | 87 |
| B + Compound of (XVIII) (b-92) | 10 + 0.4 | 97 | 87 |
| B + D-tagatose (b-93) | 10 + 5000 | 93 | 82 |
| C + Phosphorous acid (b-105) | 10 + 250 | 93 | 82 |
| C + Propineb (b-69) | 10 + 50 | 93 | 82 |
| C + Compound of (V) (b-36) | 10 + 10 | 97 | 84 |
| C + Compound of (XIV) (b-88) | 10 + 0.4 | 97 | 87 |
| C + Compound of (XI)-1 (b-85) | 10 + 10 | 97 | 87 |
| C + Compound of (XI)-2 (b-85) | 10 + 10 | 97 | 87 |
| C + Compound of (XVIII) (b-92) | 10 + 0.4 | 93 | 87 |
| C + D-tagatose (b-93) | 10 + 5000 | 93 | 82 |
| Phosphorous acid (b-105) | 250 | 33 | |
| Propineb (b-69) | 50 | 33 | |
| Compound of (V) (b-36) | 10 | 40 | |
| Compound of (XIV) (b-88) | 0.4 | 50 | |
| Compound of (XI)-1 (b-85) | 10 | 50 | |
| Compound of (XI)-2 (b-85) | 10 | 50 | |
| Compound of (XVIII) (b-92) | 0.4 | 50 | |
| D-tagatose (b-93) | 5000 | 33 | |
| A | 10 | 73 | |
| B | 10 | 73 | |
| C | 10 | 73 | |

Based on the results shown in Tables 2-1 to 2-9 above, synergistic effects were determined to be obtained when Compound A, Compound B or Compound C is used in combination with a compound of group b. Furthermore, there were no symptoms of chemical damage observed on the plant bodies or tomatoes (variety: Ohgata Fukuju) even when Compound A, Compound B or Compound C was used in combination with a compound of group b.

Comparative Example 1 Tomato Gray Mold Preventive Test

Wettable powder prepared in compliance with Comparative Preparation Example 4 containing the compounds indicated in Table 2-10 were sprayed to the tomato leaves, a conidia suspension of *Botrytis cinerea* was inoculated onto the plants, and the controlling effects were examined in a manner similar to Test Example 1. The results and theoretical values as determined according to Colby's formula are shown in Table 2-10.

TABLE 2-10

| Effective ingredient in the preparation | Treatment concentration (ppm) | Preventive value | Theoretical value |
| --- | --- | --- | --- |
| A + Diclocymet | 10 + 50 | 60 | 72 |
| A + Carpropamid | 10 + 50 | 67 | 72 |
| A + Tolclofos-methyl | 10 + 50 | 67 | 72 |
| A + Oxolinic acid | 10 + 50 | 60 | 72 |
| B + Diclocymet | 10 + 50 | 67 | 72 |
| B + Carpropamid | 10 + 50 | 67 | 72 |
| B + Tolclofos-methyl | 10 + 50 | 60 | 72 |
| B + Oxolinic acid | 10 + 50 | 60 | 72 |
| C + Diclocymet | 10 + 50 | 60 | 72 |
| C + Carpropamid | 10 + 50 | 60 | 72 |
| C + Tolclofos-methyl | 10 + 50 | 60 | 72 |
| C + Oxolinic acid | 10 + 50 | 63 | 72 |
| Diclocymet | 50 | 17 | |
| Carpropamid | 50 | 17 | |
| Tolclofos-methyl | 50 | 17 | |
| Oxolinic acid | 50 | 17 | |
| A | 10 | 67 | |
| B | 10 | 67 | |
| C | 10 | 67 | |

Based on the results shown in Tables 2-10 above, even if these compounds are used in combination with Compound A, Compound B or Compound C, the controlling effects were under their theoretical values and the action resulting from combining two types of active ingredients is indicated to be antagonistic.

Test Example 2 Rice Blast Preventive Test

Rice plants (variety: Sachikaze) planted in plastic pots having a diameter of 5 cm were grown indoors to the third to fourth leaf stage. Wettable powder containing the compounds indicated in Table 3 were sprayed in the same manner as in Test Example 1, and after the chemical had dried, a conidia suspension prepared from *Pyricularia oryzae* which had been previously cultured in oatmeal medium was inoculated by spraying onto the plants. Following inoculation, the pots were placed in the humidified chamber of an artificial inoculation room (20° C. to 23° C.), and taken out on the next day and then transferred to a greenhouse. Control effects were examined 7 days after inoculation. During the examination, the number of lesions on the rice per pot was determined in accordance with the following incidence degree indicators, and control values and theoretical values as determined according to Colby's formula were calculated in the same manner as in Test Example 1. The results are shown in Tables 3-1 to 3-3.

| Indicator | Incidence Degree |
| --- | --- |
| 0 | No lesions |
| 0.5 | 1 to 2 lesions |
| 1 | 3 to 5 lesions |
| 2 | 6 to 10 lesions |
| 3 | 11 to 20 lesions |
| 4 | 21 to 30 lesions |
| 5 | 31 to 40 lesions |
| 6 | 41 or more lesions or withered |

TABLE 3-1

| Effective ingredient in the preparation | Treatment concentration (ppm) | Control value | Theoretical value |
| --- | --- | --- | --- |
| A + Fluxapyroxad (b-1) | 10 + 2 | 83 | 72 |
| A + Compound of formula (II) (b-3) | 10 + 2 | 92 | 72 |
| A + Isofetamid (b-47) | 10 + 10 | 83 | 72 |
| A + Picarbutrazox (b-78) | 10 + 0.4 | 83 | 72 |
| A + Pyraziflumid (b-49) | 10 + 2 | 83 | 72 |
| A + Compound of formula (XIV) (b-88) | 10 + 2 | 92 | 83 |
| A + Compound of formula (VII)-1 (b-38) | 10 + 2 | 92 | 83 |
| B + Fluxapyroxad (b-1) | 10 + 2 | 92 | 72 |
| B + Compound of formula (II) (b-3) | 10 + 2 | 92 | 72 |
| B + Isofetamid (b-47) | 10 + 10 | 92 | 72 |
| B + Picarbutrazox (b-78) | 10 + 0.4 | 83 | 72 |
| B + Pyraziflumid (b-49) | 10 + 2 | 83 | 72 |
| B + Compound of formula (XIV) (b-88) | 10 + 2 | 100 | 83 |
| B + Compound of formula (VII)-1 (b-38) | 10 + 2 | 100 | 83 |
| C + Fluxapyroxad (b-1) | 10 + 2 | 92 | 72 |
| C + Compound of formula (II) (b-3) | 10 + 2 | 92 | 72 |
| C + Isofetamid (b-47) | 10 + 10 | 92 | 72 |
| C + Picarbutrazox (b-78) | 10 + 0.4 | 83 | 72 |
| C + Pyraziflumid (b-49) | 10 + 2 | 92 | 72 |
| C + Compound of formula (XIV) (b-88) | 10 + 2 | 100 | 83 |
| C + Compound of formula (VII)-1 (b-38) | 10 + 2 | 100 | 83 |
| Fluxapyroxad (b-1) | 2 | 17 | |
| Compound of formula (II) (b-3) | 2 | 17 | |
| Isofetamid (b-47) | 10 | 17 | |
| Picarbutrazox (b-78) | 0.4 | 17 | |
| Pyraziflumid (b-49) | 2 | 17 | |
| Compound of formula (XIV) (b-88) | 2 | 50 | |
| Compound of formula (VII)-1 (b-38) | 2 | 50 | |
| A | 10 | 67 | |
| B | 10 | 67 | |
| C | 10 | 67 | |

TABLE 3-2

| Effective ingredient in the preparation | Treatment concentration (ppm) | Preventive value | Theoretical value |
| --- | --- | --- | --- |
| A + Fluoxastrobin (b-51) | 10 + 10 | 97 | 89 |
| A + Dimoxystrobin (b-52) | 10 + 10 | 100 | 93 |
| A + Orysastrobin (b-53) | 10 + 10 | 100 | 89 |
| B + Fluoxastrobin (b-51) | 10 + 10 | 100 | 89 |
| B + Dimoxystrobin (b-52) | 10 + 10 | 100 | 93 |
| B + Orysastrobin (b-53) | 10 + 10 | 100 | 89 |
| C + Fluoxastrobin (b-51) | 10 + 10 | 97 | 89 |
| C + Dimoxystrobin (b-52) | 10 + 10 | 100 | 93 |
| C + Orysastrobin (b-53) | 10 + 10 | 100 | 89 |
| Fluoxastrobin (b-51) | 10 | 60 | |
| Dimoxystrobin (b-52) | 10 | 73 | |
| Orysastrobin (b-53) | 10 | 60 | |
| A | 10 | 73 | |
| B | 10 | 73 | |
| C | 10 | 73 | |

TABLE 3-3

| Effective ingredient in the preparation | Treatment concentration (ppm) | Preventive value | Theoretical value |
|---|---|---|---|
| A + Tiadinil (b-45) | 10 + 10 | 100 | 89 |
| A + Probenazole (b-73) | 10 + 10 | 100 | 89 |
| A + Tebufloquin (b-64) | 10 + 10 | 100 | 93 |
| A + Isoprothiolane (b-71) | 10 + 50 | 100 | 87 |
| A + Pyroquilon (b-104) | 10 + 50 | 100 | 91 |
| A + Pencycuron (b-76) | 10 + 250 | 93 | 84 |
| B + Tiadinil (b-45) | 10 + 10 | 100 | 89 |
| B + Probenazole (b-73) | 10 + 10 | 100 | 89 |
| B + Tebufloquin (b-64) | 10 + 10 | 100 | 93 |
| B + Isoprothiolane (b-71) | 10 + 50 | 100 | 87 |
| B + Pyroquilon (b-104) | 10 + 50 | 97 | 91 |
| B + Pencycuron (b-76) | 10 + 250 | 100 | 84 |
| C + Tiadinil (b-45) | 10 + 10 | 100 | 89 |
| C + Probenazole (b-73) | 10 + 10 | 100 | 89 |
| C + Tebufloquin (b-64) | 10 + 10 | 100 | 93 |
| C + Isoprothiolane (b-71) | 10 + 50 | 100 | 87 |
| C + Pyroquilon (b-104) | 10 + 50 | 97 | 91 |
| C + Pencycuron (b-76) | 10 + 250 | 97 | 84 |
| Tiadinil (b-45) | 10 | 60 | |
| Probenazole (b-73) | 10 | 60 | |
| Tebufloquin (b-64) | 10 | 73 | |
| Isoprothiolane (b-71) | 50 | 50 | |
| Pyroquilon (b-104) | 50 | 67 | |
| Pencycuron (b-76) | 250 | 40 | |
| A | 10 | 73 | |
| B | 10 | 73 | |
| C | 10 | 73 | |

TABLE 3-4

| Effective ingredient in the preparation | Treatment concentration (ppm) | Preventive value | Theoretical value |
|---|---|---|---|
| A + Benzovindiflupyr (b-2) | 10 + 2 | 100 | 80 |
| A + Bixafen (b-4) | 10 + 10 | 97 | 78 |
| A + Picoxystrobin (b-16) | 10 + 2 | 100 | 83 |
| A + Trifloxystrobin (b-55) | 10 + 2 | 100 | 86 |
| A + Pyraclostrobin (b-19) | 10 + 2 | 100 | 80 |
| A + Fluopyram (b-43) | 10 + 10 | 100 | 80 |
| A + Prothioconazole (b-23) | 10 + 10 | 100 | 78 |
| A + Triadimenol (b-33) | 10 + 250 | 97 | 78 |
| A + Pyrimethanil (b-62) | 10 + 50 | 100 | 78 |
| A + Isotianil (b-46) | 10 + 10 | 100 | 83 |
| A + Metominostrobin (b-54) | 10 + 2 | 100 | 80 |
| A + Acibenzolar-S-methyl (b-72) | 10 + 10 | 100 | 87 |
| A + Compound of formula (XIX) (b-94) | 10 + 0.4 | 100 | 83 |
| B + Benzovindiflupyr (b-2) | 10 + 2 | 100 | 80 |
| B + Bixafen (b-4) | 10 + 10 | 100 | 78 |
| B + Picoxystrobin (b-16) | 10 + 2 | 100 | 83 |
| B + Trifloxystrobin (b-55) | 10 + 2 | 100 | 86 |
| B + Pyraclostrobin (b-19) | 10 + 2 | 100 | 80 |
| B + Fluopyram (b-43) | 10 + 10 | 100 | 80 |
| B + Prothioconazole (b-23) | 10 + 10 | 100 | 78 |
| B + Triadimenol (b-33) | 10 + 250 | 97 | 78 |
| B + Pyrimethanil (b-62) | 10 + 50 | 97 | 78 |
| B + Isotianil (b-46) | 10 + 10 | 100 | 83 |
| B + Metominostrobin (b-54) | 10 + 2 | 100 | 80 |
| B + Acibenzolar-S-methyl (b-72) | 10 + 10 | 100 | 87 |
| B + Compound of formula (XIX) (b-94) | 10 + 0.4 | 100 | 83 |
| C + Benzovindiflupyr (b-2) | 10 + 2 | 100 | 80 |
| C + Bixafen (b-4) | 10 + 10 | 97 | 78 |
| C + Picoxystrobin (b-16) | 10 + 2 | 100 | 83 |
| C + Trifloxystrobin (b-55) | 10 + 2 | 100 | 86 |
| C + Pyraclostrobin (b-19) | 10 + 2 | 100 | 80 |
| C + Fluopyram (b-43) | 10 + 10 | 97 | 80 |
| C + Prothioconazole (b-23) | 10 + 10 | 100 | 78 |
| C + Triadimenol (b-33) | 10 + 250 | 97 | 78 |
| C + Pyrimethanil (b-62) | 10 + 50 | 97 | 78 |
| C + Isotianil (b-46) | 10 + 10 | 100 | 83 |
| C + Metominostrobin (b-54) | 10 + 2 | 100 | 80 |
| C + Acibenzolar-S-methyl (b-72) | 10 + 10 | 100 | 87 |
| C + Compound of formula (XIX) (b-94) | 10 + 0.4 | 97 | 83 |
| Benzovindiflupyr (b-2) | 10 + 2 | 40 | |
| Bixafen (b-4) | 10 + 10 | 33 | |
| Picoxystrobin (b-16) | 10 + 2 | 50 | |
| Trifloxystrobin (b-55) | 10 + 2 | 57 | |
| Pyraclostrobin (b-19) | 10 + 2 | 40 | |
| Fluopyram (b-43) | 10 + 10 | 40 | |
| Prothioconazole (b-23) | 10 + 10 | 33 | |
| Triadimenol (b-33) | 10 + 250 | 33 | |
| Pyrimethanil (b-62) | 10 + 50 | 33 | |
| Isotianil (b-46) | 10 + 10 | 50 | |
| Metominostrobin (b-54) | 10 + 2 | 40 | |
| Acibenzolar-S-methyl (b-72) | 10 + 10 | 60 | |
| Compound of formula (XIX) (b-94) | 10 + 0.4 | 50 | |
| A | 10 | 67 | |
| B | 10 | 67 | |
| C | 10 | 67 | |

Based on the results shown in Tables 3-1 to 3-4 above, synergistic effects were determined to be obtained when Compound A, Compound B or Compound C is used in combination with a compound of group b. Furthermore, there were no symptoms of chemical damage observed on the plant bodies or rice (variety: Sachikaze) even when Compound A, Compound B or Compound C was used in combination with a compound of group b.

Comparative Example 2 Rice Blast Preventive Test

Wettable powder prepared in compliance with Comparative Preparation Example 4 containing the compounds indicated in Table 3-5 were sprayed to the rice plant leaves, a conidia suspension of *Pyricularia oryzae* was inoculated onto the plants, and the controlling effects were examined in a manner similar to Test Example 2. The results and theoretical values as determined according to Colby's formula are shown in Table 3-5.

TABLE 3-5

| Effective ingredient in the preparation | Treatment concentration (ppm) | Preventive value | Theoretical value |
|---|---|---|---|
| A + Diclocymet | 10 + 0.4 | 83 | 89 |
| A + Carpropamid | 10 + 0.4 | 77 | 89 |
| A + Tolclofos-methyl | 10 + 10 | 67 | 78 |
| A + Oxolinic acid | 10 + 50 | 67 | 78 |
| B + Diclocymet | 10 + 0.4 | 80 | 89 |
| B + Carpropamid | 10 + 0.4 | 77 | 89 |
| B + Tolclofos-methyl | 10 + 10 | 67 | 78 |
| B + Oxolinic acid | 10 + 50 | 67 | 78 |
| C + Diclocymet | 10 + 0.4 | 73 | 89 |
| C + Carpropamid | 10 + 0.4 | 73 | 89 |
| C + Tolclofos-methyl | 10 + 10 | 67 | 78 |
| C + Oxolinic acid | 10 + 50 | 67 | 78 |
| Diclocymet | 0.4 | 67 | |
| Carpropamid | 0.4 | 67 | |
| Tolclofos-methyl | 10 | 33 | |
| Oxolinic acid | 50 | 33 | |
| A | 10 | 67 | |
| B | 10 | 67 | |
| C | 10 | 67 | |

Based on the results shown in Tables 3-5 above, even if these compounds are used in combination with Compound A, Compound B or Compound C, the controlling effects were under their theoretical values and the action resulting from combining two types of active ingredients is indicated to be antagonistic.

Test Example 3 Barley Powdery Mildew Preventive Test

Barley plants (variety: Akashinriki) planted in plastic pots having a diameter of 5 cm were grown indoors to the second to fourth leaf stage. Wettable powder containing the compounds indicated in Table 4 were sprayed in the same manner as in Test Example 1, and after the chemical had dried, conidia of *Blumeria graminis* was inoculated onto the leaves. Following inoculation, the pots were transferred to a constant-temperature chamber (20° C. to 25° C.), and control effects were examined 8 days after inoculation. During the examination, the percentage of affected area exhibiting lesions on the barley plants per pot was determined in accordance with the following incidence degree indicators, and control values and theoretical values as determined according to Colby's formula were calculated in the same manner as in Test Example 1. The results are shown in Table 4.

Incidence Degree Indicators

| Indicator | Incidence Degree |
|---|---|
| 0 | No lesions |
| 0.5 | Lesion area of about 1% to 2% |
| 1 | Lesion area of less than 5% |
| 2 | Lesion area of less than 25% |
| 3 | Lesion area of less than 50% |
| 4 | Lesion area of less than 75% |
| 5 | Lesion area of 75% or more |

TABLE 4

| Effective ingredient in the preparation | Treatment concentration (ppm) | Control value | Theoretical value |
|---|---|---|---|
| A + Fluxapyroxad (b-1) | 10 + 2 | 67 | 63 |
| A + Benzovindiflupyr (b-2) | 10 + 2 | 56 | 53 |
| A + Compound of formula (II) (b-3) | 10 + 2 | 78 | 69 |
| A + Isofetamid (b-47) | 10 + 10 | 86 | 69 |
| A + Compound of formula (XIV) (b-88) | 10 + 2 | 72 | 58 |
| A + Compound of formula (VII)-1 (b-38) | 10 + 2 | 97 | 82 |
| B + Fluxapyroxad (b-1) | 10 + 2 | 67 | 63 |
| B + Benzovindiflupyr (b-2) | 10 + 2 | 67 | 53 |
| B + Compound of formula (II) (b-3) | 10 + 2 | 72 | 69 |
| B + Isofetamid (b-47) | 10 + 10 | 83 | 69 |
| B + Compound of formula (XIV) (b-88) | 10 + 2 | 61 | 58 |
| B + Compound of formula (VII)-1 (b-38) | 10 + 2 | 89 | 82 |
| C + Fluxapyroxad (b-1) | 10 + 2 | 86 | 63 |
| C + Benzovindiflupyr (b-2) | 10 + 2 | 72 | 53 |
| C + Compound of formula (II) (b-3) | 10 + 2 | 78 | 69 |
| C + Isofetamid (b-47) | 10 + 10 | 92 | 69 |
| C + Compound of formula (XIV) (b-88) | 10 + 2 | 61 | 58 |
| C + Compound of formula (VII)-1 (b-38) | 10 + 2 | 83 | 82 |
| Fluxapyroxad (b-1) | 2 | 61 | |
| Benzovindiflupyr (b-2) | 2 | 50 | |
| Compound of formula (II) (b-3) | 2 | 67 | |
| Isofetamid (b-47) | 10 | 67 | |
| Compound of formula (XIV) (b-88) | 2 | 56 | |
| Compound of formula (VII)-1 (b-38) | 2 | 81 | |
| A | 10 | 6 | |
| B | 10 | 6 | |
| C | 10 | 6 | |

Based on the results shown in Table 4 above, synergistic effects were determined to be obtained when Compound A, Compound B or Compound C is used in combination with a compound of group b. Furthermore, there were no symptoms of chemical damage observed on the plant bodies or barley (variety: Akashinriki) even when Compound A, Compound B or Compound C was used in combination with a compound of group b.

Test Example 4 Wheat Brown Rust Preventive Test

Wheat plants (variety: Norin 61 gou) planted in plastic pots having a diameter of 5 cm were grown indoors to the second to fourth leaf stage. Wettable powder containing the compounds indicated in Table 5 were sprayed in the same manner as in Test Example 1, and after the chemical had dried, a conidia suspension of *Puccinia recondita* was inoculated onto the leaves. Following inoculation, the pots were placed in the humidified chamber of an artificial inoculation room (20° C. to 23° C.), removed on the following day and then transferred to a greenhouse. Control effects were examined 8 days after inoculation. During the examination, the number of lesions on five leaves of the wheat plants was determined in accordance with the following incidence degree indicators, and control values and theoretical values as determined according to Colby's formula were calculated in the same manner as in Test Example 1. The results are shown in Table 5.

| Indicator | Incidence Degree |
|---|---|
| 0 | No lesions |
| 0.5 | 1 to 2 lesions |
| 1 | 3 to 5 lesions |
| 2 | 6 to 20 lesions |
| 3 | 21 to 50 lesions |
| 4 | 51 to 80 lesions |
| 5 | 81 to 100 lesions |
| 6 | 101 or more lesions |

TABLE 5

| Effective ingredient in the preparation | Treatment concentration (ppm) | Control value | Theoretical value |
|---|---|---|---|
| A + Fluxapyroxad (b-1) | 10 + 2 | 89 | 75 |
| A + Isofetamid (b-47) | 10 + 10 | 22 | 14 |
| A + Picarbutrazox (b-78) | 10 + 0.4 | 22 | 14 |
| A + Pyraziflumid (b-49) | 10 + 2 | 92 | 86 |
| A + Compound of formula (XIV) (b-88) | 10 + 2 | 53 | 48 |
| A + Compound of formula (VII)-1 (b-38) | 10 + 2 | 82 | 73 |
| B + Fluxapyroxad (b-1) | 10 + 2 | 86 | 74 |
| B + Isofetamid (b-47) | 10 + 10 | 53 | 8 |
| B + Picarbutrazox (b-78) | 10 + 0.4 | 53 | 8 |
| B + Pyraziflumid (b-49) | 10 + 2 | 94 | 86 |
| B + Compound of formula (XIV) (b-88) | 10 + 2 | 72 | 45 |
| B + Compound of formula (VII)-1 (b-38) | 10 + 2 | 90 | 71 |
| C + Fluxapyroxad (b-1) | 10 + 2 | 90 | 75 |
| C + Isofetamid (b-47) | 10 + 10 | 47 | 11 |
| C + Picarbutrazox (b-78) | 10 + 0.4 | 50 | 11 |
| C + Pyraziflumid (b-49) | 10 + 2 | 92 | 86 |
| C + Compound of formula (XIV) (b-88) | 10 + 2 | 64 | 47 |

TABLE 5-continued

| Effective ingredient in the preparation | Treatment concentration (ppm) | Control value | Theoretical value |
|---|---|---|---|
| C + Compound of formula (VII)-1 (b-38) | 10 + 2 | 78 | 72 |
| Fluxapyroxad (b-1) | 2 | 72 | |
| Isofetamid (b-47) | 10 | 3 | |
| Picarbutrazox (b-78) | 0.4 | 3 | |
| Pyraziflumid (b-49) | 2 | 85 | |
| Compound of formula (XIV) (b-88) | 2 | 42 | |
| Compound of formula (VII)-1 (b-38) | 2 | 69 | |
| A | 10 | 11 | |
| B | 10 | 6 | |
| C | 10 | 8 | |

Based on the results shown in Table 5 above, synergistic effects were determined to be obtained when Compound A, Compound B or Compound C is used in combination with a compound of group b. Furthermore, there were no symptoms of chemical damage observed on the plant bodies or wheat (variety: Norin No. 61) even when Compound A, Compound B or Compound C was used in combination with a compound of group b.

Test Example 5 Tomato Late Blight Preventive Test

Tomato plants (variety: Ohgata Fukuju) planted in plastic pots having a diameter of 5 cm were grown indoors to the second to third leaf stage. Wettable powders containing the compounds indicated in Table 6 were sprayed in the same manner as in Test Example 1, and after the chemical had dried, a zoospores and zoosporangium suspension of *Phytophthora infestans* was inoculated by spraying onto the plants. Following inoculation, the pots were placed in the humidified chamber of an artificial inoculation room (20° C. to 22° C.) and then transferred to a greenhouse on the following day followed by examining control effects 5 days after inoculation. The percentage of affected area exhibiting lesions on a single tomato leaf was determined in accordance with the same indicators as used in Test Example 1, and control values and theoretical values as determined according to Colby's formula were calculated in the same manner as in Test Example 1. The results are shown in Tables 6-1 to 6-2.

TABLE 6-1

| Effective ingredient in the preparation | Treatment concentration (ppm) | Control value | Theoretical value |
|---|---|---|---|
| A + Picarbutrazox (b-78) | 10 + 0.4 | 96 | 77 |
| B + Picarbutrazox (b-78) | 10 + 0.4 | 96 | 78 |
| C + Picarbutrazox (b-78) | 10 + 0.4 | 94 | 76 |
| Picarbutrazox (b-78) | 0.4 | 75 | |
| A | 10 | 8 | |
| B | 10 | 13 | |
| C | 10 | 4 | |

TABLE 6-2

| Effective ingredient in the preparation | Treatment concentration (ppm) | Preventive value | Theoretical value |
|---|---|---|---|
| A + Mandipropamid (b-44) | 10 + 0.08 | 97 | 78 |
| A + Fluopicolide (b-40) | 10 + 2 | 97 | 60 |
| A + Benalaxyl-M (b-75) | 10 + 2 | 87 | 60 |
| A + Iprovalicarb (b-50) | 10 + 2 | 90 | 67 |
| A + Amisulbrom (b-97) | 10 + 0.08 | 83 | 67 |
| A + Ametoctradin (b-95) | 10 + 2 | 87 | 60 |
| A + Zoxamide (b-39) | 10 + 0.4 | 83 | 60 |
| A + Hymexazol (b-106) | 10 + 250 | 73 | 56 |
| B + Mandipropamid (b-44) | 10 + 0.08 | 93 | 78 |
| B + Fluopicolide (b-40) | 10 + 2 | 87 | 60 |
| B + Benalaxyl-M (b-75) | 10 + 2 | 90 | 60 |
| B + Iprovalicarb (b-50) | 10 + 2 | 90 | 67 |
| B + Amisulbrom (b-97) | 10 + 0.08 | 87 | 67 |
| B + Ametoctradin (b-95) | 10 + 2 | 83 | 60 |
| B + Zoxamide (b-39) | 10 + 0.4 | 87 | 60 |
| B + Hymexazol (b-106) | 10 + 250 | 73 | 56 |
| C + Mandipropamid (b-44) | 10 + 0.08 | 97 | 80 |
| C + Fluopicolide (b-40) | 10 + 2 | 93 | 64 |
| C + Benalaxyl-M (b-75) | 10 + 2 | 90 | 64 |
| C + Iprovalicarb (b-50) | 10 + 2 | 90 | 70 |
| C + Amisulbrom (b-97) | 10 + 0.08 | 90 | 70 |
| C + Ametoctradin (b-95) | 10 + 2 | 90 | 64 |
| C + Zoxamide (b-39) | 10 + 0.4 | 87 | 64 |
| C + Hymexazol (b-106) | 10 + 250 | 83 | 60 |
| Mandipropamid (b-44) | 0.08 | 67 | |
| Fluopicolide (b-40) | 2 | 40 | |
| Benalaxyl-M (b-75) | 2 | 40 | |
| Iprovalicarb (b-50) | 2 | 50 | |
| Amisulbrom (b-97) | 0.08 | 50 | |
| Ametoctradin (b-95) | 2 | 40 | |
| Zoxamide (b-39) | 0.4 | 40 | |
| Hymexazol (b-106) | 250 | 33 | |
| A | 10 | 33 | |
| B | 10 | 33 | |
| C | 10 | 40 | |

TABLE 6-3

| Effective ingredient in the preparation | Treatment concentration (ppm) | Preventive value | Theoretical value |
|---|---|---|---|
| A + Oxathiapiprolin (b-84) | 10 + 0.0016 | 100 | 82 |
| A + Dithianon (b-81) | 10 + 2 | 87 | 64 |
| A + D-tagatose (b-93) | 10 + 5000 | 90 | 68 |
| B + Oxathiapiprolin (b-84) | 10 + 0.0016 | 100 | 80 |
| B + Dithianon (b-81) | 10 + 2 | 87 | 60 |
| B + D-tagatose (b-93) | 10 + 5000 | 93 | 64 |
| C + Oxathiapiprolin (b-84) | 10 + 0.0016 | 100 | 79 |
| C + Dithianon (b-81) | 10 + 2 | 87 | 58 |
| C + D-tagatose (b-93) | 10 + 5000 | 90 | 62 |
| Oxathiapiprolin (b-84) | 0.0016 | 67 | |
| Dithianon (b-81) | 2 | 33 | |
| D-tagatose (b-93) | 5000 | 40 | |
| A | 10 | 47 | |
| B | 10 | 40 | |
| C | 10 | 37 | |

Based on the results shown in Tables 6-1 and 6-3 above, synergistic effects were determined to be obtained when Compound A, Compound B or Compound C is used in combination with a compound of group b. Furthermore, there were no symptoms of chemical damage observed on the plant bodies or tomatoes (variety: Ohgata Fukuju) even when Compound A, Compound B or Compound C was used in combination with a compound of group b.

Test Example 6 Cucumber Powdery Mildew Preventive Test

In a greenhouse, cucumber (variety: Sagamihanshiro) planted in a plastic pot having a diameter of 5 cm was grown to the 3rd to 5th-leaf stage. Spray was carried out in the same manner as in Test example 1, and 3 days after the spray, a conidia suspension prepared from *Sphaerotheca fuliginea* were inoculated on the leaf surface. After inoculation, the pots were placed in a thermostatic greenhouse (20 to 25° C.), and controlling effects were examined after 7 days from the inoculation. In the examination, a ratio of lesion area occupied per one leaf of cucumber was determined according to the same index as in Test example 1, and the control value and the theoretical value according to Colby's formula were similarly calculated. The results are shown in Table 7-1 to 7-8

TABLE 7-1

| Effective ingredient in the preparation | Treatment concentration (ppm) | Control value | Theoretical value |
|---|---|---|---|
| A + Fluoxastrobin (b-51) | 10 + 2 | 93 | 73 |
| A + Dimoxystrobin (b-52) | 10 + 2 | 93 | 73 |
| A + Orysastrobin (b-53) | 10 + 2 | 97 | 60 |
| B + Fluoxastrobin (b-51) | 10 + 2 | 87 | 73 |
| B + Dimoxystrobin (b-52) | 10 + 2 | 93 | 73 |
| B + Orysastrobin (b-53) | 10 + 2 | 90 | 60 |
| C + Fluoxastrobin (b-51) | 10 + 2 | 97 | 73 |
| C + Dimoxystrobin (b-52) | 10 + 2 | 93 | 73 |
| C + Orysastrobin (b-53) | 10 + 2 | 97 | 60 |
| Fluoxastrobin (b-51) | 2 | 60 | |
| Dimoxystrobin (b-52) | 2 | 60 | |
| Orysastrobin (b-53) | 2 | 40 | |
| A | 10 | 33 | |
| B | 10 | 33 | |
| C | 10 | 33 | |

TABLE 7-2

| Effective ingredient in the preparation | Treatment concentration (ppm) | Control value | Theoretical value |
|---|---|---|---|
| A + Carboxin (b-41) | 10 + 50 | 87 | 50 |
| A + Thifluzamide (b-42) | 10 + 50 | 100 | 78 |
| A + Isopyrazam (b-7) | 10 + 0.4 | 87 | 50 |
| A + Sedaxane (b-6) | 10 + 0.4 | 87 | 50 |
| A + Penflufen (b-5) | 10 + 2 | 100 | 78 |
| A + Cyprodinil (b-61) | 10 + 10 | 87 | 50 |
| A + Fenpyrazamine (b-99) | 10 + 50 | 87 | 44 |
| B + Carboxin (b-41) | 10 + 50 | 87 | 50 |
| B + Thifluzamide (b-42) | 10 + 50 | 100 | 78 |
| B + Isopyrazam (b-7) | 10 + 0.4 | 87 | 50 |
| B + Sedaxane (b-6) | 10 + 0.4 | 87 | 50 |
| B + Penflufen (b-5) | 10 + 2 | 100 | 78 |
| B + Cyprodinil (b-61) | 10 + 10 | 87 | 50 |
| B + Fenpyrazamine (b-99) | 10 + 50 | 87 | 44 |
| C + Carboxin (b-41) | 10 + 50 | 87 | 50 |
| C + Thifluzamide (b-42) | 10 + 50 | 100 | 78 |
| C + Isopyrazam (b-7) | 10 + 0.4 | 93 | 50 |
| C + Sedaxane (b-6) | 10 + 0.4 | 90 | 50 |
| C + Penflufen (b-5) | 10 + 2 | 100 | 78 |
| C + Cyprodinil (b-61) | 10 + 10 | 87 | 50 |
| C + Fenpyrazamine (b-99) | 10 + 50 | 87 | 44 |
| Carboxin (b-41) | 50 | 40 | |
| Thifluzamide (b-42) | 50 | 73 | |
| Isopyrazam (b-7) | 0.4 | 40 | |
| Sedaxane (b-6) | 0.4 | 40 | |
| Penflufen (b-5) | 2 | 73 | |
| Cyprodinil (b-61) | 10 | 40 | |
| Fenpyrazamine (b-99) | 50 | 33 | |
| A | 10 | 17 | |
| B | 10 | 17 | |
| C | 10 | 17 | |

TABLE 7-3

| Effective ingredient in the preparation | Treatment concentration (ppm) | Preventive value | Theoretical value |
|---|---|---|---|
| A + Tetraconazole (b-22) | 10 + 0.4 | 83 | 70 |
| A + Epoxiconazole (b-24) | 10 + 0.4 | 90 | 64 |
| A + Ipconazole (b-25) | 10 + 0.4 | 93 | 70 |
| A + Metconazole (b-26) | 10 + 0.4 | 90 | 70 |
| A + Propiconazole (b-27) | 10 + 0.4 | 93 | 64 |
| A + Cyproconazole (b-28) | 10 + 0.4 | 87 | 64 |
| A + Difenoconazole (b-29) | 10 + 0.4 | 90 | 70 |
| A + Fluquinconazole (b-30) | 10 + 0.4 | 90 | 70 |
| A + Flusilazole (b-31) | 10 + 0.4 | 87 | 64 |
| A + Penconazole (b-32) | 10 + 0.4 | 87 | 68 |
| A + Flutriafol (b-34) | 10 + 0.4 | 90 | 64 |
| A + Myclobutanil (b-35) | 10 + 0.4 | 93 | 68 |
| A + Imazalil (b-20) | 10 + 0.4 | 90 | 60 |
| A + Prochloraz (b-21) | 10 + 0.4 | 87 | 68 |
| B + Tetraconazole (b-22) | 10 + 0.4 | 87 | 67 |
| B + Epoxiconazole (b-24) | 10 + 0.4 | 83 | 60 |
| B + Ipconazole (b-25) | 10 + 0.4 | 87 | 67 |
| B + Metconazole (b-26) | 10 + 0.4 | 90 | 67 |
| B + Propiconazole (b-27) | 10 + 0.4 | 87 | 60 |
| B + Cyproconazole (b-28) | 10 + 0.4 | 83 | 64 |
| B + Difenoconazole (b-29) | 10 + 0.4 | 87 | 60 |
| B + Fluquinconazole (b-30) | 10 + 0.4 | 90 | 64 |
| B + Flusilazole (b-31) | 10 + 0.4 | 87 | 56 |
| B + Penconazole (b-32) | 10 + 0.4 | 90 | 64 |
| B + Flutriafol (b-34) | 10 + 0.4 | 87 | 60 |
| B + Myclobutanil (b-35) | 10 + 0.4 | 80 | 56 |
| B + Imazalil (b-20) | 10 + 0.4 | 83 | 60 |
| B + Prochloraz (b-21) | 10 + 0.4 | 87 | 67 |
| C + Tetraconazole (b-22) | 10 + 0.4 | 90 | 67 |
| C + Epoxiconazole (b-24) | 10 + 0.4 | 93 | 60 |
| C + Ipconazole (b-25) | 10 + 0.4 | 90 | 67 |
| C + Metconazole (b-26) | 10 + 0.4 | 90 | 67 |
| C + Propiconazole (b-27) | 10 + 0.4 | 90 | 60 |
| C + Cyproconazole (b-28) | 10 + 0.4 | 87 | 64 |
| C + Difenoconazole (b-29) | 10 + 0.4 | 90 | 60 |
| C + Fluquinconazole (b-30) | 10 + 0.4 | 87 | 64 |
| C + Flusilazole (b-31) | 10 + 0.4 | 90 | 56 |
| C + Penconazole (b-32) | 10 + 0.4 | 87 | 64 |
| C + Flutriafol (b-34) | 10 + 0.4 | 83 | 60 |
| C + Myclobutanil (b-35) | 10 + 0.4 | 87 | 56 |
| C + Imazalil (b-20) | 10 + 0.4 | 90 | 60 |
| C + Prochloraz (b-21) | 10 + 0.4 | 87 | 67 |
| Tetraconazole (b-22) | 0.4 | 50 | |
| Epoxiconazole (b-24) | 0.4 | 40 | |
| Ipconazole (b-25) | 0.4 | 50 | |
| Metconazole (b-26) | 0.4 | 50 | |
| Propiconazole (b-27) | 0.4 | 40 | |
| Cyproconazole (b-28) | 0.4 | 47 | |
| Difenoconazole (b-29) | 0.4 | 40 | |
| Fluquinconazole (b-30) | 0.4 | 47 | |
| Flusilazole (b-31) | 0.4 | 33 | |
| Penconazole (b-32) | 0.4 | 47 | |
| Flutriafol (b-34) | 0.4 | 40 | |
| Myclobutanil (b-35) | 0.4 | 33 | |
| Imazalil (b-20) | 0.4 | 40 | |
| Prochloraz (b-21) | 0.4 | 50 | |
| A | 10 | 40 | |
| B | 10 | 33 | |
| C | 10 | 33 | |

TABLE 7-4

| Effective ingredient in the preparation | Treatment concentration (ppm) | Preventive value | Theoretical value |
|---|---|---|---|
| A + Thiabendazole (b-60) | 10 + 10 | 90 | 64 |
| A + Benomyl (b-58) | 10 + 10 | 97 | 70 |
| A + Thiuram (b-68) | 10 + 50 | 87 | 60 |
| A + Metiram (b-67) | 10 + 50 | 87 | 60 |
| A + Folpet (b-70) | 10 + 50 | 80 | 60 |
| A + Pyrisoxazole (b-103) | 10 + 50 | 90 | 60 |
| B + Thiabendazole (b-60) | 10 + 10 | 97 | 64 |

TABLE 7-4-continued

| Effective ingredient in the preparation | Treatment concentration (ppm) | Preventive value | Theoretical value |
|---|---|---|---|
| B + Benomyl (b-58) | 10 + 10 | 93 | 70 |
| B + Thiuram (b-68) | 10 + 50 | 80 | 60 |
| B + Metiram (b-67) | 10 + 50 | 80 | 60 |
| B + Folpet (b-70) | 10 + 50 | 77 | 60 |
| B + Pyrisoxazole (b-103) | 10 + 50 | 97 | 60 |
| C + Thiabendazole (b-60) | 10 + 10 | 97 | 64 |
| C + Benomyl (b-58) | 10 + 10 | 97 | 70 |
| C + Thiuram (b-68) | 10 + 50 | 83 | 60 |
| C + Metiram (b-67) | 10 + 50 | 80 | 60 |
| C + Folpet (b-70) | 10 + 50 | 80 | 60 |
| C + Pyrisoxazole (b-103) | 10 + 50 | 90 | 60 |
| Thiabendazole (b-60) | 10 | 40 | |
| Benomyl (b-58) | 10 | 50 | |
| Thiuram (b-68) | 50 | 33 | |
| Metiram (b-67) | 50 | 33 | |
| Folpet (b-70) | 50 | 33 | |
| Pyrisoxazole (b-103) | 50 | 33 | |
| A | 10 | 40 | |
| B | 10 | 40 | |
| C | 10 | 40 | |

TABLE 7-5

| Effective ingredient in the preparation | Treatment concentration (ppm) | Preventive value | Theoretical value |
|---|---|---|---|
| A + Fenpropimorph (b-65) | 10 + 0.4 | 80 | 60 |
| A + Tridemorph (b-66) | 10 + 0.4 | 80 | 60 |
| A + Metrafenone (b-82) | 10 + 0.08 | 83 | 64 |
| A + Quinoxyfen (b-63) | 10 + 0.016 | 97 | 76 |
| A + Flutianil (b-77) | 10 + 0.016 | 97 | 80 |
| A + Proquinazid (b-100) | 10 + 0.016 | 97 | 64 |
| A + Spiroxamine (b-101) | 10 + 0.4 | 83 | 60 |
| A + Fenpropidin (b-102) | 10 + 0.4 | 97 | 64 |
| A + Sulfur (b-96) | 10 + 10 | 100 | 84 |
| A + Chinomethionat (b-74) | 10 + 0.4 | 83 | 70 |
| B + Fenpropimorph (b-65) | 10 + 0.4 | 80 | 60 |
| B + Tridemorph (b-66) | 10 + 0.4 | 80 | 60 |
| B + Metrafenone (b-82) | 10 + 0.08 | 83 | 64 |
| B + Quinoxyfen (b-63) | 10 + 0.016 | 83 | 76 |
| B + Flutianil (b-77) | 10 + 0.016 | 97 | 80 |
| B + Proquinazid (b-100) | 10 + 0.016 | 97 | 64 |
| B + Spiroxamine (b-101) | 10 + 0.4 | 87 | 60 |
| B + Fenpropidin (b-102) | 10 + 0.4 | 80 | 64 |
| B + Sulfur (b-96) | 10 + 10 | 97 | 84 |
| B + Chinomethionat (b-74) | 10 + 0.4 | 83 | 70 |
| C + Fenpropimorph (b-65) | 10 + 0.4 | 83 | 60 |
| C + Tridemorph (b-66) | 10 + 0.4 | 83 | 60 |
| C + Metrafenone (b-82) | 10 + 0.08 | 93 | 64 |
| C + Quinoxyfen (b-63) | 10 + 0.016 | 97 | 76 |
| C + Flutianil (b-77) | 10 + 0.016 | 97 | 80 |
| C + Proquinazid (b-100) | 10 + 0.016 | 97 | 64 |
| C + Spiroxamine (b-101) | 10 + 0.4 | 87 | 60 |
| C + Fenpropidin (b-102) | 10 + 0.4 | 80 | 64 |
| C + Sulfur (b-96) | 10 + 10 | 97 | 84 |
| C + Chinomethionat (b-74) | 10 + 0.4 | 80 | 70 |
| Fenpropimorph (b-65) | 0.4 | 33 | |
| Tridemorph (b-66) | 0.4 | 33 | |
| Metrafenone (b-82) | 0.08 | 40 | |
| Quinoxyfen (b-63) | 0.016 | 60 | |
| Flutianil (b-77) | 0.016 | 67 | |
| Proquinazid (b-100) | 0.016 | 40 | |
| Spiroxamine (b-101) | 0.4 | 33 | |
| Fenpropidin (b-102) | 0.4 | 40 | |
| Sulfur (b-96) | 10 | 73 | |
| Chinomethionat (b-74) | 0.4 | 50 | |
| A | 10 | 40 | |
| B | 10 | 40 | |
| C | 10 | 40 | |

TABLE 7-6

| Effective ingredient in the preparation | Treatment concentration (ppm) | Preventive value | Theoretical value |
|---|---|---|---|
| A + Tiadinil (b-45) | 10 + 10 | 87 | 64 |
| A + Probenazole (b-73) | 10 + 10 | 93 | 64 |
| A + Tebufloquin (b-64) | 10 + 10 | 90 | 80 |
| A + Isoprothiolane (b-71) | 10 + 10 | 83 | 64 |
| A + Pyroquilon (b-104) | 10 + 50 | 83 | 44 |
| A + Pencycuron (b-76) | 10 + 250 | 80 | 60 |
| B + Tiadinil (b-45) | 10 + 10 | 83 | 64 |
| B + Probenazole (b-73) | 10 + 10 | 87 | 64 |
| B + Tebufloquin (b-64) | 10 + 10 | 93 | 80 |
| B + Isoprothiolane (b-71) | 10 + 10 | 80 | 64 |
| B + Pyroquilon (b-104) | 10 + 50 | 80 | 44 |
| B + Pencycuron (b-76) | 10 + 250 | 80 | 60 |
| C + Tiadinil (b-45) | 10 + 10 | 93 | 64 |
| C + Probenazole (b-73) | 10 + 10 | 90 | 64 |
| C + Tebufloquin (b-64) | 10 + 10 | 87 | 80 |
| C + Isoprothiolane (b-71) | 10 + 10 | 80 | 64 |
| C + Pyroquilon (b-104) | 10 + 50 | 80 | 44 |
| C + Pencycuron (b-76) | 10 + 250 | 77 | 60 |
| Tiadinil (b-45) | 10 | 40 | |
| Probenazole (b-73) | 10 | 40 | |
| Tebufloquin (b-64) | 10 | 67 | |
| Isoprothiolane (b-71) | 10 | 40 | |
| Pyroquilon (b-104) | 50 | 7 | |
| Pencycuron (b-76) | 250 | 33 | |
| A | 10 | 40 | |
| B | 10 | 40 | |
| C | 10 | 40 | |

TABLE 7-7

| Effective ingredient in the preparation | Treatment concentration (ppm) | Preventive value | Theoretical value |
|---|---|---|---|
| A + Pyriofenone (b-83) | 10 + 0.08 | 93 | 64 |
| A + Compound of formula (XV)-1 (b-89) | 10 + 2 | 93 | 64 |
| A + Oxathiapiprolin (b-84) | 10 + 50 | 87 | 50 |
| A + Compound of formula (XIX) (b-94) | 10 + 10 | 93 | 70 |
| A + Compound of formula (XVII) (b-91) | 10 + 0.08 | 97 | 64 |
| A + Compound of formula (III) (b-8) | 10 + 0.4 | 97 | 76 |
| A + Compound of formula (IV) (b-9) | 10 + 0.4 | 97 | 76 |
| A + Isotianil (b-46) | 10 + 2 | 90 | 60 |
| A + Acibenzolar-S-methyl (b-72) | 10 + 2 | 90 | 60 |
| B + Pyriofenone (b-83) | 10 + 0.08 | 93 | 64 |
| B + Compound of formula (XV)-1 (b-89) | 10 + 2 | 93 | 64 |
| B + Oxathiapiprolin (b-84) | 10 + 50 | 87 | 50 |
| B + Compound of formula (XIX) (b-94) | 10 + 10 | 93 | 70 |
| B + Compound of formula (XVII) (b-91) | 10 + 0.08 | 97 | 64 |
| B + Compound of formula (III) (b-8) | 10 + 0.4 | 100 | 76 |
| B + Compound of formula (IV) (b-9) | 10 + 0.4 | 97 | 76 |
| B + Isotianil (b-46) | 10 + 2 | 93 | 60 |
| B + Acibenzolar-S-methyl (b-72) | 10 + 2 | 93 | 60 |
| C + Pyriofenone (b-83) | 10 + 0.08 | 93 | 64 |
| C + Compound of formula (XV)-1 (b-89) | 10 + 2 | 90 | 64 |
| C + Oxathiapiprolin (b-84) | 10 + 50 | 87 | 50 |
| C + Compound of formula (XIX) (b-94) | 10 + 10 | 93 | 70 |
| C + Compound of formula (XVII) (b-91) | 10 + 0.08 | 97 | 64 |
| C + Compound of formula (III) (b-8) | 10 + 0.4 | 97 | 76 |

TABLE 7-7-continued

| Effective ingredient in the preparation | Treatment concentration (ppm) | Preventive value | Theoretical value |
|---|---|---|---|
| C + Compound of formula (IV) (b-9) | 10 + 0.4 | 97 | 76 |
| C + Isotianil(b-46) | 10 + 2 | 90 | 60 |
| C + Acibenzolar-S-methyl (b-72) | 10 + 2 | 90 | 60 |
| Pyriofenone (b-83) | 0.08 | 40 | |
| Compound of formula (XV)-1 (b-89) | 2 | 40 | |
| Oxathiapiprolin (b-84) | 50 | 17 | |
| Compound of formula (XIX) (b-94) | 10 | 50 | |
| Compound of formula (XVII) (b-91) | 0.08 | 40 | |
| Compound of formula (III) (b-8) | 0.4 | 60 | |
| Compound of formula (IV) (b-9) | 0.4 | 60 | |
| Isotianil(b-46) | 2 | 33 | |
| Acibenzolar-S-methyl (b-72) | 2 | 33 | |
| A | 10 | 40 | |
| B | 10 | 40 | |
| C | 10 | 40 | |

TABLE 7-8

| Effective ingredient in the preparation | Treatment concentration (ppm) | Preventive value | Theoretical value |
|---|---|---|---|
| A + Phosphorous acid (b-105) | 10 + 50 | 93 | 60 |
| A + Propineb (b-69) | 10 + 50 | 97 | 50 |
| A + Compound of (V) (b-36) | 10 + 0.4 | 90 | 60 |
| A + Compound of (XIV) (b-88) | 10 + 0.4 | 93 | 64 |
| A + Compound of (XI)-1 (b-85) | 10 + 10 | 97 | 70 |
| A + Compound of (XI)-2 (b-85) | 10 + 10 | 93 | 70 |
| A + Compound of (XVIII) (b-92) | 10 + 0.4 | 90 | 64 |
| A + D-tagatose (b-93) | 10 + 5000 | 93 | 60 |
| B + Phosphorous acid (b-105) | 10 + 50 | 90 | 60 |
| B + Propineb (b-69) | 10 + 50 | 97 | 50 |
| B + Compound of (V) (b-36) | 10 + 0.4 | 93 | 60 |
| B + Compound of (XIV) (b-88) | 10 + 0.4 | 93 | 64 |
| B + Compound of (XI)-1 (b-85) | 10 + 10 | 93 | 70 |
| B + Compound of (XI)-2 (b-85) | 10 + 10 | 97 | 70 |
| B + Compound of (XVIII) (b-92) | 10 + 0.4 | 97 | 64 |
| B + D-tagatose (b-93) | 10 + 5000 | 93 | 60 |
| C + Phosphorous acid (b-105) | 10 + 50 | 90 | 60 |
| C + Propineb (b-69) | 10 + 50 | 97 | 50 |
| C + Compound of (V) (b-36) | 10 + 0.4 | 93 | 60 |
| C + Compound of (XIV) (b-88) | 10 + 0.4 | 97 | 64 |
| C + Compound of (XI)-1 (b-85) | 10 + 10 | 90 | 70 |
| C + Compound of (XI)-2 (b-85) | 10 + 10 | 90 | 70 |
| C + Compound of (XVIII) (b-92) | 10 + 0.4 | 93 | 64 |
| C + D-tagatose (b-93) | 10 + 5000 | 93 | 60 |
| Phosphorous acid (b-105) | 50 | 33 | |
| Propineb (b-69) | 50 | 17 | |
| Compound of (V) (b-36) | 0.4 | 33 | |
| Compound of (XIV) (b-88) | 0.4 | 40 | |
| Compound of (XI)-1 (b-85) | 10 | 50 | |
| Compound of (XI)-2 (b-85) | 10 | 50 | |
| Compound of (XVIII) (b-92) | 0.4 | 40 | |

TABLE 7-8-continued

| Effective ingredient in the preparation | Treatment concentration (ppm) | Preventive value | Theoretical value |
|---|---|---|---|
| D-tagatose (b-93) | 5000 | 33 | |
| A | 10 | 40 | |
| B | 10 | 40 | |
| C | 10 | 40 | |

From the results shown in the above-mentioned Table 7-1 to 7-8, it could be understood that synergistic effects could be obtained when Compound A, B or C and the compound of Group b are used in combination. Incidentally, even when Compound A, B or C and the compound of Group b are used in combination, no chemical damage symptom was admitted in the plant material, cucumber (variety: Sagamihanpaku).

Comparative Example 3 Cucumber Powdery Mildew Preventive Test

Wettable powder prepared in compliance with Comparative Preparation Example 4 containing the compounds indicated in Table 7-9 were sprayed to the cucumber leaves, a conidiospore suspension prepared from *Sphaerotheca fuliginea* was inoculated onto the plants, and the controlling effects were examined in a manner similar to Test Example 6. The results and theoretical values as determined according to Colby's formula are shown in Table 7-9.

TABLE 7-9

| Effective ingredient in the preparation | Treatment concentration (ppm) | Preventive value | Theoretical value |
|---|---|---|---|
| A + Diclocymet | 10 + 50 | 50 | 60 |
| A + Carpropamid | 10 + 50 | 47 | 64 |
| A + Tolclofos-methyl | 10 + 50 | 40 | 60 |
| A + Oxolinic acid | 10 + 50 | 40 | 60 |
| B + Diclocymet | 10 + 50 | 40 | 60 |
| B + Carpropamid | 10 + 50 | 40 | 64 |
| B + Tolclofos-methyl | 10 + 50 | 40 | 60 |
| B + Oxolinic acid | 10 + 50 | 40 | 60 |
| C + Diclocymet | 10 + 50 | 40 | 60 |
| C + Carpropamid | 10 + 50 | 40 | 64 |
| C + Tolclofos-methyl | 10 + 50 | 33 | 60 |
| C + Oxolinic acid | 10 + 50 | 33 | 60 |
| Diclocymet | 50 | 40 | |
| Carpropamid | 50 | 33 | |
| Tolclofos-methyl | 50 | 33 | |
| Oxolinic acid | 50 | 33 | |
| A | 10 | 40 | |
| B | 10 | 40 | |
| C | 10 | 40 | |

Based on the results shown in Tables 7-9 above, even if these compounds are used in combination with Compound A, Compound B or Compound C, the controlling effects were under their theoretical values and the action resulting from combining two types of active ingredients is indicated to be antagonistic.

Test Example 7 Cucumber Downy Mildew Preventive Test

In a greenhouse, cucumber (variety: Sagamihanshiro) planted in a plastic pot having a diameter of 5 cm was grown to the 3rd to 5th-leaf stage. Spray was carried out in the same manner as in Test example 1, and after drying the chemical liquid, the pots were transferred into a greenhouse. After 3 days from the spray, a zoosporangium suspension of *Pseudoperonospora cubensis* was inoculated. After inoculation, the pots were placed in a high-humidity chamber (20 to 25° C.), transferred into a greenhouse on the next day, and controlling effects were examined after 7 days from the inoculation. A ratio of lesion area occupied per one leaf of cucumber was determined according to the same index as in Test example 1, and the control value and the theoretical value according to Colby's formula were similarly calculated. The results are shown in Tables 8.

TABLE 8

| Effective ingredient in the preparation | Treatment concentration (ppm) | Preventive value | Theoretical value |
|---|---|---|---|
| A + Mandipropamid (b-44) | 10 + 0.08 | 100 | 76 |
| A + Fluopicolide (b-40) | 10 + 2 | 97 | 76 |
| A + Benalaxyl-M (b-75) | 10 + 2 | 100 | 76 |
| A + Iprovalicarb (b-50) | 10 + 2 | 93 | 63 |
| A + Amisulbrom (b-97) | 10 + 0.08 | 93 | 76 |
| A + Ametoctradin (b-95) | 10 + 2 | 93 | 63 |
| A + Zoxamide (b-39) | 10 + 0.4 | 93 | 51 |
| A + Hymexazol (b-106) | 10 + 250 | 93 | 39 |
| B + Mandipropamid (b-44) | 10 + 0.08 | 97 | 74 |
| B + Fluopicolide (b-40) | 10 + 2 | 93 | 74 |
| B + Benalaxyl-M (b-75) | 10 + 2 | 97 | 74 |
| B + Iprovalicarb (b-50) | 10 + 2 | 93 | 62 |
| B + Amisulbrom (b-97) | 10 + 0.08 | 93 | 74 |
| B + Ametoctradin (b-95) | 10 + 2 | 97 | 62 |
| B + Zoxamide (b-39) | 10 + 0.4 | 93 | 49 |
| B + Hymexazol (b-106) | 10 + 250 | 93 | 36 |
| C + Mandipropamid (b-44) | 10 + 0.08 | 93 | 72 |
| C + Fluopicolide (b-40) | 10 + 2 | 90 | 72 |
| C + Benalaxyl-M (b-75) | 10 + 2 | 90 | 72 |
| C + Iprovalicarb (b-50) | 10 + 2 | 93 | 58 |
| C + Amisulbrom (b-97) | 10 + 0.08 | 97 | 72 |
| C + Ametoctradin (b-95) | 10 + 2 | 97 | 58 |
| C + Zoxamide (b-39) | 10 + 0.4 | 97 | 44 |
| C + Hymexazol (b-106) | 10 + 250 | 87 | 31 |
| Mandipropamid (b-44) | 0.08 | 67 | |
| Fluopicolide (b-40) | 2 | 67 | |
| Benalaxyl-M (b-75) | 2 | 67 | |
| Iproyalicarb (b-50) | 2 | 50 | |
| Amisulbrom (b-97) | 0.08 | 67 | |
| Ametoctradin (b-95) | 2 | 50 | |
| Zoxamide (b-39) | 0.4 | 33 | |
| Hymexazol (b-106) | 250 | 17 | |
| A | 10 | 27 | |
| B | 10 | 23 | |
| C | 10 | 17 | |

From the results of the above-mentioned Tables 8, it could be understood that synergistic effects could be obtained when Compound A, B or C and the compound of Group b are used in combination. Incidentally, even when Compound A, B or C and the compound of Group b are used in combination, no chemical damage symptom was admitted in the plant material, cucumber (variety: Sagamihanpaku).

INDUSTRIAL APPLICABILITY

The plant disease control composition of the present invention is used as a superior plant disease control agent since it has a plurality of disease spectra against various plant pathogens, including fungicide-resistant organisms (such as *Pyricularia oryzae* that causes rice blast or *Botrytis cinerea* that causes gray mold in tomatoes, cucumbers and green beans), exhibits superior control effects (synergistic control effects) that cannot be predicted from the individual components alone, demonstrates a high level of plant disease control effects even against organisms resistant to existing chemical agents, and is observed to be free of the occurrence of phytotoxicity.

The invention claimed is:

1. A plant disease control composition comprising as active ingredients thereof:

(a) at least one quinoline compound selected from the group consisting of (a-14) 3-(5-fluoro-3,3,4,4-tetramethyl-3,4-dihydroisoquinolin-1-yl)quinoline, (a-18) 3-(4,4-difluoro-3,3-dimethyl-3,4-dihydroisoquinolin-1-yl)quinoline, and (a-20) 3-(4,4,5-trifluoro-3,3-dimethyl-3,4-dihydroisoquinolin-1-yl)quinoline, or a salt thereof (group a); and (b) one or more fungicidal compounds selected from (group b):

pyrazole carboxamides consisting of (b-2) Benzovindiflupyr, and (b-3) a compound of formula (II)

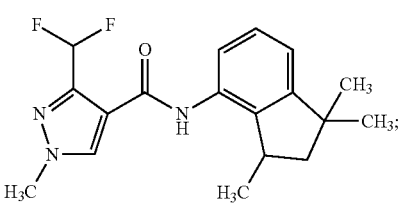

azole compounds consisting of (b-36) compounds of general formula (V)

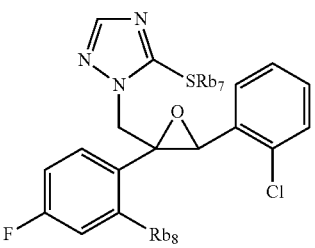

wherein $Rb_7$ represents a hydrogen atom, alkyl group, allyl group, benzyl group, amino group, cyano group or a valency that forms a double bond between a sulfur atom and a triazole ring to generate a ring represented by:

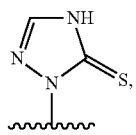

and

Rb$_8$ represents a hydrogen atom or fluorine atom, and
and (b-38) compounds of general formula (VII)

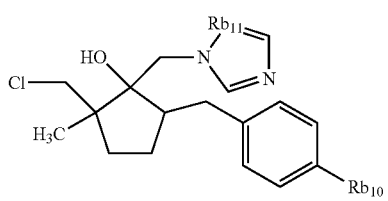

(VII)

wherein Rb$_{10}$ represents a halogen atom and Rb$_{11}$ represents a nitrogen atom or methine group;

amide compounds consisting of (b-47) Isofetamid, (b-48) Valifenalate, and (b-49) Pyraziflumid,

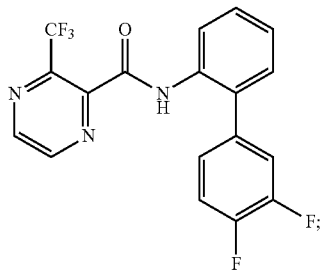 [SMILES: O=C(Nc1ccccc1-c1ccc(F)c(F)c1)c1nccnc1C(F)(F)F]

a strobilurin compound consisting of (b-56) Mandestrobin;

an aminopyridine compound consisting of (b-78) Picarbutrazox;

other fungicidal compounds (i) consisting of (b-84) Oxathiapiprolin, (b-85) compounds of general formula (XI)

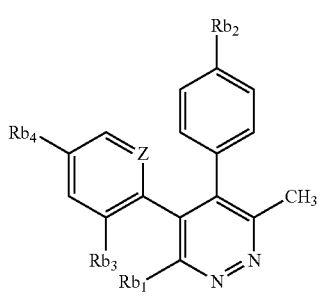

(XI)

wherein Rb$_1$ represents a chlorine atom, bromine atom, cyano group, methyl group or methoxy group, Rb$_2$ represents a fluorine atom or hydrogen atom, Rb$_3$ represents a halogen atom, Rb$_4$ represents a halogen atom, methoxy group or hydrogen atom and Z represents N or C—F, (b-88) a compound of formula (XIV)

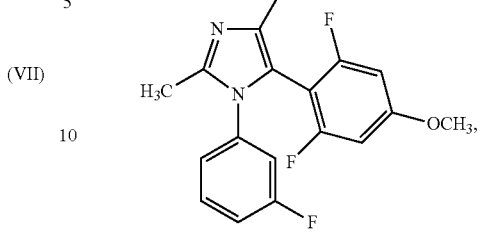

(XIV)

(b-89) compounds of general formula (XV)

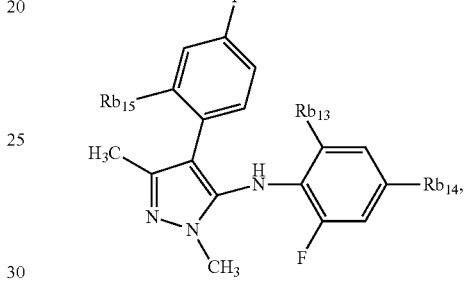

(XV)

wherein Rb$_{13}$ represents a chlorine atom or fluorine atom,

Rb$_{14}$ represents a chlorine atom or hydrogen atom and

Rb$_{15}$ represents a chlorine atom or bromine atom;

other fungicidal compounds (ii) consisting of (b-91) a compound of formula (XVII)

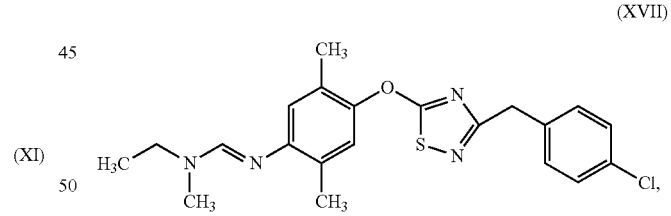

(XVII)

(b-92) a compound of formula (XVIII)

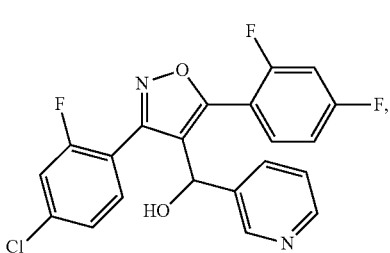

(XVIII)

(b-93) D-tagatose, and (b-94) compounds of general formula (XIX)

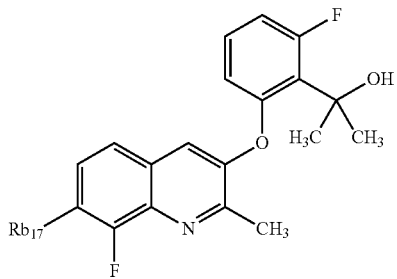

(XIX)

wherein $Rb_{17}$ represents a hydrogen atom or fluorine atom.

2. A method for controlling plant disease, comprising applying the plant disease control composition according to claim 1.

3. A method for controlling plant disease, comprising simultaneously applying a plant disease control composition containing a quinoline compound of group a as an active ingredient thereof and a plant disease control composition containing a fungicidal compound of group b as an active ingredient thereof, or applying one of either a plant disease control composition containing a quinoline compound of group a as an active ingredient thereof or a plant disease control composition containing a fungicidal compound of group b as an active ingredient thereof, followed by applying the other composition, wherein each of the plant disease compositions is in accordance with claim 1.

* * * * *